United States Patent
DeLuca et al.

(10) Patent No.: US 8,664,206 B2
(45) Date of Patent: *Mar. 4, 2014

(54) DIASTEREOMERS OF 2-METHYLENE-19-NOR-22-METHYL-1α,25-DIHYDROXYVITAMIN D₃

(75) Inventors: Hector F. DeLuca, Deerfield, WI (US); Agnieszka Flores, Madison, WI (US); Pawel Grzywacz, Madison, WI (US); Lori A. Plum, Arena, WI (US); Margaret Clagett-Dame, Deerfield, WI (US); James B. Thoden, Madison, WI (US); Hazel M. Holden, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/344,987

(22) Filed: Jan. 6, 2012

(65) Prior Publication Data

US 2012/0165300 A1    Jun. 28, 2012

Related U.S. Application Data

(63) Continuation-in-part of application No. 13/069,074, filed on Mar. 22, 2011.

(60) Provisional application No. 61/316,653, filed on Mar. 23, 2010.

(51) Int. Cl.
*A61K 31/593* (2006.01)
*C07C 401/00* (2006.01)
*C07C 35/23* (2006.01)

(52) U.S. Cl.
USPC .............. 514/167; 552/653; 568/819

(58) Field of Classification Search
USPC .............. 514/167; 552/653; 568/819
See application file for complete search history.

(56) References Cited

U.S. PATENT DOCUMENTS

| | | | |
|---|---|---|---|
| 5,086,191 A | 2/1992 | DeLuca et al. | |
| 5,246,925 A | 9/1993 | DeLuca et al. | |
| 5,536,713 A | 7/1996 | DeLuca et al. | |
| 5,585,369 A | 12/1996 | DeLuca et al. | |
| 5,587,497 A | 12/1996 | DeLuca et al. | |
| 5,843,928 A | 12/1998 | DeLuca et al. | |
| 5,936,133 A | 8/1999 | DeLuca et al. | |
| 5,945,410 A | 8/1999 | DeLuca et al. | |
| 6,384,087 B1 | 5/2002 | Zemel et al. | |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 6,774,251 B2 | 8/2004 | DeLuca et al. | |
| 6,806,262 B2 | 10/2004 | DeLuca et al. | |
| 6,835,723 B2 | 12/2004 | DeLuca et al. | |
| 6,844,330 B2 | 1/2005 | DeLuca et al. | |
| 6,844,331 B2 | 1/2005 | DeLuca et al. | |
| 6,844,332 B2 | 1/2005 | DeLuca et al. | |
| 6,844,457 B2 | 1/2005 | DeLuca et al. | |
| 6,846,811 B2 | 1/2005 | DeLuca et al. | |
| 6,887,860 B2 | 5/2005 | DeLuca et al. | |
| 6,890,914 B2 | 5/2005 | DeLuca et al. | |
| 6,894,037 B2 | 5/2005 | DeLuca et al. | |
| 6,939,868 B2 | 9/2005 | DeLuca et al. | |
| 6,992,074 B2 | 1/2006 | DeLuca et al. | |
| 7,053,075 B2 | 5/2006 | DeLuca et al. | |

(Continued)

FOREIGN PATENT DOCUMENTS

| JP | 3210156 | 9/1991 |
|---|---|---|
| WO | WO-98/41501 | 9/1998 |

(Continued)

OTHER PUBLICATIONS

Fujishima et al., "Highly Potent Cell Differntiation-Inducing Analogues of 1alpha,25-Dihydroxyvitamin D3: Synthesis and Biological Activity of 2-Methyl-1,25-dihydroxyvitamin D3 with Side-Chain Modifications", Bioorganic & Medicinal Chemistry, vol. 9, pp. 525-535, 2001.*

(Continued)

*Primary Examiner* — Barbara P Badio
(74) *Attorney, Agent, or Firm* — Foley & Lardner LLP

(57) ABSTRACT

Compounds of formula I are provided where $X^1$, $X^2$, and $X^3$ are independently selected from H or hydroxy protecting groups. Such compounds may be used in preparing pharmaceutical compositions and are useful in treating a variety of biological conditions.

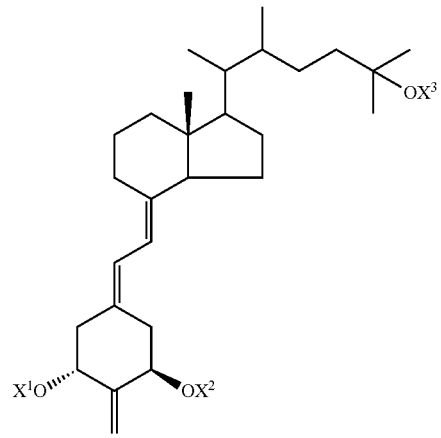

22 Claims, 20 Drawing Sheets

(56) References Cited

U.S. PATENT DOCUMENTS

| | | |
|---|---|---|
| 7,056,904 B2 | 6/2006 | DeLuca et al. |
| 7,064,115 B2 | 6/2006 | DeLuca et al. |
| 7,071,179 B2 | 7/2006 | DeLuca et al. |
| 7,094,774 B2 | 8/2006 | DeLuca et al. |
| 7,094,916 B2 | 8/2006 | DeLuca et al. |
| 7,112,579 B2 | 9/2006 | DeLuca et al. |
| 7,115,594 B2 | 10/2006 | DeLuca et al. |
| 7,141,558 B2 | 11/2006 | DeLuca et al. |
| 7,205,286 B2 | 4/2007 | DeLuca et al. |
| 7,208,484 B2 | 4/2007 | DeLuca et al. |
| 7,214,670 B2 | 5/2007 | DeLuca et al. |
| 7,214,671 B2 | 5/2007 | DeLuca et al. |
| 7,232,810 B2 | 6/2007 | DeLuca et al. |
| 7,238,681 B2 | 7/2007 | DeLuca et al. |
| 7,241,748 B2 | 7/2007 | DeLuca et al. |
| 7,241,749 B2 | 7/2007 | DeLuca et al. |
| 7,241,750 B2 | 7/2007 | DeLuca et al. |
| 7,241,751 B2 | 7/2007 | DeLuca et al. |
| 7,241,752 B2 | 7/2007 | DeLuca et al. |
| 7,241,909 B2 | 7/2007 | DeLuca et al. |
| 7,244,719 B2 | 7/2007 | DeLuca et al. |
| 7,300,925 B2 | 11/2007 | DeLuca et al. |
| 7,468,361 B2 | 12/2008 | DeLuca et al. |
| 7,511,030 B2 | 3/2009 | DeLuca et al. |
| 7,534,778 B2 | 5/2009 | DeLuca et al. |
| 7,541,348 B2 | 6/2009 | DeLuca et al. |
| 7,541,349 B2 | 6/2009 | DeLuca et al. |
| 7,563,783 B2 | 7/2009 | DeLuca et al. |
| 7,648,972 B2 | 1/2010 | DeLuca et al. |
| 7,648,973 B2 | 1/2010 | DeLuca et al. |
| 7,704,980 B2 | 4/2010 | DeLuca et al. |
| 7,704,981 B2 | 4/2010 | DeLuca et al. |
| 7,704,982 B2 | 4/2010 | DeLuca et al. |
| 7,713,951 B2 | 5/2010 | DeLuca et al. |
| 7,713,952 B2 | 5/2010 | DeLuca et al. |
| 7,718,636 B2 | 5/2010 | DeLuca et al. |
| 7,718,637 B2 | 5/2010 | DeLuca et al. |
| 7,718,638 B2 | 5/2010 | DeLuca et al. |
| 7,741,313 B2 | 6/2010 | DeLuca et al. |
| 7,741,314 B2 | 6/2010 | DeLuca et al. |
| RE41,474 E | 8/2010 | DeLuca et al. |
| RE41,491 E | 8/2010 | DeLuca et al. |
| 7,888,339 B2 | 2/2011 | DeLuca et al. |
| 7,893,043 B2 | 2/2011 | DeLuca et al. |
| 7,915,242 B2 | 3/2011 | DeLuca et al. |
| 2005/0065088 A1 | 3/2005 | Thompson |
| 2005/0065133 A1 | 3/2005 | Lee et al. |
| 2005/0065180 A1 | 3/2005 | Lee |
| 2005/0070512 A1 | 3/2005 | Lee |
| 2005/0119242 A1 | 6/2005 | DeLuca et al. |
| 2007/0219168 A1 | 9/2007 | DeLuca et al. |
| 2009/0170820 A1 | 7/2009 | DeLuca et al. |
| 2009/0227545 A1 | 9/2009 | DeLuca et al. |
| 2010/0009946 A1 | 1/2010 | DeLuca et al. |
| 2010/0009947 A1 | 1/2010 | DeLuca et al. |
| 2010/0160267 A1 | 6/2010 | DeLuca et al. |
| 2010/0179344 A1 | 7/2010 | DeLuca et al. |
| 2011/0034426 A1 | 2/2011 | DeLuca et al. |
| 2011/0059926 A1 | 3/2011 | DeLuca et al. |
| 2011/0086824 A1 | 4/2011 | DeLuca et al. |

FOREIGN PATENT DOCUMENTS

| | | |
|---|---|---|
| WO | WO-00/59513 | 10/2000 |
| WO | WO-02/17734 | 3/2002 |
| WO | WO-2005/027913 | 3/2005 |
| WO | WO-2005/027915 | 3/2005 |
| WO | WO-2005/027924 | 3/2005 |
| WO | WO-2005/027929 | 3/2005 |
| WO | WO-2005/027931 | 3/2005 |
| WO | WO-2006/057886 | 6/2006 |
| WO | WO-2006/119309 | 11/2006 |
| WO | WO-2009/026265 | 2/2009 |

OTHER PUBLICATIONS

U.S. Appl. No. 10/613,201, filed Jul. 3, 2003, DeLuca et al.

Arbour, Nancy C. et al., "A Highly Sensitive Method for Large-Scale Measurements of 1,25-Dihydroxyvitamin D," *Analytical Biochemistry*, 1998, vol. 255, pp. 148-154.

Baggiolini et al., "Stereocontrolled Total Synthesis of 1α,25-Dihydroxyergocalciferol and 1α,25-Dihydroxyergocalciferol," *J. Org. Chem.*, (1986), vol. 51, pp. 3098-3108, published by American Chemical Society.

Casimir, D.A., et al., "cAMP Activates the Expression of Stearoly-CoA Desaturase Gene 1 during Early Preadipocyte Differentiation," *J. Biol. Chem.*, (1996), 271(47), pp. 29847-29853; The American Society for Biochemistry and Molecular Biology, Inc.

Chomczynski, P. et al., "Single-Step Method of RNA Isolation by Acid Guanidinium Thiocyanate-Phenol-Chloroform Extration," *Anal. Biochem.*, (1987), 162, pp. 156-159; Academic Press, Inc.

Cohen, P. et al., "Role for Stearoyl-CoA Desaturase-1 in Leptin-Mediated Weight Loss," *Science* (2002), 297, pp. 240-243.

Collins et al., "Normal Functional Characteristics of Cultured Human Promyelocytic Leukemia Cells (HL-60) After Induction of Differentiation by Dimethylsufoxide" *J. Exp. Med.*, (1979), 149, pp. 969-974.

Dame et al., "Monoclonal Antibodies to the Porcine Intestinal Receptor for 1,25-Dihydroxyvitamin D3: Interaction with Distinct Receptor Domains," *Biochemistry*, (1986); vol. 25, pp. 4523-4534; American Chemical Society.

Daniewski, A. R. et al., "A Novel Silylcopper Catalyst for the Reductive Bromination of Hajos Dione. Improved Preparation of a CD Synthon for the Synthesis of Vitamin D," *J. Org. Chem.*, (2001), 66, pp. 626-628; American Chemical Society.

Deluca, H. F., "Applications of New Vitamin D. Compounds to Disease," *DN&P*, (Mar. 1992), vol. 5, No. 2, pp. 87-92.

Grzywacz, P. et al., "Methyl substitution of the 25-hydroxy group on 2-methylene-19-nor-1α,25-dihydroxyvitamin D3 (2MD) reduces potency but allows bone selectivity", *Biochemistry*, (2007), vol. 460, pp. 274-284, Elsevier Inc.

Hanessian et al., "Total Synthesis of (−)-Reserpine Using the Chiron Approach," *J. Org. Chem.*, 62, (1997), pp. 465-473; American Chemical Society.

International Search Report and Written Opinion for Intl. Pat. Appln. No. PCT/US2010/058208, mailed on Feb. 10, 2011, 12 pp.

International Search Report and Written Opinion for Intl. Pat. Appln. No. PCT/US2011/029452, mailed on Jul. 14, 2011, 11 pp.

Kutner et al., "Novel Convergent Synthesis of Side-Chain-Modified Analogues of 13β1,25-Dihydroxycholecalciferol and 13β1,25-Dihydroxyergocalciferol," *J. Org. Chem.*, (1988), vol. 53, pp. 3450-3457; American Chemical Society.

Lythgoe et al., "Calciferol and its Relatives. Part 22. A direct total Synthesis of Vitamin D2 and Vitamin D3," *J. Chem. Soc. Perkin I*, (1978), pp. 590-595.

Lythgoe, "Synthetic Approaches to Vitamin D and its Relatives," *Chem. Soc. Rev.*, (1983), vol. 9, pp. 449-475.

Mascareñas et al., "Studies on the Synthesis of Side-Chain Hydroxylated Metabolites of Vitamin D. 3. Synthesis of 25-Ketovitamin D3 and 25-Hydroxyvitamin D3," *J. Org. Chem.*, vol. 51, pp. 1269-1272 (1986); American Chemical Society.

Mincione et al., "Improved Conversion of Vitamin D2 into the Windaus Ketone and its Regioselective Hydroxylation via Organoboranes at C26," *Synth. Commun.*, vol. 19(5&6), pp. 723-735 (1989).

Miyamoto et al., "Synthetic Studies of Vitamin D Analogues. XIV. Synthesis and Calcium Regulating Activity of Vitamin D3 Analogues Bearing a Hydroxyalkoxy Group at the 20A-Position," *Chem. Pharm. Bull.*, vol. 41(6), pp. 1111-1113 (1993); Pharmaceutical Society of Japan.

Nishii et al., "The Development of Vitamin D3 Analogues for the Treatment of Osteoporosis," *Osteoporosis Int. Suppl.*, vol. 1, 190-193 (1993); European Foundation for Osteoporosis.

Okano et al., "Regulatory Activities of 20A-(3-Hydroxypropoxy)-13β1, 25-Dihydroxy-Vitamin D3, a Novel Synthetic Vitamin D3 Derivative, on Calcium Metabolism," *Biochem. Biophys. Res. Commun.*, vol. 163(3), pp. 1444-1449 (1989); published by Academic Press, Inc.

(56) References Cited

OTHER PUBLICATIONS

Ostrem et al., "24- and 26-homo-1,25-dihydroxyvitamin D3: Preferential activity in inducing differentiation of human leukemia cells HL-60 in vitro," *Proc. Natl. Acad. Sci. USA*, vol. 84, pp. 2610-2614 (1987).

Ostrem et al., "Induction of Monocytic Differentiation of HL-60 Cells by 1,25-Dihydroxyvitamin D Analogs," *J. Biol. Chem.*, vol. 262(29), pp. 14164-14171 (1987); The American Society for Biochemistry and Molecular Biology, Inc.

Peleg, S., Chapter 60: Molecular Basis for Differential Action of Vitamin D Analogs, In: Vitamin D, Feldman, *Glorieux and Pike* (eds.), pp. 1011-1025 (1997); Academic Press.

Perlman et al., "13B1,25-Dihydroxy-19-Nor-Vitamin D3, A Novel Vitamin D-Related Compound with Potential Therapeutic Activity," *Tetrahedron Lett.*, vol. 31(13), pp. 1823-1824 (1990); Pergamon Press, Great Britain.

Perlman et al., "Novel Synthesis of 19-Nor-Vitamin D Compounds," *Tetrahedron Lett.*, vol. 32(52), pp. 7663-7666 (1991); Pergamon Press, Great Britain.

Peterson et al., "Studies of the Ketone Obtained from the Ozonolysis of Vitamin D. Molecular Mechanics Calculations for It and Related Hydrindanones," *J. Org. Chem.*, vol. 51, pp. 1948-1954 (1986); American Chemical Society.

Plum, L. A. et al., "Biologically active noncalcemic analogs of 13B1,25-dihydroxyvitamin D with an abbreviated side chain containing no hydroxyl," *Proc. Natl. Acad. Sci. USA*, 101(18), pp. 6900-6904 (2004).

Posner et al., "2-Fluoroalkyl A-Ring Analogs of 1,25-Dihydroxyvitamin D3 Stereocontrolled Total Synthesis via Intramolecular and Intermolecular Diels 013 Alder Cycloadditions. Preliminary Biological Testing," *J. Org. Chem.*, vol. 60, pp. 4617-1628 (1995); American Chemical Society.

Posner et al., "Stereocontrolled Total Synthesis of Calcitriol Derivatives: 1,25-Dihydroxy-2(4019-hydroxybutyl)vitamin D3 Analogs of an Osteoporosis Drug," *J. Org. Chem.*, vol. 59, pp. 7855-7861 (1994); American Chemical Society.

Qiu, Z. et al., "DNA Synthesis and Mitotic Clonal Expansion is Not a Required Step for 3T3-L1 Preacipocyte Differentiation into Adipocytes," *J. Biol. Chem.*, 276(15), pp. 11988-11995 (2001); The American Society for Biochemistry and Molecular Biology, Inc.

Sakuma, T. et al., "Inhibition of Peroxisome Proliferator-activated Receptor 13B1 Signaling by Vitamin D Receptor," *Biochem. Biophys. Res. Commun.*, vol. 312, pp. 513-519 (2003).

Sardina et al., "Studies on the Synthesis of Side-Chain Hydroxylated Metabolites of Vitamin D. 2. Stereocontrolled Synthesis of 25-Hydroxyvitamin D2," *J. Org. Chem.*, vol. 51, 1264-1269 (1986); American Chemical Society.

Sakamaki, Y. et al., "Potent antagonist for the vitamin D receptor: vitamin D analogues side chain structure", *J. Med. Chem.*, Jul. 7, 2010, vol. 53, No. 7, pp. 5813-5826.

Sato, M. et al., "Demonstration of 13B1,25-Dihydroxyvitamin D3 Receptor-Like Molecule in ST 13 and 3T3 L1 Preadipocytes and its Inhibitory Effects on Preadipocyte Differentiation," *J. Cell. Phys.*, 135, pp. 545-550 (1988); Alan R. Liss, Inc.

Shi et al., "1a,25-Dihydroxyvitamin D3 modulates human adipocyte metabolism via nongenomic action," *The FASEB Journal* (Dec. 2001), vol. 15, pp. 2751-2753.

Sicinski, R. R. et al., "New 13B1,25-Dihydroxy-19-norvitamin D3 Compounds of High Biological Activity: Synthesis and Biological Evaluation of 2-Hydroxymethyl, 2-Methyl, and 2-Methylene Analogues," *J. Med. Chem.*, 41, pp. 4662-4674 (1998); American Chemical Society.

Sicinski, R. R. et al., "Synthesis and Biological Activity of 2-Hydroxy and 2-Alkoxy Analogs of 13B1,25-Dihydroxy-19-norvitamin D3," *J. Med. Chem.*, 37, pp. 3730-3738 (1994); American Chemical Society.

Silverman, R.B., *The Organic Chemistry of Drug Design and Drug Action*, 2nd Edition, (2004), ISBN: 0-12-643732-7, Title/Cover, 1 page, Contents, 1 page, pp. 26-28, and Publication Information, 1 page; Elsevier Academic Press, U.S.A.

Suda, T. et al., "Biological Activity of 25-Hydroxyergocalciferol in Rats," *J. Nutrition*, vol. 100, pp. 1049-1052 (1970).

Toh et al., "Studies on a Convergent Route to Side-Chain Analogues of Vitamin D: 25-Hydroxy-23-oxavitamin D3," *J. Org. Chem.*, 48, pp. 1414-1417 (1983); American Chemical Society.

Xue et al., "Mechanism of intracellular calcium ([Ca2+]i) inhibition of lipolysis in human adipocytes," The FASEB Journal (Nov. 17, 2001), vol. 15, pp. 2527-2529.

Binderup, Lise et al., "Effects of a Novel Vitamin D Analogue MC903 on Cell Proliferation and Differentiation In Vitro and on Calcium Metabolism In Vivo," Biochemical Pharmacology, (1988), vol. 37, No. 5, pp. 889-895.

Campbell, Moray J. et al., "Toward Therapeutic Intervention of Cancer by Vitamin D Compounds," Journal of the National Cancer Institute, (Feb. 5, 1997), vol. 89, No. 3, pp. 182-185.

Cantorna, Margherita T. et al., "1,25 Dihydroxyvitamin D3 Reversibly Blocks the Progression of Relapsing Encephalomyelitis, A Model of Multiple Sclerosis," Proc. Natl. Acad. Sci. USA, (Jul. 1996), vol. 93, pp. 7861-7864.

Gallagher, J.C. et al., "Effects of Calcitriol in Osteoporosis," Osteoporosis: Recent Advanced in Pathogenesis and Treatment, University Park Press, Baltimore, Maryland, (1981), pp. 419-423.

Gallagher, J.C. et al., "Intestinal Calcium Absorption and Serum Vitamin D Metabolites in Normal Subjects and Osteoporotic Patients: Effect of Age and Dietary Calcium," J. Clin. Invest., (Sep. 1979), vol. 64, pp. 729-736.

Geilen, Christoph et al., "The Vitamin D3 Analogue, Calcipotriol, Induces Sphingomyelin Hydrolysis in Human Keratinocytes," FEBS Letters, (1996), vol. 378, pp. 88-92.

International Preliminary Report on Patentability dated Sep. 25, 2012 for Intl. Pat. Appln. No. PCT/US2011/029452, 7 pp.

Munker, Reinhold et al., "A New Series of Vitamin D Analogs is Highly Active for Clonal Inhibition, Differentiation, and Induction of WAF1 in Myeloid Leukemia," Blood, (Sep. 15, 1996), vol. 88, No. 6, pp. 2201-2209.

Non-Final Office Action for U.S. Appl. No. 13/069,074 mailed on Mar. 6, 2013, 21 pp.

Rebel, Vivienne I. et al., "Monocytic Differentiation Induction of HL-60 Cells by MC 903, a Novel Vitamin D Analogue," Leukemia Research, (1992), vol. 16, No. 5, pp. 443-451.

Shiraki, Masataka et al., "Long-Term Treatment of Postmenopausal Osteoporosis with Active Vitamin D3, 1-α-Hydroxycholecalciferol (1α-OHD3) and 1,24 Dihydroxycholecalciferol (1,24(OH)2D3)," Endocrinol. Japon., (Apr. 1985), 32(2), pp. 305-315.

\* cited by examiner

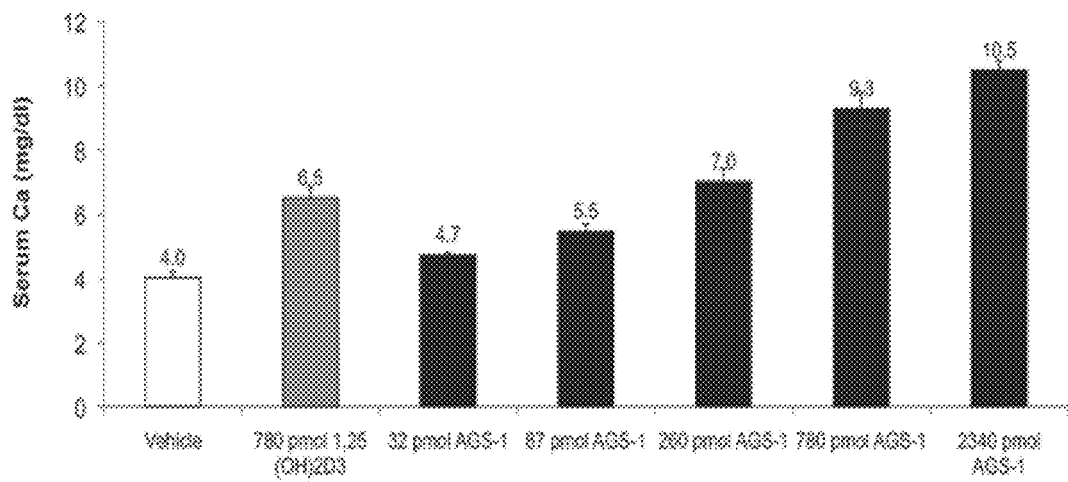
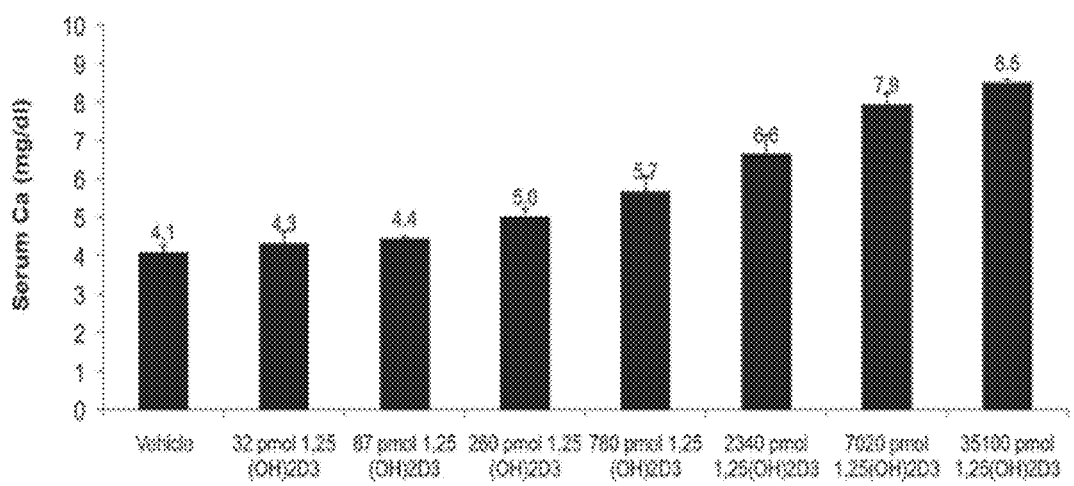

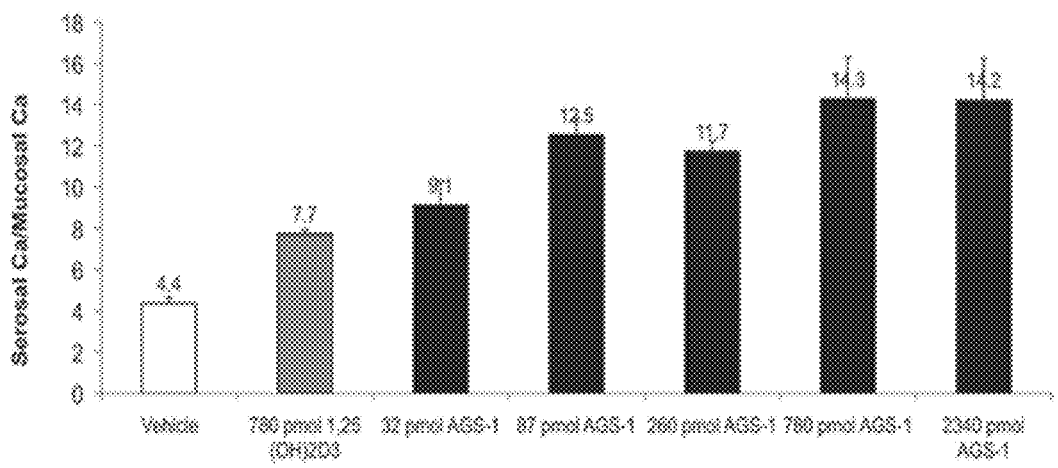

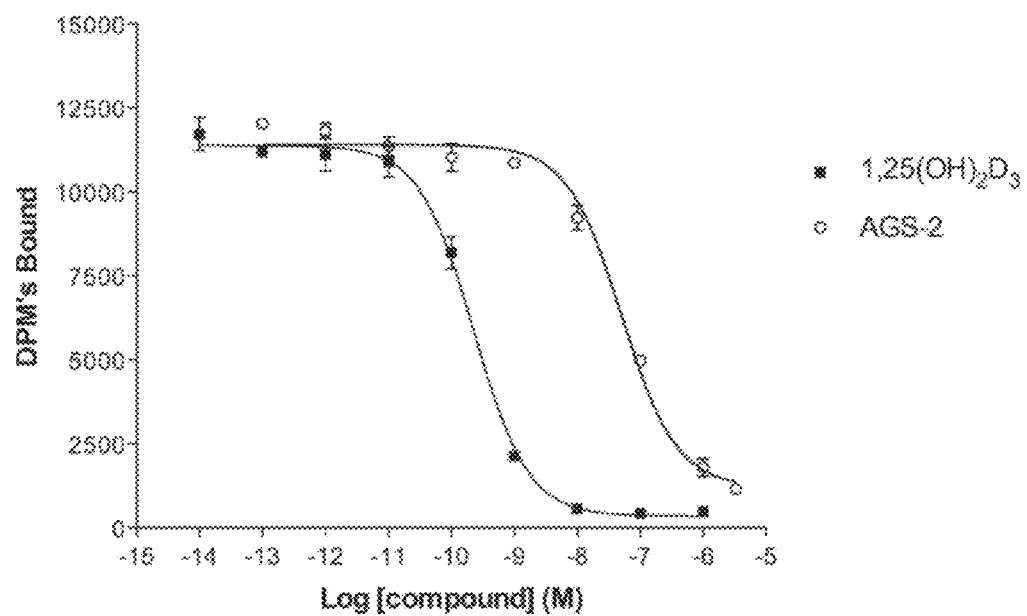

DIASTEREOMERS OF 2-METHYLENE-19-NOR-22-METHYL-1α,25-DIHYDROXYVITAMIN D₃

CROSS-REFERENCE TO RELATED APPLICATIONS

This application is a continuation-in-part of U.S. patent application Ser. No. 13/069,074 filed Mar. 22, 2011, which in turn claims priority to U.S. Provisional Application No. 61/316,653 filed Mar. 23, 2010, the entire disclosure of which is hereby incorporated by reference and for all purposes in its entirety as if fully set forth herein.

STATEMENT OF GOVERNMENT RIGHTS

This invention was made with government support under GM055513 awarded by the National Institutes of Health. The government has certain rights in this invention.

FIELD

This present technology relates to vitamin D compounds, and more particularly to diastereomers of 2-methylene-19-nor-22-methyl-1α,25-dihydroxyvitamin $D_3$ and derivatives thereof and to pharmaceutical formulations that include this compound. The present technology also relates to the use of these compounds in the treatment of various diseases and in the preparation of medicaments for use in treating various diseases.

BACKGROUND

The natural hormone, 1α,25-dihydroxyvitamin $D_3$ (also referred to as 1α,25-dihydroxycholecalciferol and calcitriol and its analog in the ergosterol series, i.e., 1α,25-dihydroxyvitamin $D_2$, are known to be highly potent regulators of calcium homeostasis in animals and humans, and their activity in cellular differentiation has also been established, Ostrem et al., *Proc. Natl. Acad. Set USA*, 84, 2610 (1987). Many structural analogs of these metabolites have been prepared and tested, including 1α-hydroxyvitamin $D_3$, 1α-hydroxyvitamin $D_2$, various side chain homologated vitamins, and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies. The structure of 1α,25-dihydroxyvitamin $D_3$ and the numbering system used to denote the carbon atoms in this compound are shown below.

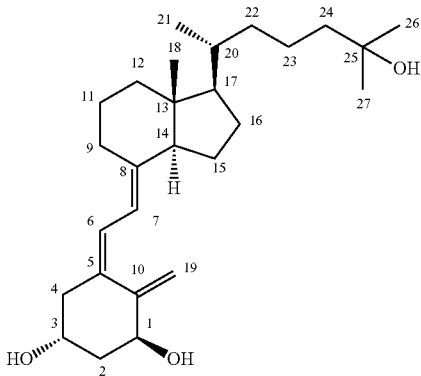

1α,25-Dihydroxyvitamin $D_3$ = 1α,25-Dihydroxycholecalciferol = Calcitriol

SUMMARY

The present technology provides diastereomers of 2-methylene-19-nor-22-methyl-1α,25-dihydroxyvitamin $D_3$, including, for example, (20S,22R)-2-methylene-19-nor-22-methyl-1α,25-dihydroxyvitamin $D_3$, (20S,22S)-2-methylene-19-nor-22-methyl-1α,25-dihydroxyvitamin $D_3$, (20R,22R)-2-methylene-19-nor-22-methyl-1α,25-dihydroxyvitamin $D_3$, (20R,22S)-2-methylene-19-nor-22-methyl-1α,25-dihydroxyvitamin $D_3$, and related compounds, pharmaceutical formulations that include a diastereomer of 2-methylene-19-nor-22-methyl-1α,25-dihydroxyvitamin $D_3$, methods of treating various disease states using these compounds, and the use of these compounds in the preparation of medicaments for treating various disease states.

Therefore, in one aspect, the present technology provides a compound having the formula I shown below

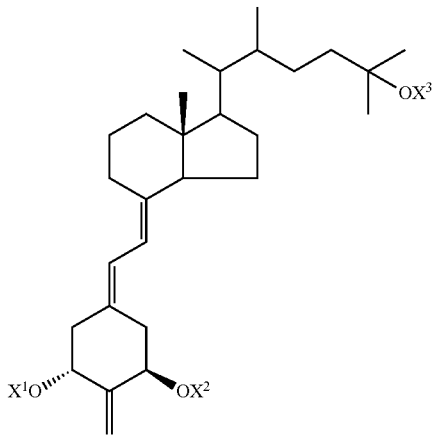

I where $X^1$, $X^2$, and $X^3$ may be the same or different and are independently selected from H or hydroxy-protecting groups. In some embodiments, the carbon at position 20 has the S configuration and the carbon at position 22 has the R configuration as shown in the compound of formula IA. In other embodiments the carbon at position 20 has the S configuration and the carbon at position 22 has the S configuration as shown in the compound IB. In other embodiments the carbon at position 20 has the R configuration and the carbon at position 22 has the S configuration as shown in the compound IC. In other embodiments the carbon at position 20 has the R configuration and the carbon at position 22 has the R configuration as shown in the compound ID.

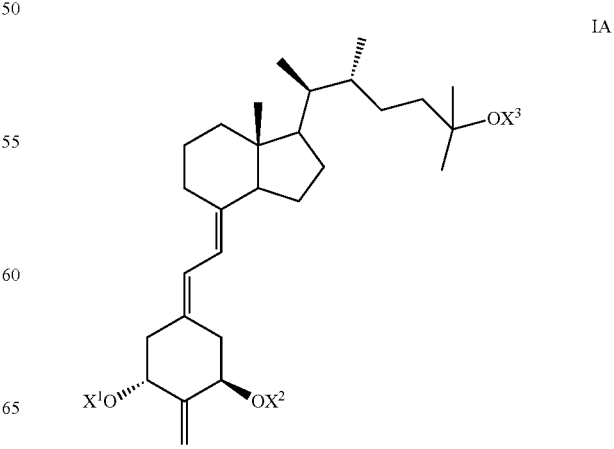

IA

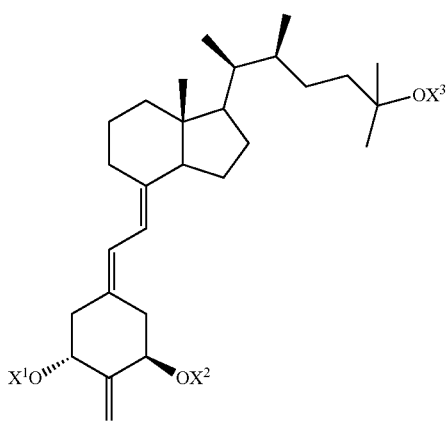

IB

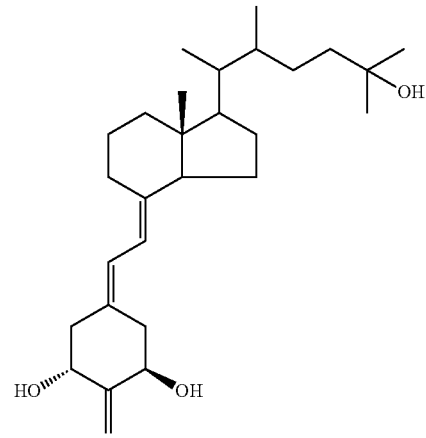

II

In some embodiments, the compound is (20S,22R)-2-methylene-19-nor-22-methyl-1α,25-dihydroxyvitamin $D_3$ and has the formula IIA as shown below, (20S,22S)-2-methylene-19-nor-22-methyl-1α,25-dihydroxyvitamin $D_3$ and has the formula IIB as shown below, (20R,22S)-2-methylene-19-nor-22-methyl-1α,25-dihydroxyvitamin $D_3$ and has the formula IIC as shown below, or (20R,22R)-2-methylene-19-nor-22-methyl-1α,25-dihydroxyvitamin $D_3$ and has the formula IID as shown below:

IC

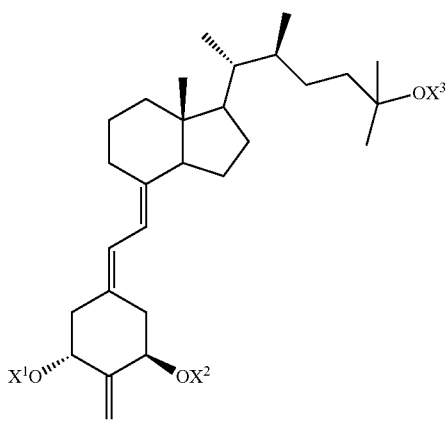

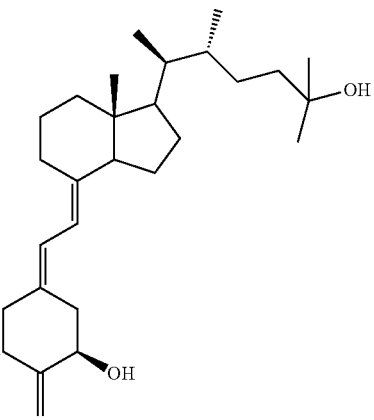

IIA

ID

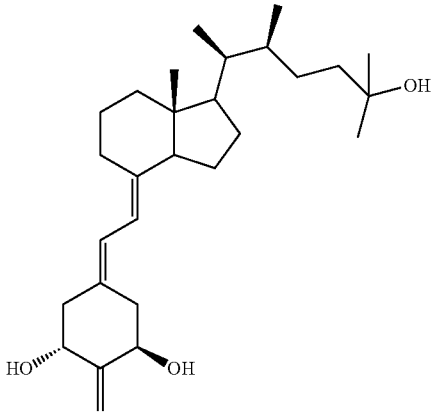

IIB

In some embodiments, $X^1$, $X^2$, and $X^3$ are hydroxy protecting groups such as silyl groups. In some such embodiments, $X^1$ and $X^2$ are both t-butyldimethylsilyl groups and $X^3$ is a triethylsilyl group. In other embodiments, $X^1$, $X^2$, and $X^3$ are H such that the compound has the formula II:

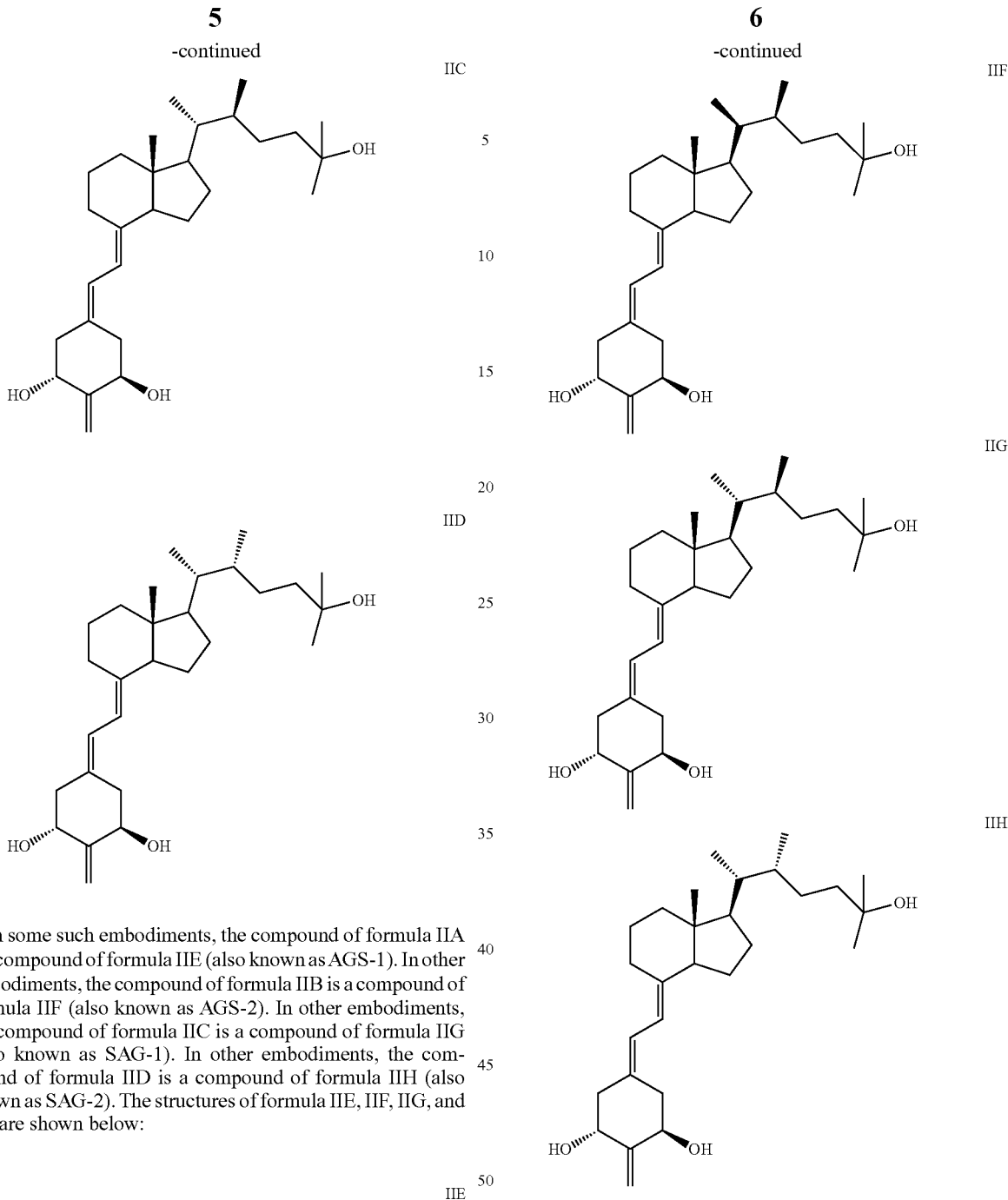

In some such embodiments, the compound of formula IIA is a compound of formula IIE (also known as AGS-1). In other embodiments, the compound of formula IIB is a compound of formula IIF (also known as AGS-2). In other embodiments, the compound of formula IIC is a compound of formula IIG (also known as SAG-1). In other embodiments, the compound of formula IID is a compound of formula IIH (also known as SAG-2). The structures of formula IIE, IIF, IIG, and IIH are shown below:

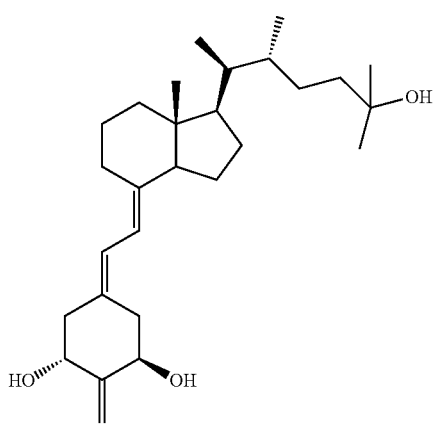

Compounds of the present technology show a highly advantageous pattern of biological activity, including strong binding to the vitamin D receptor and induction of 24-hydroxylase activity. Thus the present compounds may be used in methods of treating a subject suffering from certain biological conditions. The methods include administering an effective amount of a compound of the present technology to the subject, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis.

A compound of the present technology may be present in a composition to treat the above-noted diseases and disorders in an effective amount and optionally including a pharmaceutically acceptable carrier. In some embodiments, the amount of compound includes from about 0.01 μg per gram of composition to about 1 mg per gram of the composition, preferably from about 0.1 μg per gram to about 500 μg per gram of the composition, and may be administered topically, transdermally, orally, or parenterally in dosages of from about 0.01 μg per day to about 1 mg per day, preferably from about 0.1 μg per day to about 500 μg per day.

In another aspect there are provided synthetic intermediates for making compounds of Formulae I and II. Thus, the present technology includes compounds of Formula III:

III

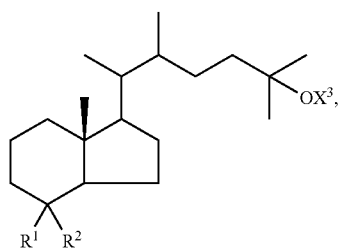

wherein $X^3$ is H or a hydroxyl protecting group, and $R^1$ is OH and $R^2$ is H, or $R^1$ and $R^2$ together are an oxo group (=O). In some embodiments, the compound of Formula III is a compound of Formulae IIIA, IIIB, IIIC or IIID:

IIIA

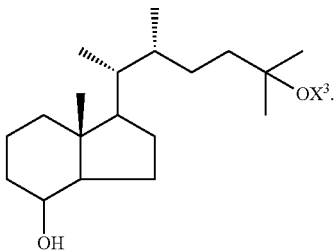

IIIB

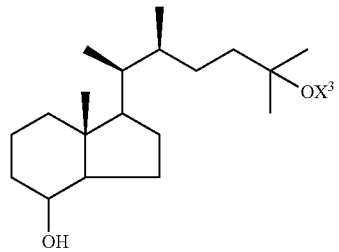

IIIC

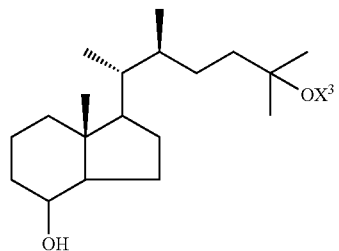

IIID

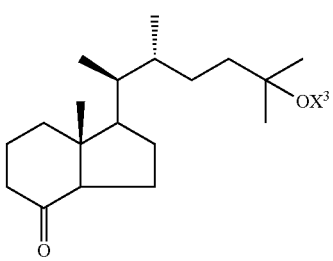

In some embodiments, the compound of Formula III is a compound of Formula IIIE, IIIF, IIIG or IIIH.

IIIE

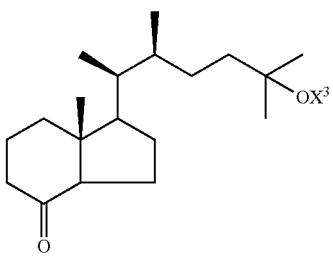

IIIF

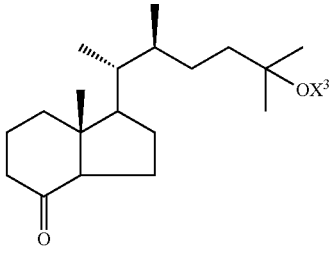

IIIG

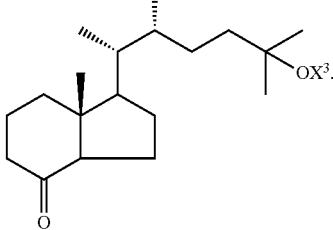

IIIH

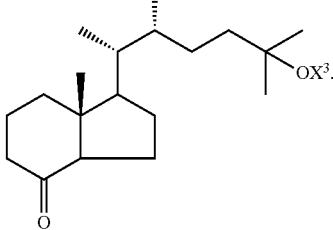

In some embodiments of compounds of Formula III (including, e.g., compounds of Formulae IIIA, IIIB, IIIC, IIID, IIIE, IIIF, IIIG, and IIIH), $X^3$ is a hydroxy protecting group such as a silyl group. In some embodiments, $X^3$ is a triethylsilyl group. In other embodiments, $X^3$ is H. In some embodiments where $X^3$ is H, the compound is crystalline. In still other embodiments, the carbon at position 17 has the S configuration or the R configuration.

Further features and advantages of the present technology will be apparent from the following detailed description and drawings.

BRIEF DESCRIPTION OF THE DRAWINGS

FIGS. 1-4 illustrate various biological activities of (20S,22R)-2-methylene-19-nor-22-methyl-1α,25-dihydroxyvitamin $D_3$ (referred to as "AGS-1" in the Figures), compared with those of the native hormone, 1α,25-dihydroxyvitamin $D_3$ (referred to as "1,25(OH)$_2$D$_3$" in the Figures). FIGS. 5-8 illustrate various biological activities of (20S,22S)-2-methylene-19-nor-22-methyl-1α,25-dihydroxyvitamin $D_3$ (referred to as "AGS-2" in the Figures) compared with those of the native hormone. FIGS. 9-12 illustrate various biological activities of (20R,22S)-2-methylene-19-nor-22-methyl-1α,25-dihydroxyvitamin $D_3$ (referred to as "SAG-1" in the Figures), compared with those of the native hormone. FIGS. 13-16 illustrate various biological activities of (20R,22R)-2-methylene-19-nor-22-methyl-1α,25-dihydroxyvitamin $D_3$ (referred to as "SAG-2" in the Figures), compared with those of the native hormone.

FIG. 1 shows a graph of competitive binding to the nuclear vitamin D hormone receptor between AGS-1 and the native hormone, 1,25(OH)$_2$D$_3$. AGS-1 binds to the nuclear vitamin D receptor with the same affinity as 1,25(OH)$_2$D$_3$.

FIG. 2 is a graph comparing the percent HL-60 cell differentiation as a function of the concentration of AGS-1 with that of 1,25(OH)$_2$D$_3$. AGS-1 is 300 times more potent as the native hormone in causing the differentiation of HL-60 cells into monocytes.

FIG. 3 is a graph comparing the in vitro transcription activity of AGS-1 with that of 1,25(OH)$_2$D$_3$. In bone cells, AGS-1 is nearly 40 times more potent than 1,25(OH)$_2$D$_3$ in increasing transcription of the 24-hydroxylase gene.

FIG. 4A and FIG. 4B are bar graphs comparing the bone calcium mobilization activity of AGS-1 with that of 1,25(OH)$_2$D$_3$ in rat. AGS-1 is both more efficacious and about 10 to 50 times more potent than the native hormone in releasing bone calcium stores. FIG. 4C is a bar graph comparing the intestinal calcium transport activity of AGS-1 with that of 1,25(OH)$_2$D$_3$. AGS-1 exhibits higher potency in promoting intestinal calcium transport than the native hormone.

FIG. 5 shows a graph of competitive binding to the nuclear vitamin D hormone receptor between AGS-2 and the native hormone, 1,25(OH)$_2$D$_3$. AGS-2 binds to the nuclear vitamin D receptor with lower affinity than 1,25(OH)$_2$D$_3$.

FIG. 6 is a graph comparing the percent HL-60 cell differentiation as a function of the concentration of AGS-2 with that of 1,25(OH)$_2$D$_3$. AGS-2 is approximately 10 times less potent than the native hormone in causing die differentiation of HL-60 cells into monocytes.

FIG. 7 is a graph comparing the in vitro transcription activity of AGS-2 with that of 1,25(OH)$_2$D$_3$ in rat osteosarcoma cells. AGS-2 is about 10 times less potent than 1,25(OH)$_2$D$_3$ in increasing transcription of the 24-hydroxylase gene.

FIG. 9 shows a graph of competitive binding to the nuclear vitamin D hormone receptor between SAG-1 and the native hormone, 1,25(OH)$_2$D$_3$. SAG-1 binds to the nuclear vitamin D receptor with similar or slightly less affinity than 1,25(OH)$_2$D$_3$.

FIG. 10 is a graph comparing the percent HL-60 cell differentiation as a function of the concentration of SAG-1 with that of 1,25(OH)$_2$D$_3$. SAG-1 is more than 3 times more potent than the native hormone in causing the differentiation of HL-60 cells into monocytes.

FIG. 11 is a graph comparing the in vitro transcription activity of SAG-1 with that of 1,25(OH)$_2$D$_3$. In bone cells, SAG-1 is approximately equal in potency to 1,25(OH)$_2$D$_3$ in increasing transcription of the 24-hydroxylase gene.

FIG. 13 shows a graph of competitive binding to the nuclear vitamin D hormone receptor between SAG-2 and the native hormone, 1,25(OH)$_2$D$_3$. SAG-2 binds to die nuclear vitamin D receptor with approximately 4 times less affinity than 1,25(OH)$_2$D$_3$.

FIG. 14 is a graph comparing the percent HL-60 cell differentiation as a function of the concentration of SAG-2 with that of 1,25(OH)$_2$D$_3$. SAG-2 is approximately 3 times less potent than the native hormone in causing the differentiation of HL-60 cells into monocytes.

FIG. 15 is a graph comparing the in vitro transcription activity of SAG-2 with that of 1,25(OH)$_2$D$_3$, in rat osteosarcoma cells. SAG-2 is about 20 times less potent than 1,25(OH)$_2$D$_3$ in increasing transcription of the 24-hydroxylase gene.

Figure 1:
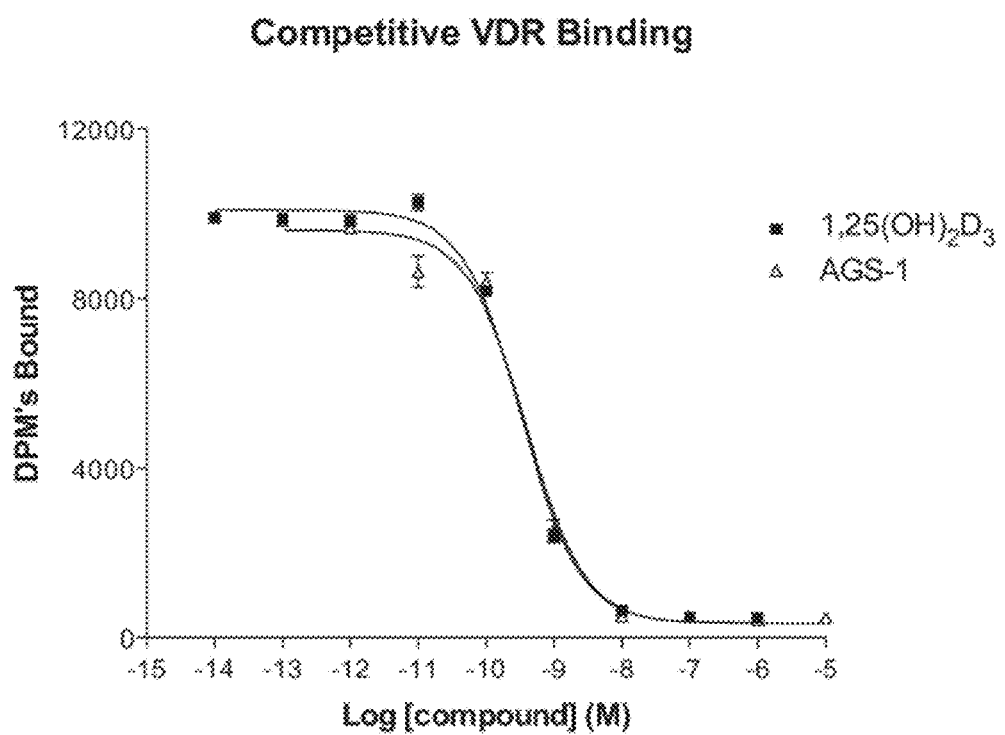

DETAILED DESCRIPTION (20S,22R)-2-methylene-19-nor-22-methyl-1α,25-dihydroxyvitamin $D_3$, (20S,22S)-2-methylene-19-nor-22-methyl-1α,25-dihydroxyvitamin $D_3$, (20R,22S)-2-methylene-19-nor-22-methyl-1α,25-dihydroxyvitamin $D_3$, and (20R,22R)-2-methylene-19-nor-22-methyl-1α,25-dihydroxyvitamin $D_3$, were synthesized, and tested, and found to be useful in treating a variety of biological conditions as described herein. Structurally, these compounds have the formulas IIA, IIB, IIC, and IID as shown below:

IIA

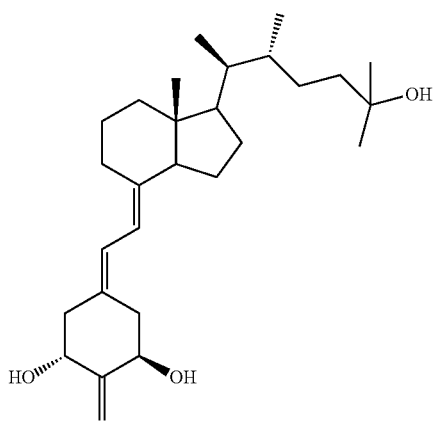

IIB

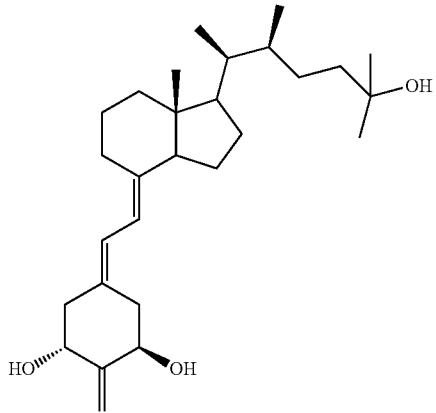

IIC

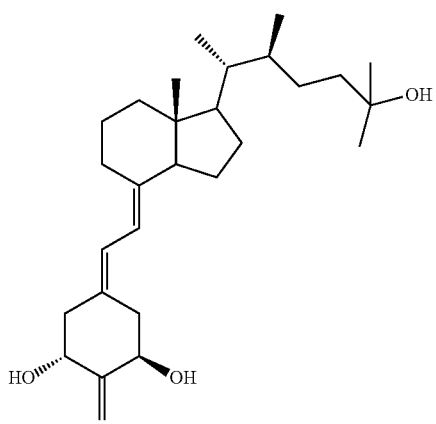

IID

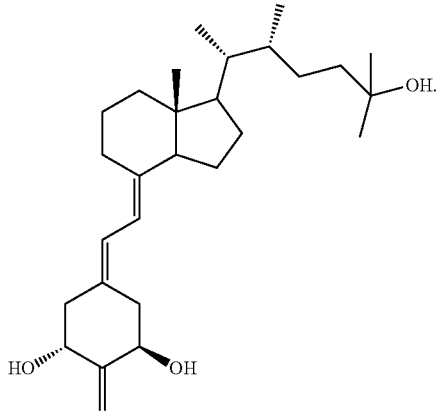

In some such embodiments, the compound of formula IIA is a compound of formula IIE, in other embodiments, the compound of formula IIB is a compound of formula IIF and have the structures shown below:

IIE

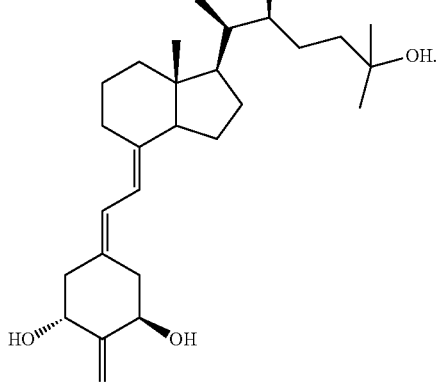

IIF

In other such embodiments, the compound of formula IIC is a compound of formula IIG, in other embodiments, the compound of formula IID is a compound of formula IIH and have the structures shown below:

IIG

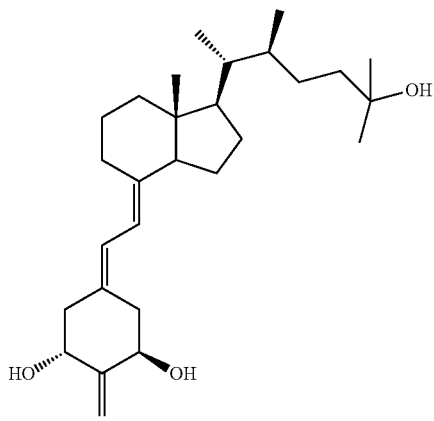

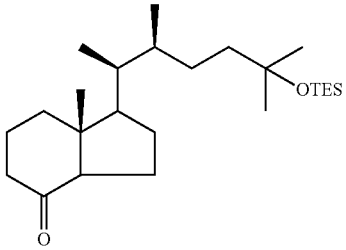
IIIFA

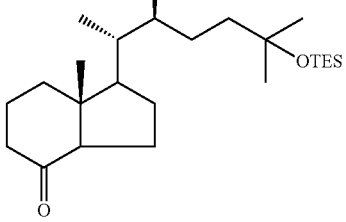
IIIGA

IIH

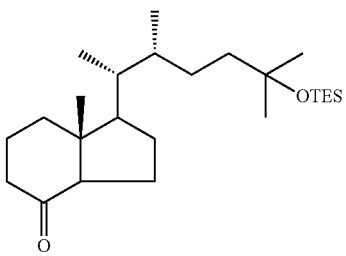
IIIHA

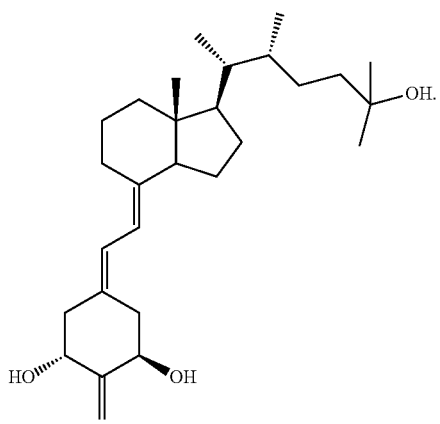

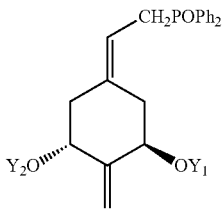
IV

Preparation of (20S,22R)-2-methylene-19-nor-22-methyl-1α,25-dihydroxyvitamin D$_3$, (20S,22S)-2-methylene-19-nor-22-methyl-1α,25-dihydroxy vitamin D$_3$, (20R,22S)-2-methylene-19-nor-22-methyl-1α,25-dihydroxyvitamin D$_3$, and (20R,22R))-2-methylene-19-nor-22-methyl-1α,25-dihydroxyvitamin D$_3$ can be accomplished by condensing an appropriate bicyclic Windaus-Grundmann type ketone (II-IEA, IIIFA, IIIGA, or IIIHA) with the allylic phosphine oxide IV followed by deprotection (removal of the Y$_1$ and Y$_2$ groups).

IIIEA

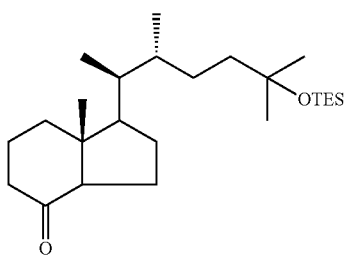

Hydraindanones of structure IIIEA, IIIFA, IIIGA, or IIIHA can prepared by slight modification known methods as will be readily apparent to one of skill in the art and described herein. Specific examples of some important bicyclic ketones used to synthesize vitamin D analogs are those described in Mincione et al., *Synth. Commun* 19, 723, (1989); and Peterson et al., *J. Org. Chem.* 51, 1948, (1986). An overall process for synthesizing 2-alkylidene-19-nor-vitamin D compounds is illustrated and described in U.S. Pat. No. 5,843,928, which is hereby incorporated by reference in its entirety and for all purposes as if fully set forth herein. Details of preparing hydraindanones IIIEA, IIIFA, IIIGA, and IIIHA are found in the Examples herein.

In phosphine oxide IV, Y$_1$ and Y$_2$ are hydroxy-protecting groups such as silyl protecting groups. The t-butyldimethylsilyl (TBDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans, I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S.

Pat. No. 5,536,713; and DeLuca et al., U.S. Pat. No. 5,843,928, all of which are hereby incorporated by reference in their entirety and for all purposes as if fully set forth herein).

Phosphine oxide IV is a convenient reagent that may be prepared according to the procedures described by Sicinski et al., *J. Med. Chem.*, 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scheme 1 shows the general procedure for synthesizing phosphine oxide IV as outlined in U.S. Pat. No. 5,843,928 which is hereby incorporated by reference in its entirety as if fully set forth herein.

silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999), which can be added or removed using the procedures set forth therein, and which is hereby incorporated by reference in its entirety and for all purposes as if fully set forth herein.

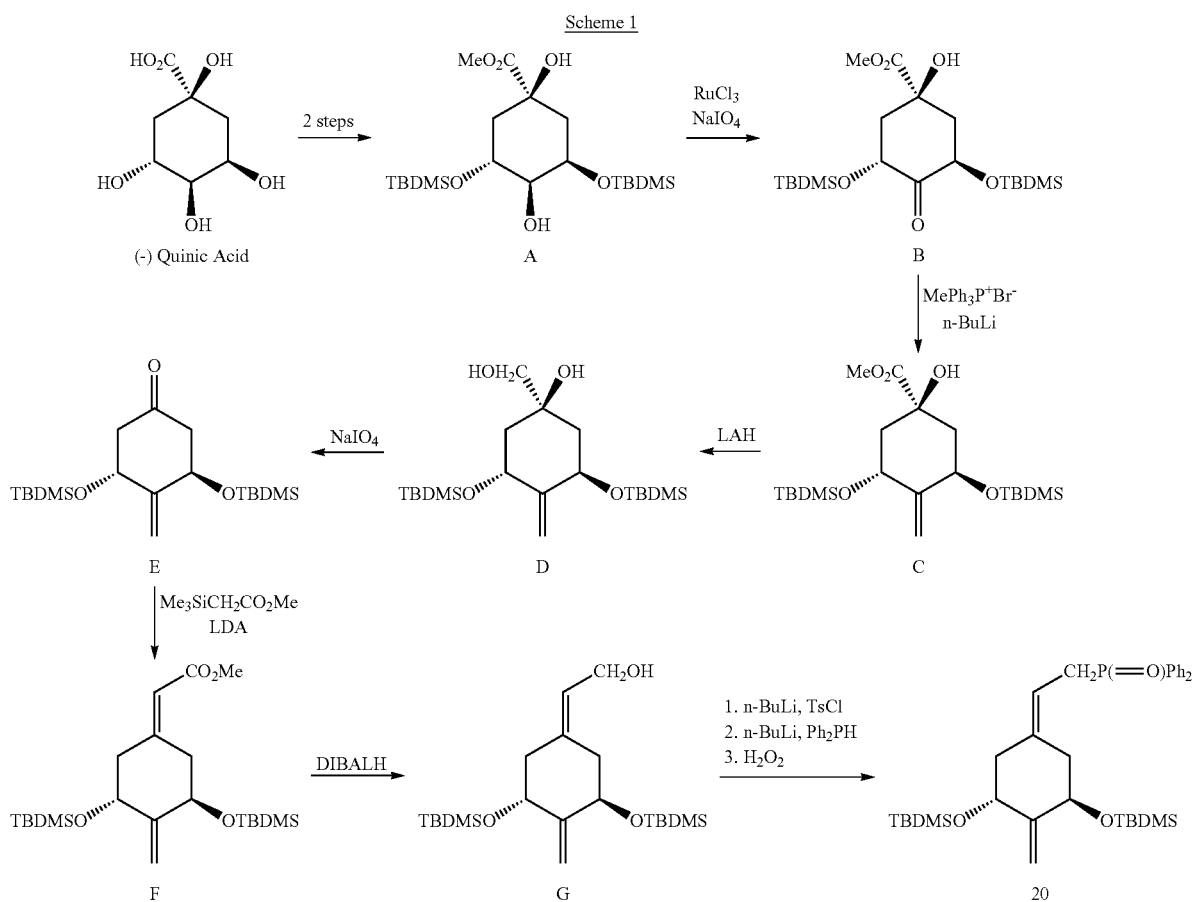

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

Figure 12A:
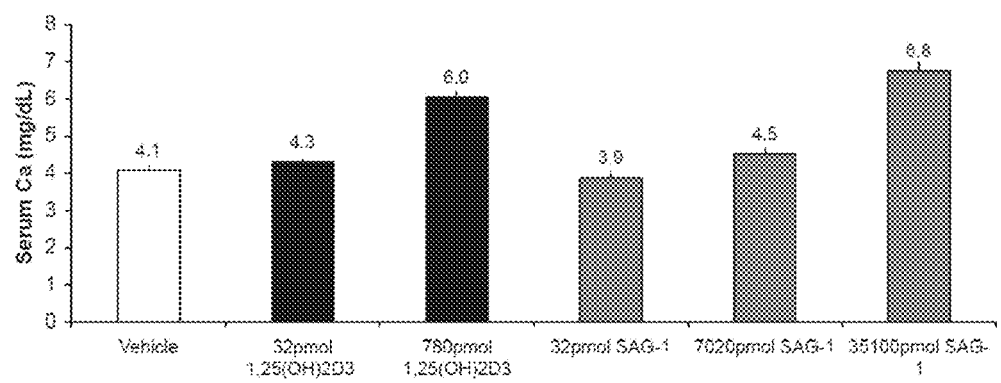
FIG. 12A and FIG. 12B are bar graphs comparing the bone calcium mobilization activity of SAG-1 with that of 1,25(OH)$_2$D$_3$ in rat. SAG-1 is less potent than the native hormone in releasing bone calcium stores.
Figure 12B:
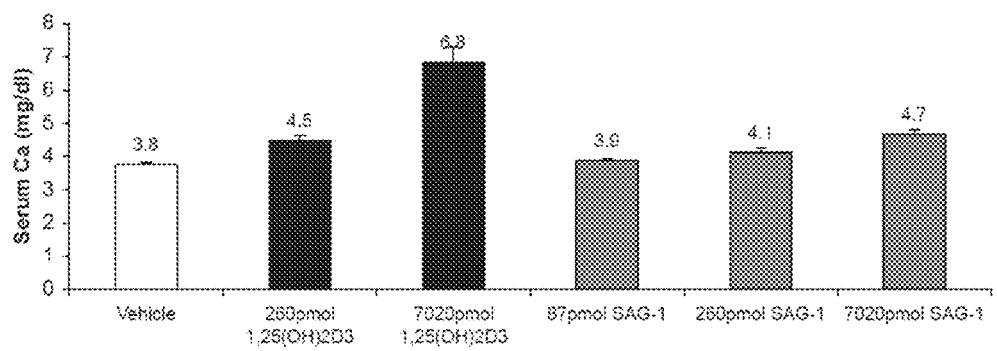
Figure 15:
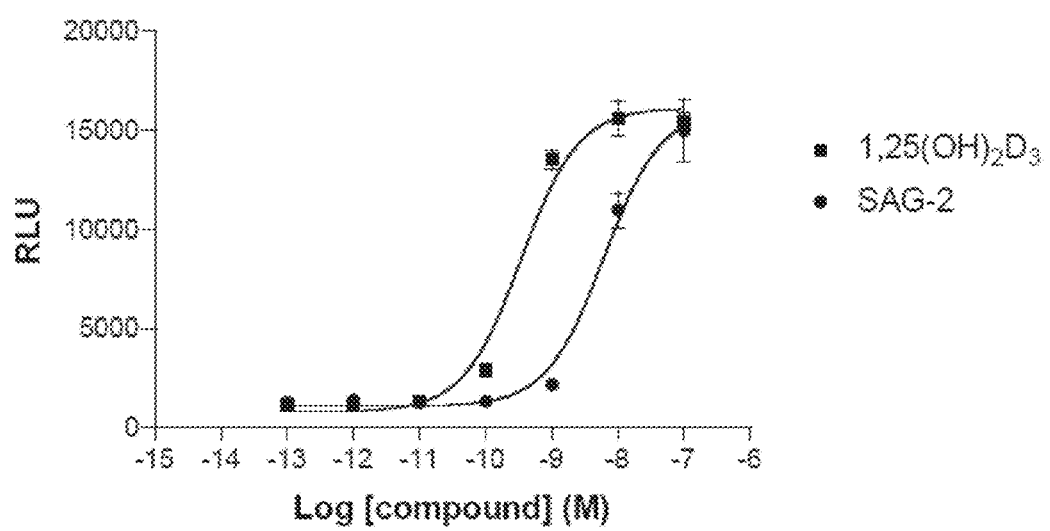
Figure 16A:
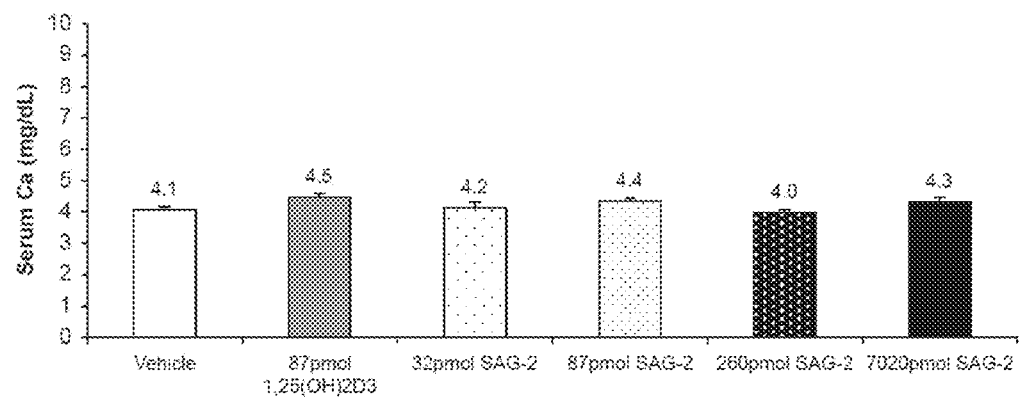
FIG. 16A and FIG. 16B are bar graphs comparing the bone calcium mobilization activity of SAG-2 with that of 1,25(OH)$_2$D$_3$ in rat. SAG-2 has very little to no activity in mobilizing calcium from bone stores.
Figure 16B:
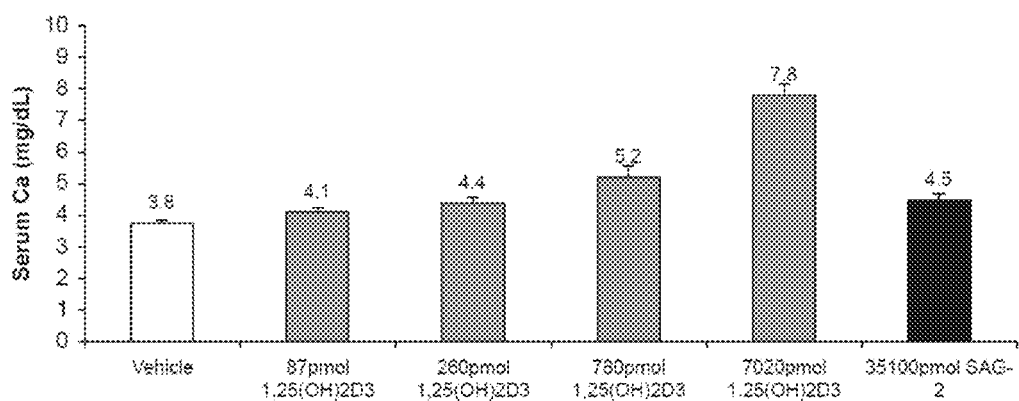

The compounds of the present technology show significant biological activity. AGS-1, AGS-2, SAG-1, and SAG-2 all bind the vitamin D receptor. In addition, both AGS-1, AGS-2, and SAG-1 exhibit relatively high cell differentiation activity and AGS-1 and AGS-2 exhibit relatively high 24-hydroxylase transcription activity. The 24-hydroxylase transcription activity of SAG-II was unexpectedly low in comparison to the native hormone, 1,25(OH)$_2$D$_3$ (FIG. 15). The calcemic activity profiles of the four compounds differ. AGS-1 displays significantly higher bone calcium mobilization activity and intestinal calcium transport activity than 1,25(OH)$_2$D$_3$ (See FIGS. 4A-4C). By contrast, AGS-2 shows essentially no ability to mobilize bone calcium except at extremely high concentrations, but comparable or slightly higher intestinal calcium transport compared to $1,25(OH)_2D_3$ (See FIGS. 8A and 8B). Like, AGS-2, SAG-1 shows little or no ability to mobilize bone calcium except at extremely high doses (See FIGS. 12A and 12B). However, in the case of intestinal calcium transport, SAG-1 hows comparable or reduced potency in comparison to $1,25(OH)_2D_3$ at lower concentrations but increased potency in comparison to $1,25(OH)_2D_3$ at high concentrations (See FIGS. 12C and 12D). SAG-2, shows little or no ability to mobilize bone calcium, even at extremely high concentrations (See FIGS. 16A and 16B). In the case of intestinal calcium transport, SAG-2 shows little ability to increase transport, except at extremely high concentrations.

In view of their biological activity, compounds of the present technology may be used for treatment and prophylaxis of human disorders which are characterized by an imbalance in the immune system, e.g., in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the present technology.

In view of the relatively high cell differentiation activity, the present compounds may also be used in the treatment of psoriasis, or as anti-cancer agents, especially against leukemia, colon cancer, breast cancer and prostate cancer. In addition, due to their relatively high cell differentiation activity, these compounds provide a therapeutic agent for the treatment of various skin conditions including wrinkles, lack of adequate dermal hydration, i.e., dry skin, lack of adequate skin firmness, i.e., slack skin, and insufficient sebum secretion. Use of these compounds thus not only results in moisturizing of skin but also improves the barrier function of skin.

In view of its extremely high cell differentiation activity and bone calcium mobilization activity, AGS-1 is especially suited for die treatment of diseases such as psoriasis, osteoporosis, rickets, and renal osteodystrophy. In view of their cell differentiation and intestinal activities, AGS-2 and SAG-1 are especially suited for treatment of intestinal diseases such as IBD, including celiac disease and Crohn's disease. In case of the SAG-1 and SAG-2, these compounds reduced or no calcemic activity generally. Accordingly, SAG-1 and SAG-2 are especially useful in treating diseases where elevation of calcium is undesirable.

The compounds of the present technology may be used to prepare pharmaceutical formulations or medicaments that include a compound of the present technology in combination with a pharmaceutically acceptable carrier. Such pharmaceutical formulations and medicaments may be used to treat various biological disorders such as those described herein. Methods for treating such disorders typically include administering an effective amount of the compound or an appropriate amount of a pharmaceutical formulation or a medicament that includes the compound to a subject suffering from die biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

For treatment purposes, the compounds defined by formula I, II, IIA, IIB, IIC, IID, IIE, IIF, IIG, and IIH may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the present technology. Such excipients and carriers are described, for example, in "Remingtons Pharmaceutical Sciences," Mack Pub. Co., New Jersey (1991), which is hereby incorporated by reference in its entirety and for all purposes as if fully set forth herein.

The compounds may be administered orally, topically, parenterally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 μg to about 1 mg per day of the compound are appropriate for treatment purposes. In some such embodiments, an appropriate and effective dose may range from 0.01 μg to 1 mg per day of the compound. In other such embodiments, an appropriate and effective dose may range from 0.1 μg to 500 μg per day of the compound. Such doses will be adjusted according to the type of disease or condition to be treated, the severity of the disease or condition, and the response of the subject as is well understood in the art. The compound may be suitably administered alone, or together with another active vitamin D compound.

Compositions for use in the present technology include an effective amount of compound I, II, IIA, IIB, IIC, IID, IIE, IIF, IIG, or IIH as the active ingredient, and a suitable carrier. An effective amount of the compound for use in accordance with some embodiments of the present technology will generally be a dosage amount such as those described herein, and may be administered topically, transdermally, orally, nasally, rectally, or parenterally.

The compound of formula I, II, IIA, IIB, IIC, IID, IIE, IIF, IIG, and IIH may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The compound may be formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present technology comprise an active ingredient in association with a pharmaceutically acceptable carrier and, optionally, other therapeutic ingredients. The carrier must be "acceptable" in the sense of being compatible with the other ingredients of the formulations and not deleterious to the recipient thereof.

Formulations of the present technology suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entirety and for all purposes as if fully set forth herein.

The present technology is further illustrated by the following examples, which should not be construed as limiting in any way.

EXAMPLES

Example 1A

Synthesis of (20S,22S)-2-methylene-19-nor-22-methyl-1α,25-dihydroxyvitamin $D_3$ and (20S,22R)-2-methylene-19-nor-22-methyl-1α,25-dihydroxyvitamin $D_3$ Compounds of formula I, formula II, formula IIA and formula IIB were prepared using the methods shown in Schemes 2 and 3. As shown in Scheme 2, compound 2 was obtained by ozonolysis of vitamin $D_2$ (1) as described by Sicinski et al. (J. Med. Chem. 41, 4662-4672, 1998), followed by reduction with borohydride. Treatment of the dialcohol 2 with tosyl chloride in pyridine provided the tosyl protected compound 3. Compound 3 was reacted with triethylsilyl trifluoromethanesulfonate and 2,6-lutidine in dichloromethane to yield compound 4, Compound 4 was treated with sodium bicarbonate in DMSO to oxidize the tosyl protected alcohol group to an aldehyde compound 5, Compound 5 was racemized at position 20 by treatment with tetrabutylammonium hydroxide and the resulting compound 6 was reduced with sodium borohydride to give pure isomer 7 along with a mixture of both isomers 7 and 8. The isolated isomer 7 was then protected with tosyl chloride in pyridine and the tosyl protected alcohol 9 was converted to cyanide 10 by reacting it with sodium cyanide in DMSO. The cyano compound 10 was then treated with 4-bromo-2-methyl-1-triethylsilyloxy butane (11), in presence of a mixture of n-butyllithium and diisopropylamine, to provide compound 12. The cyano group of compound 12 was converted to the corresponding aldehyde 13 by treating it with diisobutylaluminum hydride in dichloromethane. Aldehyde 13 was then reduced to alcohol 14 using sodium borohydride in methanol. The free hydroxyl group of compound 14 was then reacted with tosyl chloride in pyridine and the resulting tosyl protected compound 15 was reduced to the corresponding alkane 16 using lithium aluminum hydride as the reducing agent. The triethylsilyl protected dihydroxy compound 16 was then deprotected using tetrabutylammonium fluoride in THF and the racemic mixture of diols thus obtained was separated by crystallization from ethyl acetate to provide the two separate isomers, the 22R 17 diol and 22S diol 18. Each of the diols 17 and 18 were then separately oxidized with a using tetrapropylammonium perruthenate in the presence of 4-methylmorpholine oxide to produce the respective ketones. Each ketone was further independently treated with triethylsilyl trifluoromethanesulfonate and 2,6-lutidine in dichloromethane to provide the triethylsilyl protected ketone 22R compound 19A or 22S compound 19B.

Scheme 2

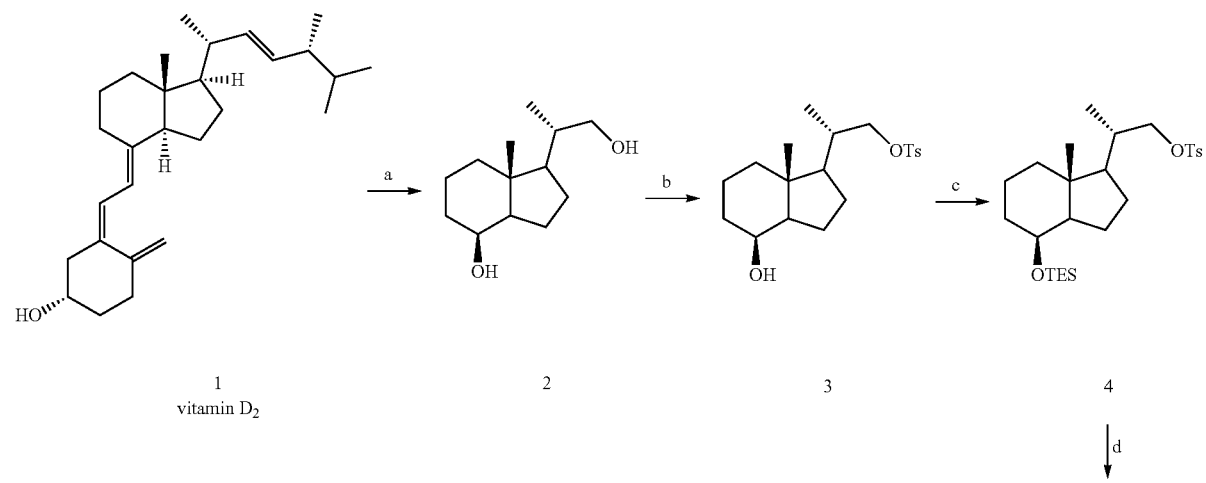

-continued
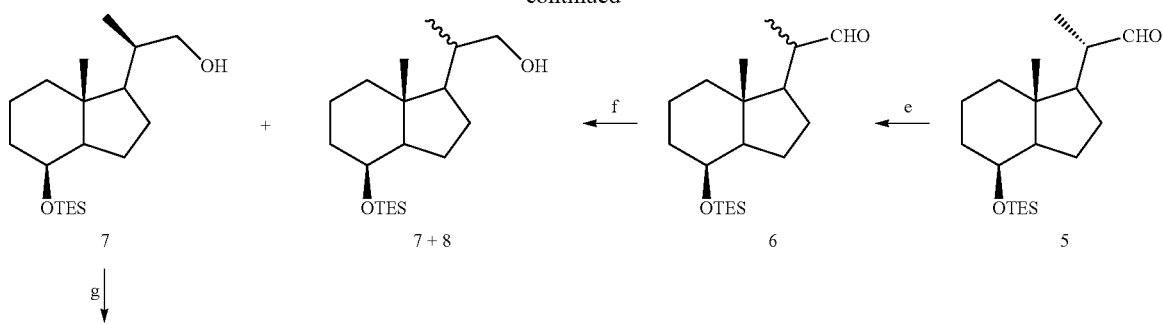
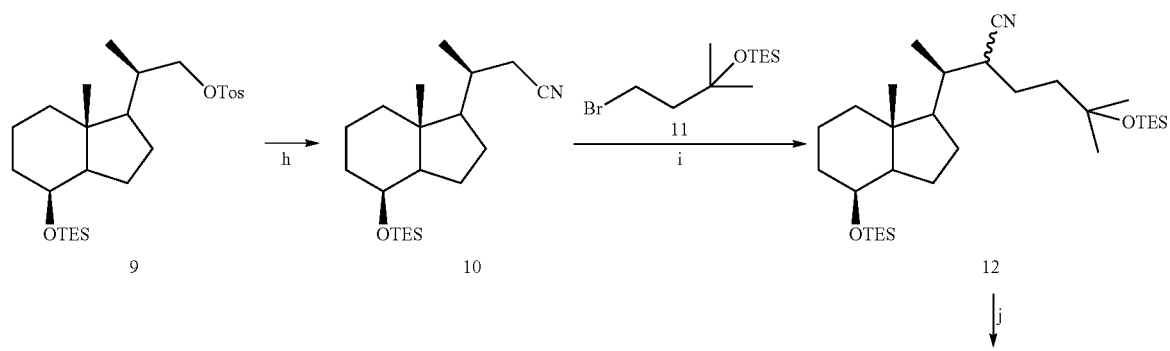
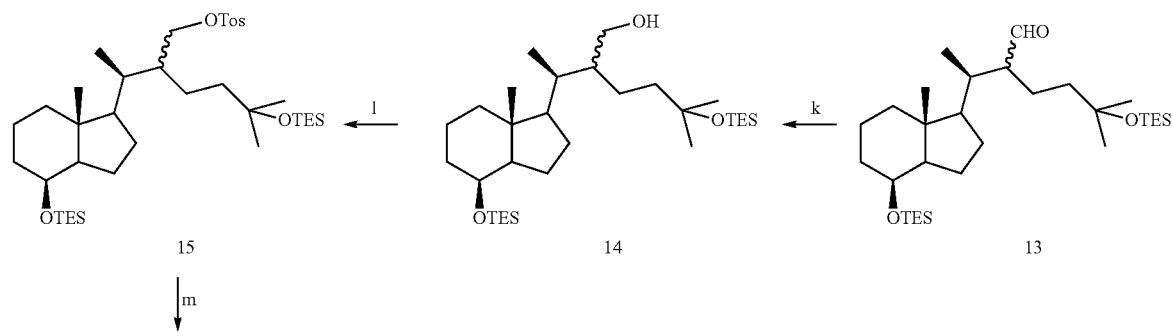
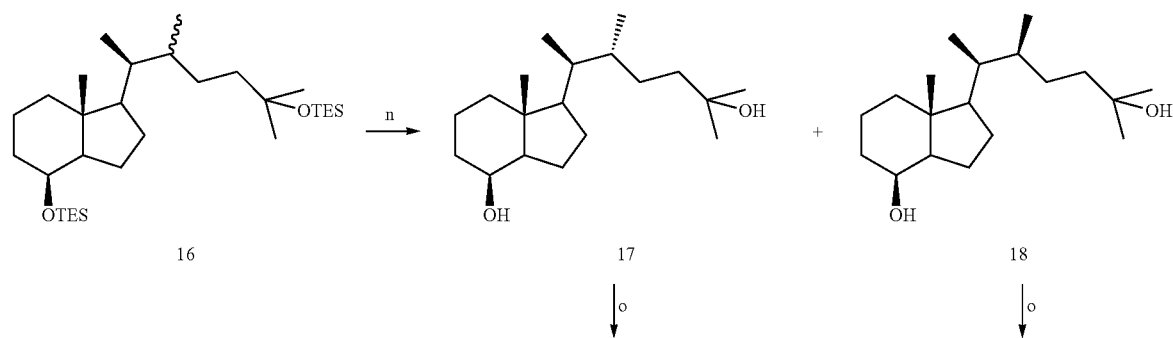

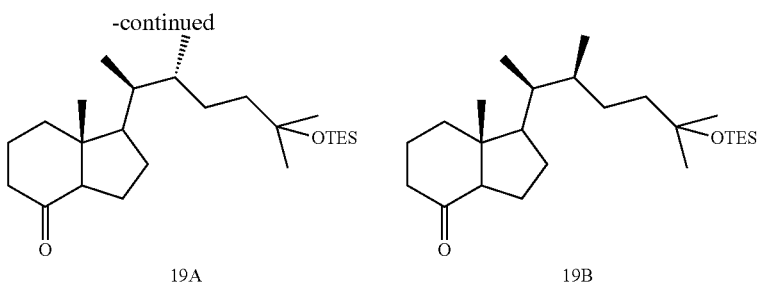

19A      19B

∿∿ indicates that the carbon is in either the R or S configuration.

a) 1. $O_3$, pyridine, MeOH; 2. $NaBH_4$ (2, 49%)
b) TsCl, pyridine (3, 96%)
c) TESOTf, 2,6-lutidine, DCM (4, 99%)
d) $NaHCO_3$, DMSO, EtOAc (5, 76%)
e) 1. TBAOH, $H_2O$, DCM (6, 71%)
f) $NaBH_4$, THF, EtOH (7, 47%)(8, 40%)
g) TosCl, pyridine (9, 89%)
h) NaCN, DMSO (10, 85%)
i) 1. n-BuLi, DIPA, THF; 2. 11 (12, 79%)
j) DIBAL, toluene, DCM (13, 76%)
k) $NaBH_4$, MeOH (14, 70%)
l) TosCl, pyridine (15, 83%)
m) $LiAlH_4$, DEE (16, 75%)
n) 1. TBAF, THF (17 and 18, 99%); 2. Cyrstallization from EtOAc
o) 1. Mol sieves 4Å, 4-MMO, TPAP, DCM; 2. TESOTf, 2,6-lutidine, DCM (19A, 68%) (19B, 73%)

Scheme 3 illustrates the conversion of compounds 19A or 19B to the title compounds IIA or IIB. A Wittig-Horner condensation of the protected Grundmann's Ketone (Compound 19A or 19B) with the phosphine oxide (Compound 20) in the presence of phenyllithium was performed as shown is Scheme 3. The Ring-A phosphine oxide compound 20 was synthesized as shown in Scheme 1 and as previously described. Finally, the target compound (Compound IIA or IIB) was generated by deprotection of hydroxy groups in compounds 21A or 21B in the presence of hydrofluoric acid.

Scheme 3

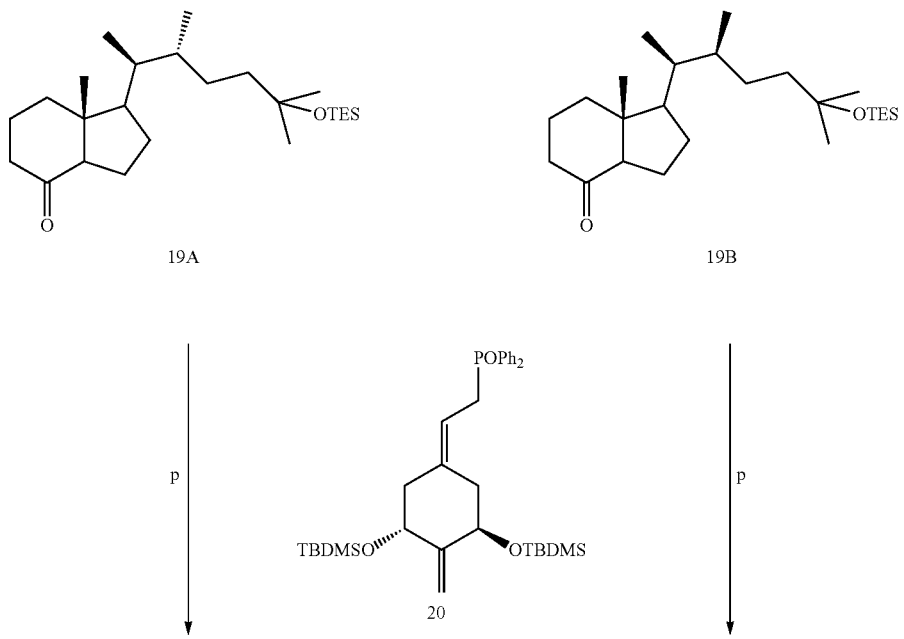

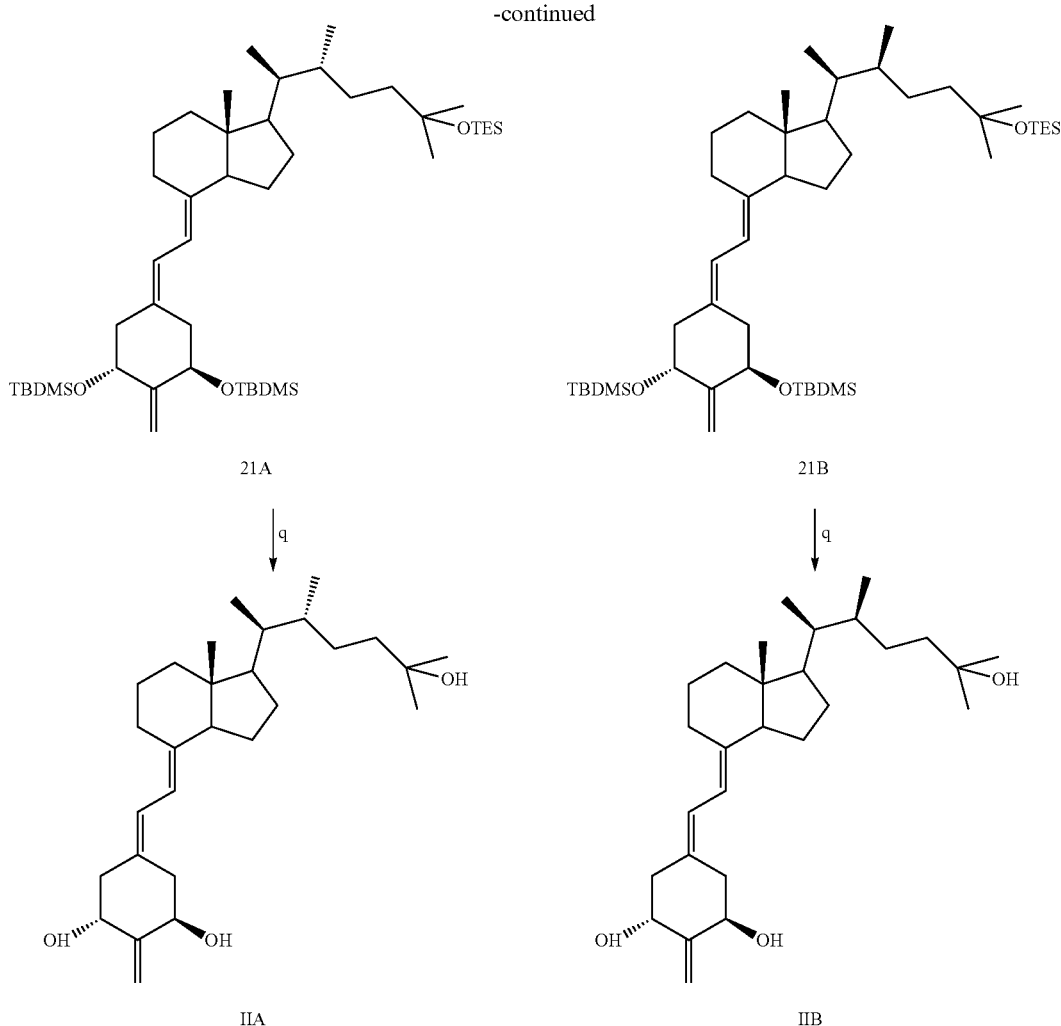

p) PhLi, THF, 20 (21A, 90%) (21B, 87%)
q) HF, MeCN, THF (IIA, 77%) (IIB, 50%)

(8S,20S)-Des-A,B-20-(hydroxymethyl)-pregnan-8-ol (2)

Ozone was passed through a solution of vitamin $D_2$ 1 (5 g, 12.6 mmol) and pyridine (5 mL, 4.89 g, 62 mmol) in methanol (400 mL) at −78° C. When the reaction mixture turned deep blue it was flushed with oxygen for 15 min to remove the residual ozone and then it was treated with $NaBH_4$ (1.5 g, 40 mmol). After 15 min the second portion of $NaBH_4$ (1.5 g, 40 mmol) was added and the mixture was allowed to warm to room temperature. The third portion of $NaBH_4$ (1.5 g, 40 mmol) was added and the reaction mixture was stirred for 18 hours. The reaction was quenched with water, concentrated under reduced pressure and extracted with dichloromethane. The combined organic phases were washed with 1M aqueous HCl, saturated aqueous $NaHCO_3$ and dried ($Na_2SO_4$) and concentrated. The residue was purified by column chromatography on silica gel (30%, then 50% ethyl acetate/hexane) to give the diol 2 (2.61 g, 49%) as colorless crystals.

m.p. 107° C. (from ethyl acetate/hexane); $[\alpha]_D$ +32.9 (c 1.0, $CHCl_3$); $^1H$ NMR (500 MHz, $CDCl_3$) δ 4.07 (1H, d, J=2.5 Hz), 3.62 (1H, dd, J=10.5, 3.2 Hz), 3.37 (1H, dd, J=10.5, 6.8 Hz), 1.98 (1H, m), 1.80 (3H, m), 1.02 (3H, d, J=6.6 Hz), 0.94 (3H, s); $^{13}C$ NMR (125 MHz, $CDCl_3$) δ 69.21, 67.81, 52.91, 52.34, 41.84, 40.20, 38.22, 33.55, 26.64, 22.55, 17.38, 16.60, 13.56; MS (EI) m/z 212 (1, $M^+$), 194 (28, $M^+$-$H_2O$), 179 (29), 163 (22), 147 (15), 135 (42), 125 (48), 111 (100), 97 (51); exact mass calculated for $C_{13}H_{22}O$ ($M^+$-$H_2O$) 194.1671, found 194.1673.

(8S,20S)-Des-A,B-20-[(p-toluenesulfonyl)oxy]methyl-pregnan-8-ol (3)

A precooled (−20° C.) solution of tosyl chloride (0.9 g, 4.73 mmol) in pyridine (2 mL) was added to a mixture of the diol 2 (0.52 g, 2.45 mmol) in dry pyridine (5 mL) at −20° C. The reaction mixture was stirred for 3 h at −20° C., then it was warmed to 0° C. and stirred for 18 h. The mixture was pulled into a saturated aqueous $CuSO_4$ solution and extracted with dichloromethane. Combined organic phases were washed with a saturated aqueous $CuSO_4$ solution and dried ($Na_2SO_4$) and concentrated. The residue was purified by column chromatography on silica gel (20% ethyl acetate/hexane) to afford of tosylate 3 (0.86 g, 96% yield) as colorless crystals.

m.p. 95° C. (from ethyl acetate/hexane); $[\alpha]_D$+17.4 (c 1.0, $CHCl_3$); $^1H$ NMR (400 MHz, $CDCl_3$) δ7.77 (2H, d, J=8.2

Hz), 7.34 (2H, d, J=8.2 Hz), 4.06 (1H, s), 3.94 (1H, dd, J=9.2, 3.1 Hz), 3.80 (1H, dd, J=9.2, 6.2 Hz), 2.44 (3H, s), 1.90 (1H, m), 1.78 (2H, m), 0.95 (3H, d, J=6.6 Hz), 0.88 (3H, s); $^{13}$C NMR(100 MHz, CDCl$_3$) δ 144.59, 133.01, 129.73, 127.86, 75.56, 68.98, 52.18, 41.81, 40.00, 35.66, 33.50, 26.36, 22.40, 21.60, 17.29, 16.69, 13.43; MS (EI) m/z 367 (6, MH$^+$), 348 (5, M$^+$-H$_2$O), 307 (2), 194 (18), 179 (23), 150 (17), 135 (16), 125 (34), 111 (100), 91 (50); MS (ESI) m/z 389 (100, [M+Na]$^+$), 755 (90, [2M+Na]$^+$), 1121 (60, [3M+Na]$^+$); exact mass calculated for C$_{20}$H$_{30}$O$_4$SNa [M+Na]$^+$ 389.1763, found 389.1758.

(8S,20S)-Des-A,B-8-[(triethylsilyl)oxy]-20-[(p-toluenesulfonyl)oxy]methyl-pregnane (4)

Triethylsilyl trifluoromethanesulfonate (0.6 mL, 0.70 g, 2.65 mmol) was added to a solution of the tosylate 3 (0.65 g, 1.78 mmol) and 2,6-lutidine (0.3 mL, 0.28 g, 2.58 mmol) in dichloromethane (6 mL) at 0° C. The reaction mixture was stirred for 15 min and it was diluted with dichloromethane. The organic phase was washed with water, dried (Na$_2$SO$_4$) and concentrated. The residue was purified by column chromatography on silica gel (20% ethyl acetate/hexane) to give the product 4 (0.84 g, 99% yield) as a light yellow oil.

$[α]_D$ +20.6 (c 1.0, CHCl$_3$); $^1$H NMR (400 MHz, CDCl$_3$) δ 7.78 (2H, d, J=8.2 Hz), 7.34 (2H, d, J=8.2 Hz), 4.01 (1H, d, J=2.0 Hz), 3.96 (1H, dd, J=9.2, 3.0 Hz), 3.79 (1H, dd, J=9.2, 6.5 Hz), 2.45 (3H, s), 1.87 (1H, m), 0.94 (3H, d, J=5.9 Hz), 0.93 (9H, t, J=7.9 Hz), 0.86 (3H, s), 0.54 (6H, q, J=7.9 Hz); $^{13}$C NMR (125 MHz, CDCl$_3$) δ 144.55 (0), 133.10 (0), 129.73 (1), 127.91 (1), 75.76 (2), 69.11 (1), 52.70 (1), 52.36 (1), 42.12 (0), 40.39 (2), 35.72 (1), 34.47 (2), 26.52 (2), 22.88 (2), 21.63 (3), 17.56 (2), 16.76 (3), 13.46 (3), 6.91 (3), 4.89 (2); MS (EI) m/z no M$^+$, 319 (46), 291 (9), 265 (9), 246 (5), 217 (100), 189 (81), 161 (69), 133 (54), 103 (38), 94 (39); MS (ESI) m/z 503 (100, [M+Na]$^-$), 983 (40, [2M+Na]$^+$), 1463 (71, [3M+Na]$^+$); exact mass calculated for C$_{26}$H$_{44}$O$_4$SSiNa [M+Na]$^+$ 503.2627, found 503.2629.

(8S,20S)-Des-A,B-8-[(triethylsilyl)oxy]-20-(formyl)-pregnane (5)

Sodium bicarbonate (5 g, 59.5 mmol) was added to a solution of tosylate 4 (2.31 g, 4.81 mmol) in DMSO (15 mL). The reaction mixture was stirred for 1 hour 15 min at 120° C. and it was diluted with ethyl acetate. The organic phase was washed with brine, dried (Na$_2$SO$_4$) and concentrated. The residue was purified by column chromatography on silica gel (5% ethyl acetate/hexane) to give the product 5 (1.19 g, 76% yield) as a colorless oil.

$[α]_D$ +41.4 (c 1.0, CHCl$_3$); $^1$H NMR (400 MHz, CDCl$_3$) δ 9.58 (1H, d, J=3.2 Hz), 4.06 (1H, d, J=2.4 Hz), 2.36 (1H, m), 1.09 (3H, d, J=6.8, 3.0 Hz), 0.96 (3H, s), 0.94 (9H, t, J=7.9 Hz), 0.56 (6H, q, J=7.9 Hz); $^{13}$C NMR (125 MHz, CDCl$_3$) δ 205.40 (1), 69.01 (1), 52.38 (1), 51.69 (1), 49.17 (1), 42.64 (0), 40.49 (2), 34.54 (2), 26.20 (2), 23.28 (2), 17.58 (2), 13.89 (3), 13.32 (3), 6.92 (3), 4.90 (2); MS (EI) m/z 324 (5, M$^-$), 295 (100, M$^+$-EtOH), 281 (30), 246 (12), 191 (36), 175 (99), 135 (54), 103 (76); MS (ESI) m/z 671 (100, [2M+Na]$^+$), 995 (49, [3M+Na]$^+$); exact mass calculated for C$_{17}$H$_{31}$O$_2$Si [M-Et]$^+$ 295.2093, found 295.2103.

(8S,20R)-Des-A,B-8-[(triethylsilyl)oxy]-20-(hydroxymethyl)-pregnane (7)

Tetrabutylammonium hydroxide (40 wt. % solution in water, 4 mL, 3.98 g, 0.015 mol) was added to a solution of aldehyde 5 (0.97 g, 2.99 mmol) in dichloromethane (20 mL). The reaction mixture was stirred for 18 hours at room temperature and it was diluted with dichloromethane. The organic phase was washed with water, dried (Na$_2$SO$_4$) and concentrated. The product was purified by column chromatography on silica gel (3%, then 5% ethyl acetate/hexane) to give a mixture of isomers 6 (0.69 g, 71% yield). Sodium borohydride (0.2 g, 5.29 mmol) was added to a solution of aldehydes 6 (0.69 g, 2.13 mmol) in THF (10 mL) and ethanol (10 mL). The reaction mixture was stirred for 45 min, quenched with saturated NH$_4$Cl, extracted with ethyl acetate and dried (Na$_2$SO$_4$). The residue was purified by column chromatography on silica gel (4%, then 20%) ethyl acetate/hexane) to give the pure isomer 7 (0.326 g, 47% yield) and a mixture of both isomers 7 and 8 (0.277 g, 40% yield).

$[α]_D$ +33.6 (c 1.0, CHCl$_3$); $^1$H NMR (500 MHz, CDCl$_3$) δ 4.03 (1H, d, J=2.5 Hz), 3.72 (1H, dd, J=10.7, 3.6 Hz), 3.44 (1H, dd, J=10.7, 7.0 Hz), 0.95 (9H, t, J=7.9 Hz), 0.94 (3H, d, J=6.6 Hz), 0.93 (3H, s), 0.55 (6H, q, J=7.9 Hz); $^{13}$C NMR (125 MHz, CDCl$_3$) δ 69.25 (1), 66.84 (2), 53.01 (1), 41.91 (0), 40.20 (2), 37.49 (1), 34.58 (2), 26.73 (2), 22.81 (2), 17.67 (2), 16.58 (3), 13.88 (3), 6.93 (3), 4.91 (2); MS (EI) m/z 326 (7, M$^+$), 311 (3, M$^+$-CH$_3$), 297 (100, M$^+$-Et), 283 (41), 265 (8), 225 (23), 193 (41), 177 (41), 135 (57), 103 (99); MS (ESI) m/z 327 (100, [M+H]$^-$); exact mass calculated for C$_{17}$H$_{33}$O$_2$Si [M-Et]$^+$297.2250, found 297.2244.

(8S,20R)-Des-A,B-8-[(triethylsilyl)oxy]-20-[(p-toluenesulfonyl)oxy]methyl-pregnane (9)

A solution of tosyl chloride (0.38 g, 2 mmol) in pyridine (3 mL) was transferred via cannula to a solution of alcohol 7 (0.326 g, 1 mmol) in pyridine (5 mL) at −20° C. The reaction mixture was stirred at −20° C. for 1 hour and then at +4° C. overnight. It was diluted with methylene chloride, washed with a saturated aqueous solution of CuSO$_4$ and dried (Na$_2$SO$_4$). The residue was purified by column chromatography on silica gel (5%, then 10% and 20% ethyl acetate/hexane) to give the tosylate 9 (427 mg, 89% yield) as a colorless oil.

$[α]_D$ +8.8 (c 1.0, CHCl$_3$); $^1$H NMR (400 MHz, CDCl$_3$) δ 7.78 (1H, d, J=8.2 Hz), 7.34 (1H, d, J=8.2 Hz), 4.11 (1H, dd, J=9.3, 3.4 Hz), 4.00 (1H, d, J=2.0 Hz), 3.77 (1H, dd, J=9.3, 7.4 Hz), 2.45 (3H, s), 0.93 (9H, t, J=7.9 Hz), 0.87 (3H, d, J=6.7 Hz), 0.81 (3H, s), 0.53 (6H, q, J=7.9 Hz); $^{13}$C NMR (100 MHz, CDCl$_3$) δ 144.53 (0), 133.18 (0), 129.70 (1), 127.93 (1), 74.30 (2), 69.09 (1), 52.74 (1), 52.60 (1), 41.77 (0), 39.95 (2), 34.66 (1), 34.40 (2), 26.61 (2), 22.64 (2), 21.62 (3), 17.54 (2), 16.65 (3), 13.82 (3), 6.91 (3), 4.89 (2); MS (EI) m/z 480 (18, M$^+$), 465 (2), 437 (14), 348 (2, M$^+$-Et$_3$SiOH), 309 (1, M$^+$-CH$_3$C$_6$H$_4$SO$_3$), 257 (91), 225 (23), 177 (100), 135 (19), 121 (24); MS (ESI) m/z 503 (7, [M+Na]$^+$), 983 (4, [2M+Na]$^+$), 1463 (10, [3M+Na]$^+$); exact mass calculated for C$_{26}$H$_{44}$O$_4$SSiNa [M+Na]$^+$ 503.2627, found 503.2639.

(8S,20S)-Des-A,B-8-[(triethylsilyl)oxy]-20-(cyanomethyl)-pregnane (10)

Sodium cyanide (0.9 g, 18.4 mmol) was added to a solution of tosylate 9 (0.412 g, 0.858 mmol) in DMSO (5 mL). The resulting mixture was stirred at 90° C. for 2 h, then it was cooled, diluted with water and extracted with ethyl acetate. Combined organic phases were dried (Na$_2$SO$_4$) and concentrated. The residue was purified by column chromatography on silica gel (10%) ethyl acetate/hexane) to give cyanide 10 (0.242 g, 85% yield) as a colorless oil.

[α]$_D$ +17.3 (c 1.0, CHCl$_3$); $^1$H NMR (400 MHz, CDCl$_3$) δ 4.04 (1H, d, J=2.2 Hz), 2.44 (1H, dd, J=16.7, 4.0 Hz), 2.38 (1H, dd, J=16.7, 6.6 Hz), 1.06 (3H, d, J=6.7 Hz), 0.94 (9H, t, J=7.9 Hz), 0.91 (3H, s), 0.55 (6H, q, J=7.9 Hz); $^{13}$C NMR (100 MHz, CDCl$_3$) δ 118.90 (0), 69.07 (1), 54.96 (1), 52.74 (1), 41.91 (0), 40.23 (2), 34.29 (2), 31.79 (1), 27.01 (2), 24.00 (2), 22.68 (2), 19.58 (3), 17.53 (2), 13.81 (3), 6.90 (3), 4.88 (2); MS (EI) m/z 335 (3, M$^+$), 320 (1, M$^+$-Me) 306 (76, M$^+$-Et), 292 (15), 271 (2), 225 (3), 202 (30), 161 (13), 103 (100), 75 (38); MS (ESI) m/z 336 (7, [M+H]$^+$), 358 (4, [M+Na]$^+$), 693 (100, [2M+Na]$^+$), 1028 (40, [3M+Na]$^+$); exact mass calculated for C$_{18}$H$_{32}$NOSi [M-Et]$^+$ 306.2253, found 306.2253.

(8S,20S22ξ)-Des-A,B-8-[(triethylsilyl)oxy]-22-cyan-25-[(triethylsilyl)oxy]-cholestane (12)

n-Butyllithium (1.6 M in hexane, 1.2 mL, 0.123 g, 1.92 mmol) was added to a solution of diisopropylamine (0.26 mL, 0.186 g, 1.84 mmol) in THF (4 mL) at 0° C. The resulting mixture was stirred at 0° C. for 30 min, then it was cooled to −78° C. and a solution of cyanide 10 (0.239 g, 0.713 mmol) in THF (3 mL) was added. The mixture was stirred at −78° C. for 30 min and a solution of bromide 11 (0.41 g, 1.46 mmol) was added. The reaction mixture was stirred at −78° C. for 1 h and then at 0° C. for 1 h. It was quenched with a saturated aqueous NH$_4$Cl solution and extracted with ethyl acetate. Combined organic phases were washed with brine, dried (Na$_2$SO$_4$) and concentrated. The residue was purified by column chromatography on silica gel (1%, then 10% ethyl acetate/hexane) to give a mixture of cyanides 12 (0.298 g, 79% yield).

Major isomer: $^1$H NMR (400 MHz, CDCl$_3$) δ 4.04 (1H, s), 2.80 (1H, m), 1.22 (3H, s), 1.21 (3H, s), 0.97 (3H, d, J=7.0 Hz), 0.94 (18H, t, J=7.9 Hz), 0.90 (3H, s), 0.57 (6H, q, J=7.9 Hz), 0.55 (6H, q, J=7.9 Hz); $^{13}$C NMR (100 MHz, CDCl$_3$) δ 121.43 (0), 72.66 (0), 69.19 (1), 54.29 (1), 52.81 (1), 42.96 (2), 41.94 (0), 40.42 (2), 36.58 (1), 36.48 (1), 34.34 (2), 30.16 (3), 29.57 (3), 27.21 (2), 25.86 (2), 22.68 (2), 17.59 (2), 14.37 (3), 13.78 (3), 7.08 (3), 6.92 (3), 6.70 (2), 4.90 (2); MS (EI) m/z no M$^+$, 491 (3), 476 (100), 345 (6), 280 (16), 246 (5), 216 (3), 189 (8), 155 (7), 132 (22), 91 (24); exact mass calculated for C$_{29}$H$_{56}$NO$_2$Si$_2$ [M-Et]$^+$ 506.3850, found 506.3848.

(8S,20S,22ξ)-Des-A,B-8-[(triethylsilyl)oxy]-22-formyl-25-[(triethylsilyl)oxy]-cholestane (13)

Diisobutylaluminum hydride (1.5 M in toluene, 0.56 mL, 0.119 g, 0.84 mmol) was added to a solution of cyanides 12 (0.3 g, 0.56 mmol) in dichloromethane (4 mL) at −10° C. The reaction mixture was stirred at −10° C. for 1 hour, then it was quenched with a saturated aqueous sodium potassium tartrate solution (5 mL). The water phase was extracted with dichloromethane. Combined organic layers were washed with brine and dried (Na$_2$SO$_4$) and concentrated. The residue was purified by column chromatography on silica gel (3% ethyl acetate/hexane) to give a mixture of aldehydes 13 (0.228 g, 76% yield), Major isomer: $^1$H NMR (400 MHz, CDCl$_3$) δ 9.78 (1H, d, J=2.4 Hz), 4.04 (1H, d, J=1.8 Hz), 2.52 (1H, m), 1.21 (3H, s), 1.20 (3H, s), 0.95 (3H, d, J=8.0 Hz) covered by 0.95 (9H, t, J=7.9 Hz), 0.94 (9H, t, J=7.9 Hz), 0.92 (3H, s), 0.56 (6H, q, J=7.9 Hz), 0.55 (6H, q, J=7.9 Hz); $^{13}$C NMR (100 MHz, CDCl$_3$) δ 206.75 (1), 73.08 (0), 69.23 (1), 54.52 (1), 53.87 (1), 52.86 (1), 42.95 (2), 42.53 (0), 40.63 (2), 36.04 (1), 34.53 (2), 30.07 (3), 29.56 (3), 27.02 (2), 22.79 (2), 22.08 (2), 17.67 (2), 14.40 (3), 14.07 (3), 7.11 (3), 6.94 (3), 6.75 (2), 4.92 (2); MS (ESI) m/z 539 (100, [M+H]$^+$), 561 (70, [M+Na]$^+$), 1099 (57, [2M+Na]$^+$); exact mass calculated for C$_{31}$H$_{62}$O$_3$Si$_2$H [M+H]$^+$ 539.4316, found 539.4312.

(8S,20S,22ξ)-Des-A,B-8-[(triethylsilyl)oxy]-22-(hydroxymethyl)-25-[(triethylsilyl)oxy]-cholestane (14)

Sodium borohydride (0.2 g, 5.29 mmol) was added to a solution of aldehydes 13 (0.23 g, 0.427 mmol) in methanol (4 mL) at 0° C. The reaction mixture was warmed to room temperature and stirred for 2 h, then it was quenched with water and extracted with ethyl acetate. Combined organic layers were washed with brine and dried (Na$_2$SO$_4$) and concentrated. The residue was purified by column chromatography on silica gel (3%, then 10% ethyl acetate/hexane) to give a mixture of alcohols 14 (0.16 g, 70% yield) as a colorless oil.

Major isomer: $^1$H NMR (500 MHz, CDCl$_3$) δ 4.03 (1H, d, J=2.2 Hz), 3.75 (1H, dd, J=10.5, 3.9 Hz), 3.41 (1H, dd, J=10.5, 8.5 Hz), 1.96 (1H, m), 1.210 (3H, s), 1.206 (3H, s), 0.95 (18H, t, J=7.9 Hz), 0.92 (3H, s), 0.73 (3H, d, J=7.0 Hz), 0.57 (6H, q, J=7.9 Hz), 0.55 (6H, q, J=7.9 Hz); $^{13}$C NMR (125 MHz, CDCl$_3$) δ 73.54 (0), 69.35 (1), 63.76 (2), 53.41 (1), 53.11 (1), 43.39 (1), 43.03 (2), 42.41 (0), 40.38 (2), 35.32 (1), 34.68 (2), 29.89 (3), 29.79 (3), 27.43 (2), 24.41 (2), 22.93 (2), 17.70 (2), 13.60 (3, C-18 and C-21), 7.12 (3), 6.94 (3), 6.77 (2), 4.94 (2); Minor isomer (visible signals): $^1$H NMR (500 MHz, CDCl$_3$) δ 3.61 (1H, dd, J=10.9, 4.6 Hz), 3.47 (1H, dd, J=10.9, 8.8 Hz); MS (ESI) m/z 541 (29, [M+H]$^+$), 563 (110, [M+Na]$^+$), 1103 (14, [2M+Na]$^+$); exact mass calculated for C$_{31}$H$_{64}$O$_3$Si$_2$Na [M+Na]$^+$ 563.4292, found 563.4313.

(8S,20S,22ξ)-Des-A,B-8-[(triethylsilyl)oxy]-22-[(p-toluenesulfonyl)oxy]methyl-25-[(triethylsilyl)oxy]-cholestane (15)

A solution of tosyl chloride (0.3 g, 1.57 mmol) in pyridine (1 mL) was added to a mixture of alcohols 14 (0.16 g, 0.3 mmol) in dry pyridine (3 mL) at −20° C. The reaction mixture was stirred at −20° C. for 1 hour and at +4° C. for 18 h. Then it was quenched with a saturated aqueous CuSO$_4$ solution and extracted with dichloromethane. Combined organic phases were dried (Na$_2$SO$_4$) and concentrated. The residue was purified by column chromatography on silica gel (3%, then 5% ethyl acetate/hexane) to give a mixture of tosylates 15 (0.17 g, 83% yield).

Major isomer: $^1$H NMR (400 MHz, CDCl$_3$) δ 7.79 (2H, d, J=8.2 Hz), 7.34 (2H, d, J=8.1 Hz), 4.06 (1H, dd, J=9.0, 3.8 Hz), 3.99 (1H, d, J=2.0 Hz), 3.80 (1H, t, J=9.0 Hz), 2.44 (3H, s), 1.16 (3H,s), 1.14 (3H, s), 0.93 (9H, t, J=7.8 Hz), 0.92 (9H, t, J=7.8 Hz), 0.85 (3H, s), 0.66 (3H, d, J=7.0 Hz), 0.54 (12H, q, J=7.8 Hz); MS (ESI) m/z 717 (15, [M+Na]$^+$); exact mass calculated for C$_{38}$H$_{70}$O$_5$SSi$_2$Na [M+Na]$^+$ 717.4380, found 717.4363.

(8S,20S,22ξ)-Des-A,B-8-[(triethylsilyl)oxy]-22-methyl-25-[(triethylsilyl)oxy]-cholestane (16)

LiAlH$_4$ (0.2 g, 5.26 mmol) was added to a solution of tosylates 15 (0.17 g, 0.24 mmol) in dry diethyl ether (5 mL) at 0° C. The reaction mixture was stirred at +4° C. for 20 h. The excess of LiAlH$_4$ was decomposed with water. The reaction mixture was diluted with diethyl ether and then it was filtered through Celite. The filtrate was extracted with ethyl acetate, dried (Na$_2$SO$_4$) and concentrated. The residue was purified by column chromatography on silica gel (3%, then 5% ethyl acetate/hexane) to give a mixture of products 16 (96 mg, 75% yield).

Major isomer: $^1$H NMR (400 MHz, CDCl$_3$) δ 4.03 (1H, d, J=1.7 Hz), 1.93 (1H, m), 1.18 (6H, s), 0.95 (18H, t, J=7.9 Hz), 0.90 (3H, s), 0.73 (3H, d, J=6.7 Hz), 0.67 (3H, d, J=6.8 Hz), 0.56 (6H, q, J=7.9 Hz), 0.55 (6H, q, J=7.8 Hz); $^{13}$C NMR (100 MHz, CDCl$_3$) δ 73.48 (0), 69.47 (1), 53.62 (1), 53.23 (1), 43.29 (2), 42.25 (0), 40.39 (2), 38.10 (1), 34.74 (1 and 2), 30.31 (2), 29.89 (3, C-26 and C-27), 27.57 (2), 22.91 (2), 17.78 (2), 13.93 (3), 13.50 (3), 12.14 (3), 7.13 (3), 6.95 (3), 6.82 (2), 4.95 (2); MS (EI) m/z no M$^+$, 506 (0.9, M$^+$-H$_2$O), 495 (46, M$^+$-Et), 481 (6), 391 (7), 363 (43), 349 (2), 307 (2), 259 (20), 245 (7), 225 (14), 173 (91), 135 (41), 103 (100); exact mass calculated for C$_{29}$H$_{59}$O$_2$Si$_2$ [M-Et]$^+$ 495.4054, found 495.4058.

(8S,20S,22R)-Des-A,B-22-methyl-cholestan-8,25-diol (17) and (8S,20S,22S)-Des-A,B-22-methyl-cholestan-8,25-diol (18)

Tetrabutylammonium fluoride (1.0 M in THF, 1 mL, 1 mmol) was added to a solution of compounds 16 (96.4 mg, 0.184 mmol) in THF (3 mL) at 0° C. The reaction mixture was stirred at +4° C. for 20 h, then it was diluted with water and extracted with ethyl acetate. Combined organic extracts were dried (Na$_2$SO$_4$) and concentrated. The residue was purified by column chromatography on silica gel (30% ethyl acetate/hexane) to give a mixture of diols 17 and 18 (55 mg, 99% yield) in 2:1 ratio, respectively (based on $^1$H NMR). Isomers were separated by crystallization from ethyl acetate and absolute configuration was established by X-ray analysis. Pure crystals (38.9 mg) of the isomer 17 were obtained after two crystallizations and the 22R absolute configuration of the diol 17 was established. Diol 18 (22S) (16.4 mg) containing a small amount of isomer 22R was obtained from the filtrate after second crystallization.

17: m.p. 133-134° C. (EtOAc); [α]$_D$ +32.5 (c 1.0, CHCl$_3$); $^1$H NMR (500 MHz, CDCl$_3$) δ 4.07 (1H, d, J=1.9 Hz), 1.95 (1H, m), 1.21 (6H, s), 0.93 (3H, s), 0.76 (3H, d, J=6.8 Hz), 0.69 (3H, d, J=6.8 Hz); $^{13}$C NMR (125 MHz, CDCl$_3$) δ 71.08 (0), 69.41 (1), 53.42 (1), 52.70 (1), 42.13 (2), 41.95 (0), 39.97 (2), 38.04 (1), 34.65 (1), 33.59 (2), 30.27 (2), 29.30 (3), 29.15 (3), 27.42 (2), 22.36 (2), 17.49 (2), 13.80 (3), 13.52 (3), 12.06 (3); MS (EI) m/z no M$^+$, 278 (46, M$^+$-H$_2$O), 260 (32, M$^+$-2H$_2$O), 245 (16), 217 (9), 179 (20), 163 (47), 151 (48), 145 (63), 125 (69), 111 (100); MS (ESI) m/z 319 (18, [M+Na]$^+$); exact mass calculated for C$_{19}$H$_{36}$O$_2$Na [M+Na]$^+$ 319.2613, found 319.2623.

18: $^1$H NMR (500 MHz, CDCl$_3$) δ 4.08 (1H, s), 1.93 (1H, m), 1.21 (6H, s), 0.92 (3H, s), 0.86 (3H, d, J=6.8 Hz), 0.74 (3H, d, J=6.8 Hz); $^{13}$C NMR (125 MHz, CDCl$_3$) δ 71.28 (0), 69.40 (1), 53.03 (1), 52.56 (1), 42.34 (2), 41.91 (0), 40.49 (1), 39.83 (2), 34.99 (1), 33.54 (2), 29.21 (3), 29.12 (3), 27.05 (2), 24.62 (2), 22.46 (2), 18.35 (3), 17.49 (2), 13.60 (3), 13.07 (3); MS (EI) m/z 296 (15, M$^+$), 278 (33, M$^+$-H$_2$O), 260 (15, M$^+$-2H$_2$O), 246 (100), 210 (6), 196 (18), 181 (36), 163 (29), 125 (28), 111 (65); exact mass calculated for C$_{19}$H$_{36}$O$_2$Na [M+Na]$^+$ 319.2613, found 319.2605.

(20S,22R)-Des-A,B-22-methyl-25-[(triethylsilyl)oxy]-cholestan-8one (19A)

Molecular sieves 4 Å (60 mg) were added to a solution of 4-methylmorpholine oxide (36 mg, 0.307 mmol) in dichloromethane (0.5 mL). The mixture was stirred at room temperature for 15 min and tetrapropylammonium perruthenate (3 mg, 8.54 μmol) was added, followed by a solution of diol 17 (15 mg, 0.051 mmol) in dichloromethane (400+300 μL). The resulting suspension was stirred at room temperature for 1 h. The reaction mixture was filtered through a Waters silica Sep-Pak cartridge (2 g) that was further washed with ethyl acetate. After removal of the solvent the ketone (15 mg) was obtained as a colorless oil.

Triethylsilyl trifluoromethanesulfonate (60 μL, 70 mg, 0.265 mmol) was added dropwise to a solution of the ketone (15 mg, 0.051 mmol) and 2,6-lutidine (110 μL, 0.101 g, 0.94 mmol) in dichloromethane (2 mL) at −40° C. The reaction mixture was stirred at −40° C. for 15 min, then it was diluted with dichloromethane and washed with water. The organic layer was dried (Na$_2$SO$_4$) and concentrated. The residue was applied to a Waters silica Sep-Pak cartridge (5 g). Elution with hexane/ethyl acetate (0.5% then 1%) gave the protected ketone 19A (14 mg, 68% yield).

(20S,22S)-Des-A,B-22-methyl-25-[(triethylsilyl)oxy]-cholestan-8-one (19B)

Molecular sieves 4 Å (60 mg) were added to a solution of 4-methylmorpholine oxide (51 mg, 0.435 mmol) in dichloromethane (0.5 mL). The mixture was stirred at room temperature for 15 min and tetrapropylammonium perruthenate (7 mg, 0.02 mmol) was added, followed by a solution of diol 18 (14.3 mg, 0.048 mmol) in dichloromethane (400+300 μL). The resulting suspension was stirred at room temperature for 1 h. The reaction mixture was filtered through a Waters silica Sep-Pak cartridge (2 g) that was further washed with ethyl acetate. After removal of the solvent the ketone (15 mg) was obtained as a colorless oil.

Triethylsilyl trifluoromethanesulfonate (40 μL, 46 mg, 0.176 mmol) was added dropwise to a solution of the ketone (15 mg, 0.051 mmol) and 2,6-lutidine (80 μL, 74 mg, 0.69 mmol) in dichloromethane (2 mL) at −40° C. The reaction mixture was stirred at −40° C. for 15 min, then it was diluted with dichloromethane and washed with water. The organic layer was dried (Na$_2$SO$_4$) and concentrated. The residue was applied to a Waters silica Sep-Pak cartridge (5 g). Elution with hexane/ethyl acetate (1%) gave the protected ketone 19B (14.4 mg, 73% yield).

$^1$H NMR (500 MHz, CDCl$_3$) δ 2.45 (1H, dd, J=11.5, 7.2 Hz), 1.207 (3H, s), 1.205 (3H, s), 0.96 (9H, t, J=8.0 Hz), 0.85 (3H, d, J=6.8 Hz), 0.76 (3H, d, J=6.9 Hz), 0.62 (3H, s), 0.58 (6H, q, J=8.0 Hz); $^{13}$C NMR (125 MHz, CDCl$_3$) δ 212.11 (0), 73.46 (0), 61.90 (1), 53.21 (1), 50.04 (0), 43.50 (2), 41.00 (2), 40.66 (1), 38.44 (2), 35.50 (1), 30.09 (3), 29.62 (3), 27.17 (2), 24.81 (2), 24.03 (2), 19.01 (2), 18.29 (3), 13.19 (3), 12.49 (3), 7.14 (3), 6.81 (2); MS (EI) m/z no M$^+$, 393 (9, M$^+$-CH$_3$), 379 (34, M$^+$-Et), 350 (17), 335 (2), 293 (2), 259 (34), 239 (6), 225 (3), 206 (7), 191 (38), 173 (100), 149 (16), 135 (80), 103 (80), 75 (67); MS (ESI) m/z 431 (34, [M+Na]$^+$), 839 (100, [2M+Na]$^+$), 1248 (28, [3M+H+Na]$^+$); exact mass calculated for C$_{25}$H$_{48}$O$_2$SiNa [M+Na]$^+$ 431.3321, found 431.3316.

(20S,22R)-2-Methylene-19-nor-22-methyl-1α,25-dihydroxyvitamin D$_3$ (IIA)

Phenyllithium (1.8 M in di-n-butyl ether, 45 μL, 6.8 mg, 0.081 mmol) was added to a stirred solution of the phosphine oxide 20 (50 mg, 86 μmol) in anhydrous THF (400 μL) at −30° C. After 30 min the mixture was cooled to −78° C. and a precooled solution of the ketone 19A (14 mg, 34 μmol) in anhydrous THF (300+200 μL) was added. The reaction mixture was stirred under argon at −78° C. for 4 hours and then at +4° C. for 19 h. Ethyl acetate was added and the organic phase was washed with brine, dried (Na$_2$SO$_4$) and concentrated. The residue was applied to a Waters silica Sep-Pak cartridge (5 g). The cartridge was washed with hexane and ethyl acetate/hexane (1:99) to give the protected vitamin 21A (23.89 mg, 90% yield).

UV (in hexane) λmax 263.0, 253.0, 245.0 nm; $^1$H NMR (500 MHz, CDCl$_3$) δ 6.22 (1H, d, J=11.1 Hz, 6-H), 5.84 (1H, d, J=11.1 Hz, 7-H), 4.97 (1H, s, =CH$_2$), 4.92 (1H, s, =CH$_2$), 4.43 (2H, m, 1β-H and 3α-H), 2.83 (1H, dm, J=12.4 Hz), 2.52 (1H, dd, J=13.3, 5.8 Hz, 10α-H), 2.46 (1H, dd, J=12.5, 4.3 Hz, 4α-H), 2.33 (1H, dd, J=13.3, 2.9 Hz, 10β-H), 2.18 (1H, dd, J=12.5, 8.3 Hz, 4β-H), 2.00 (2H, m), 1.187 and 1.180 (each 3H, each s, 26-H$_3$, 27-H$_3$), 0.94 (9H, t, J=7.9 Hz), 0.896 (9H, s, t-BuSi), 0.865 (9H, s, t-BuSi), 0.762 (3H, d, J=6.7 Hz, 28-H$_3$), 0.706 (3H, d, J=5.8 Hz, 21-H$_3$), 0.561 (6H, q, J=7.9 Hz), 0.535 (3H, s, 18-H$_3$), 0.080 (3H, s, SiMe), 0.067 (3H, s, SiMe), 0.049 (3H, s, SiMe), 0.026 (3H, s, SiMe); $^{13}$C NMR (125 MHz, CDCl$_3$) δ 152.98 (0, C-2), 141.24 (0, C-8), 132.72 (0, C-5), 122.42 (1, C-6), 116.13 (1, C-7), 106.25 (2, =CH$_2$), 73.50 (0, C-25), 72.53 and 71.63 (each 1, C-1, C-3), 56.35 (1), 53.54 (1), 47.61 (2), 45.73 (0, C-13), 43.33 (2), 40.28 (2), 39.03 (1), 38.56 (2), 35.03 (1), 30.37 (2), 29.89 and 29.85 (each 3, C-26, C-27), 28.78 (2), 27.88 (2), 25.84 (3), 25.77 (3), 23.44 (2), 22.10 (2), 18.25 (0), 18.16 (0), 13.93 (3), 12.24 (3), 11.96 (3), 7.13 (3), 6.82 (2), −4.87 (3), −5.10 (3); MS (ESI) m/z 795 (20, [M+Na$^-$]); exact mass (ESI) calculated for C$_{46}$H$_{88}$O$_3$Si$_3$Na [M+Na]$^+$ 795.5939, found 795.5946.

The protected vitamin 21A (23.89 mg, 30.9 μmol) was dissolved in THF (4 mL) and acetonitrile (3 mL). A solution of aqueous 48% HF in acetonitrile (1:9 ratio, 4 mL) was added at 0° C. and the resulting mixture was stirred at room temperature for 2 h. Saturated aqueous NaHCO$_3$ solution was added and the reaction mixture was extracted with dichloromethane. The combined organic phases were dried (Na$_2$SO$_4$) and concentrated under reduced pressure. The residue was diluted with 2 mL of hexane/ethyl acetate (7:3) and applied to a Waters silica Sep-Pak cartridge (5 g). An elution with hexane/ethyl acetate (7:3, then 1:1) gave the crude product IIA. The vitamin IIA was further purified by straight phase HPLC [9.4×250 mm Zorbax Silica column, 4 mL/min, hexane/2-propanol (85:15) solvent system, R$_t$=7.9 min.] and reverse phase HPLC [9.4×250 mm Zorbax RX-C18 column, 3 mL/min, methanol/water (85:15) solvent system, R$_t$=14.7 min.] to give the pure compound IIA (10.285 mg, 77% yield), m.p. 117° C. (Et$_2$O); UV (in EtOH) λ$_{max}$ 261.5, 252.0, 244.5 nm; $^1$H NMR (500 MHz, CDCl$_3$) δ 6.35 (1H, d, J=11.2 Hz, 6-H), 5.89 (1H, d, J=11.2 Hz, 7-H), 5.11 (1H, s, =CH$_2$), 5.08 (1H, s, =CH$_2$), 4.46 (2H, m, 1β-H and 3α-H), 2.85 (1H, dd, J=13.8, 4.4 Hz, 4α-H), 2.82 (1H, m), 2.56 (1H, dd, J=13.3, 3.5 Hz, 10β-H), 2.33 (1H, dd, J=13.3, 6.0 Hz, 10α-H), 2.29 (1H, dd, J=13.8, 8.4 Hz, 4β-H), 1.21 (6H, s, 26-H$_3$, 27-H$_3$), 0.78 (3H, d, J=6.7 Hz, 28-H$_3$), 0.71 (3H, d, J=5.7 Hz, 21-H$_3$), 0.54 (3H, s, 18-H$_3$); $^{13}$C NMR (125 MHz, CDCl$_3$) δ 151.98 (0, C-2), 143.25 (0, C-8), 130.52 (0, C-5), 124.14 (1, C-6), 115.36 (1, C-7), 107.69 (2, =CH$_2$), 71.76 (1), 71.14 (0), 70.58 (1), 56.34 (1), 53.48 (1), 45.80 (0), 45.74 (2), 42.11 (2), 40.08 (2), 38.81 (1), 38.12 (2), 34.96 (1), 30.24 (2), 29.26 (3), 29.12 (3), 28.93 (2), 27.78 (2), 23.44 (2), 22.11 (2), 13.88 (3), 12.14 (3), 12.04 (3); MS (EI) m/z no M$^+$, 401 (100, M$^+$-Et), 383 (52, M$^+$-Et-H$_2$O), 351 (15), 314 (14), 289 (39), 272 (27), 236 (38), 202 (10), 173 (19), 144 (42), 120 (95), 94 (59); MS (ESI) m/z 453 (100, [M+Na]$^+$), 883 (25, [2M+Na]$^+$), 1314 (5, [3M+H+Na]$^+$); exact mass calculated for C$_{28}$H$_{46}$O$_3$Na [M+Na]$^+$ 453.3345 found 453.3329.

(20S,22S)-2-Methylene-19-nor-22-methyl-1α,25-dihydroxyvitamin D$_3$ (IIB)

Phenyl lithium (1.83 M in di-n-butyl ether, 50 μL, 7.7 mg, 0.091 mmol) was added to a stirred solution of the phosphine oxide 20 (55 mg, 86 μmol) in anhydrous THF (400 μL) at −30° C. After 30 min the mixture was cooled to −78° C. and a precooled solution of the ketone 19B (14.4 mg, 35 μmol) in anhydrous THF (300+200 μL) was added. The reaction mixture was stirred under argon at −78° C. for 4 hours and then at +4° C. for 19 h. Ethyl acetate was added and the organic phase was washed with brine, dried (Na$_2$SO$_4$) and concentrated. The residue was applied to a Waters silica Sep-Pak cartridge (5 g). The cartridge was washed with hexane and ethyl acetate/hexane (2:98) to give the protected vitamin 21B (23.618 mg, 87% yield).

UV (in hexane) λmax 263.0, 253.5, 245.5 nm; $^1$H NMR (500 MHz, CDCl$_3$) δ 6.22 (1H, d, J=11.2 Hz, 6-H), 5.84 (1H, d, J=11.2 Hz, 7-H), 4.97 (1H, s, =CH$_2$), 4.92 (1H, s, =CH$_2$), 4.43 (2H, m, 1β-H and 3α-H), 2.83 (1H, dm, J=12.5 Hz), 2.52 (1H, dd, J=13.2, 6.1 Hz, 10α-H), 2.46 (1H, dd, J=12.7, 4.1 Hz, 4α-H), 2.33 (1H, dd, J=13.2, 2.9 Hz, 10β-H), 2.18 (1H, dd, J=12.7, 8.4 Hz, 4β-H), 2.00 (1H, m), 1.19 (6H, s, 26-H$_3$, 27-H$_3$), 0.95 (9H, t, J=7.9 Hz), 0.897 (9H, s, t-BuSi), 0.865 (9H, s, t-BuSi), 0.84 (3H, d, J=6.8 Hz), 0.75 (3H, d, J=6.8 Hz), 0.57 (6H, q, J=7.9 Hz), 0.53 (3H, s, 18-H$_3$), 0.080 (3H, s, SiMe), 0.067 (3H, s, SiMe), 0.049 (3H, s, SiMe), 0.026 (3H, s, SiMe); $^{13}$C NMR (125 MHz, CDCl$_3$) δ 152.98 (0, C-2), 141.24 (0, C-8), 132.71 (0, C-5), 122.43 (1, C-6), 116.08 (1, C-7), 106.25 (2, =CH$_2$), 73.57 (0, C-25), 72.53 and 71.63 (each 1, C-1, C-3), 56.21 (1), 53.17 (1), 47.61 (2), 45.74 (0, C-13), 43.50 (2), 41.31 (1), 40.09 (2), 38.55 (2), 35.34 (1), 29.96 (3) and 29.73 (each 3, C-26 and C-27), 28.80 (2), 27.45 (2), 25.84 (3), 25.78 (3), 24.82 (2), 23.44 (2), 22.17 (2), 18.43 (3), 18.25 (0), 18.16 (0), 13.17 (3), 12.10 (3), 7.15 (3), 6.82 (2), −4.87 (3), −5.10 (3).

The protected vitamin 21B (23.518 mg, 30.5 μmol) was dissolved in THF (4 mL) and acetonitrile (3 mL). A solution of aqueous 48% HF in acetonitrile (1:9 ratio, 4 mL) was added at 0° C. and the resulting mixture was stirred at room temperature for 2 h. A saturated aqueous NaHCO$_3$ solution was added and the reaction mixture was extracted with dichloromethane. The combined organic phases were dried (Na$_2$SO$_4$) and concentrated under reduced pressure. The residue was diluted with 2 mL of hexane/ethyl acetate (7:3) and applied to a Waters silica Sep-Pak cartridge (5 g). An elution with hexane/ethyl acetate (7:3, then 1:1) gave the crude product IIB. The vitamin IIB was further purified by straight phase HPLC [9.4×250 mm Zorbax Silica column, 4 mL/min, hexane/2-propanol (85:15) solvent system, R$_t$=7.3 min.] and reverse phase HPLC [9.4×250 mm Zorbax RX-C18 column, 3 mL/min, methanol/water (85:15) solvent system, R$_t$=11.7 min.] to give the vitamin IIB (6.56 mg, 50% yield) and its (22R) epimer (2.92 mg, 22% yield), UV (in EtOH) λ$_{max}$ 261.5, 252.5, 245.0 nm; $^1$H NMR (500 MHz, CDCl$_3$) δ 6.35 (1H, d, J=11.2 Hz, 6-H), 5.89 (1H, d, J=11.2 Hz, 7-H), 5.11 (1H, s, =CH$_2$), 5.09 (1H, s, =CH$_2$), 4.46 (2H, m, 1β-H and 3α-H), 2.85 (1H, dd, J=13.0, 4.4 Hz, 4α-H), 2.82 (1H, dm, J=13.7 Hz), 2.57 (1H, dd, J=13.4, 3.8 Hz, 10β-H), 2.33 (1H, dd, J=13.4, 6.2 Hz, 10α-H), 2.29 (1H, dd, J=13.0, 8.4 Hz, 4β-H), 2.03 (1H, m), 1.91 (dm, J=12.1 Hz), 1.22 (6H, s, 26-H$_3$, 2.7-H$_3$), 0.86 (3H, d, J=6.8 Hz), 0.76 (3H, d, J=6.8 Hz), 0.54 (3H, s, 18-H$_3$); $^{13}$C NMR (125 MHz, CDCl$_3$) δ 151.96 (0, C-2), 143.31 (0, C-8), 130.46 (0, C-5), 124.22 (1, C-6), 115.32 (1, C-7), 107.71 (2, =CH$_2$), 71.79 and 70.66 (each 1, C-1, C-3), 71.25 (0, C-25), 56.21 (1), 53.06 (1), 45.86 (0, C-13), 45.78 (2), 42.36 (2), 41.15 (1), 39.93 (2), 38.14 (2), 35.40 (1), 29.19 (3, C-26 and C-27), 28.95 (2), 27.37 (2), 24.80 (2), 23.47 (2), 22.23 (2), 18.32 (3), 13.20 (3), 12.14 (3); MS (EI) m/z 430 (9, M$^+$), 412 (3, M$^-$-H$_2$O), 328 (7), 313 (8), 297 (5), 251 (5), 227 (3), 211 (5), 194 (48), 161 (12), 135 (51), 105 (100); exact mass calculated $C_{28}H_{46}O_3$ [M]$^+$ 430.3447 found 430.3447.

Example 1B

Synthesis of (20R,22S)-2-methylene-19-nor-22-methyl-1α,25-dihydroxyvitamin D$_3$ and (20R,22R)-2-methylene-19-nor-22-methyl-1α,25-dihydroxyvitamin D$_3$ Compounds of formula I, formula II, formula IIC and formula IID were prepared using the methods shown in Schemes 4 and 5. As shown in Scheme 4, Compound 4 was reacted with sodium cyanide in DMSO to give cyanide 22. The cyano compound 22 was then treated with 4-bromo-2-methyl-1-triethylsilyloxy butane (11), in presence of a mixture of n-butyllithium and diisopropylamine, to provide compound 23. The cyano group of compound 23 was converted to the corresponding aldehyde 24 by treating it with diisobutylaluminum hydride in dichloromethane. Aldehyde 24 was then reduced to alcohol 25 using sodium borohydride in methanol. The free hydroxyl group of compound 25 was then reacted with tosyl chloride in pyridine and the resulting tosyl protected compound 26 was reduced to the corresponding alkane 27 using lithium aluminum hydride as the reducing agent. The triethylsilyl protected dihydroxy compound 27 was then deprotected using tetrabutylammonium fluoride in THF and the racemic mixture of diols thus obtained was separated by crystallization from ethyl acetate to provide the two separate isomers, the 22S 28 diol and 22R diol 29. Each of the diols 28 and 29 were then separately oxidized (TPAP/4-MMO or PDC/PPTS) to produce the respective ketones. Each ketone was further independently treated with triethylsilyl trifluoromethanesulfonate and 2,6-lutidine in dichloromethane to provide the triethylsilyl protected ketone 22S compound 30A or 22R compound 30B.

Scheme 4

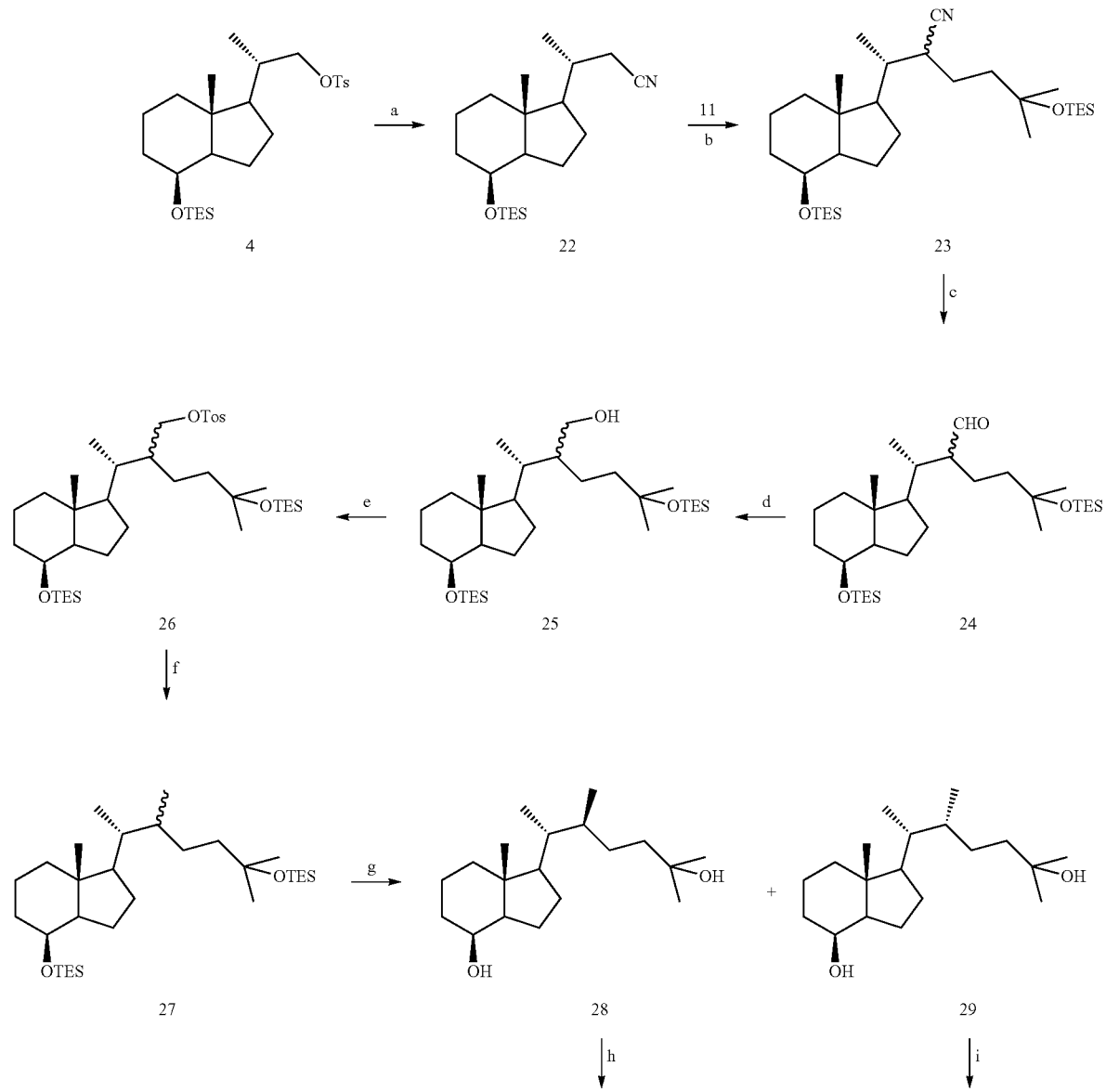

-continued

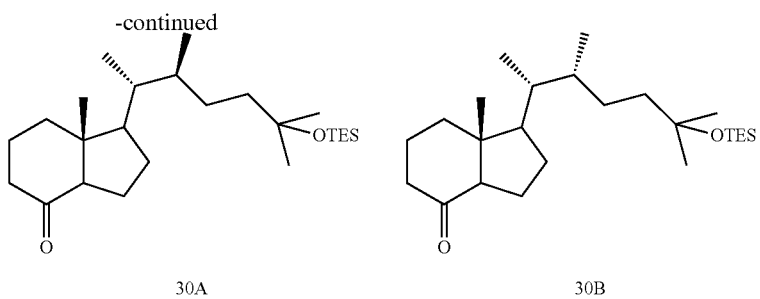

30A  30B

∿∿ indicates that the carbon is in either the R or S configuration.
a) NaCN, DMSO (22, 97%)
b) 1. n-BuLi, DIPA, THF; 2. 11 (23, 93%)
c) DIBAL, toluene, DCM (24, 79%)
d) NaBH₄, MeOH (25, 71%)
e) TosCl, pyridine (26, 92%)
f) LiAlH₄, DEE (27, 80%)
g) 1. TBAF, THF (28 and 29, 99%); 2. Crystallization from EtOAc
h) 1. PDC, PPTS, DCM; 2. TESOTf, 2,6-lutidine, DCM (30A, 53%)
i) 1. Mol sieves 4Å, 4-MMO, TPAP, DCM; 2. TESOTf, 2,6-lutidine, DCM (30B, 95%)

Scheme 5 illustrates the conversion of compounds 30A or 30B to compounds IIC or IID. A Wittig-Horner condensation of the protected Grundmann's Ketone (compound 30A or 30B) with the phosphine oxide (compound 20) in the presence of phenyllithium was performed as shown is Scheme 5. Finally, the target compound (compound IIC or IID) was generated by deprotection of hydroxy groups in compounds 31A or 31B in the presence of hydrofluoric acid.

Scheme 5

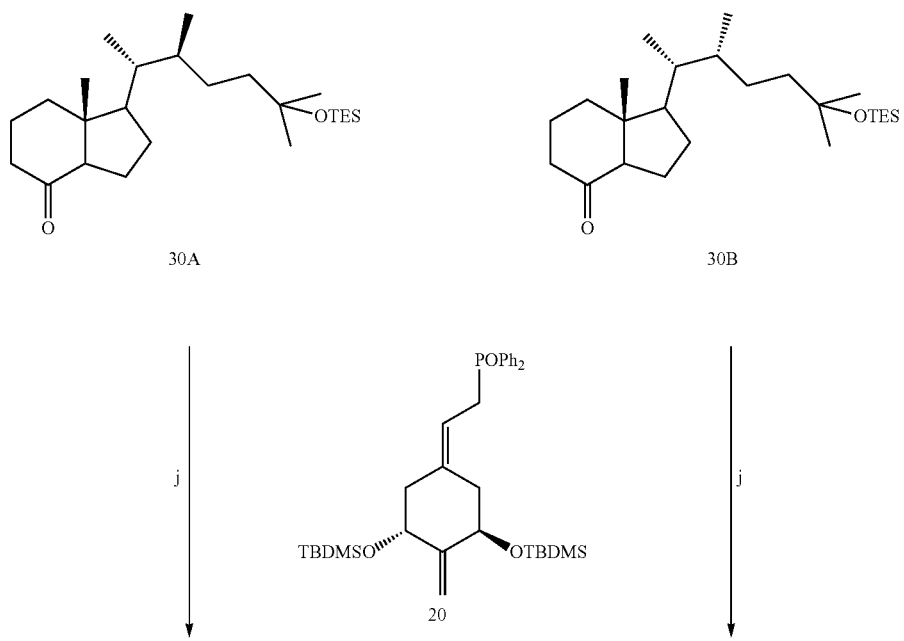

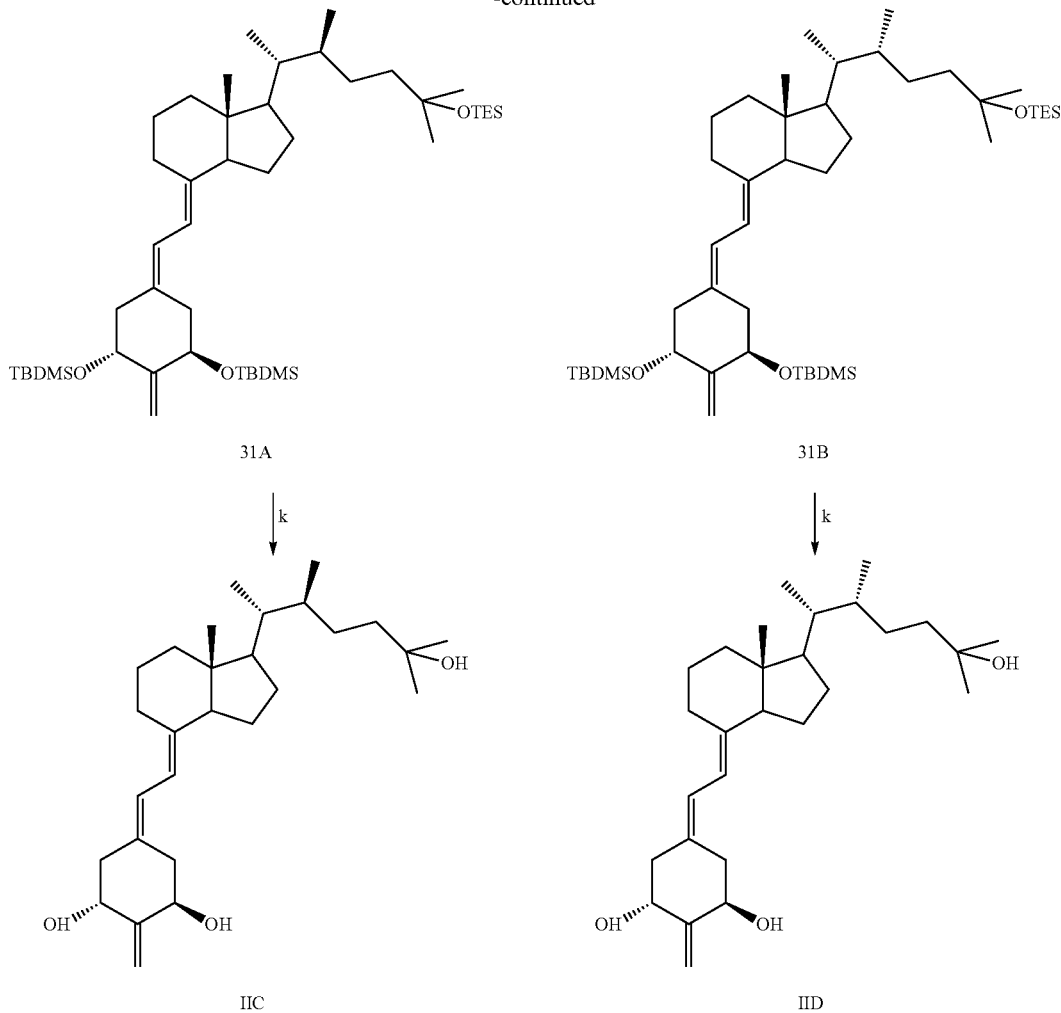

j) PhLi, THF, 20 (31A, 90%) (31B, 91%)
k) HF, MeCN, THF (IIC, 79%) (IID, 78%)

(8S,20S)-Des-A,B-8[(triethylsilyl)oxy]-20-(cyanomethyl)-pregnane (22)

Sodium cyanide (2 g, 41 mmol) was added to a solution of tosylate 4 (0.84 g, 1.75 mmol) in dry DMSO (8 mL). The resulting mixture was stirred at 90° C. for 3 h, then it was cooled, diluted with water and extracted with ethyl acetate. Combined organic phases were dried (Na$_2$SO$_4$) and concentrated. The residue was purified by column chromatography on silica gel (10% ethyl acetate/hexane) to give the cyanide 22 (0.57 g, 97% yield) as a colorless oil.

$[\alpha]_D$ +16.6° (c 1.0, CHCl$_3$); $^1$H NMR (400 MHz, CDCl$_3$) δ 4.04 (1H, d, J=2.1 Hz), 2.34 (1H, dd, J=16.6, 3.7 Hz), 2.23 (1H, dd, J=16.6, 7.0 Hz), 1.92 (1H, m), 1.13 (3H, d, J=6.6 Hz), 0.942 (9H, t, J=7.9 Hz), 0.921 (3H, s), 0.55 (6H, q, J=7.9 Hz); $^{13}$C NMR (125 MHz, CDCl$_3$) δ 119.09 (0), 69.12 (1), 55.34 (1), 52.86 (1), 42.18 (0), 40.35 (2), 34.40 (2), 33.09 (1), 27.19 (2), 24.69 (2), 22.82 (2), 19.23 (3), 17.53 (2), 13.63 (3), 6.91 (3), 4.89 (2); MS (EI) m/z 335 (10), 320 (3), 306 (100), 292 (28), 225 (7), 202 (20), 188 (10), 161 (17), 135 (14), 103 (55); exact mass calculated for C$_{20}$H$_{37}$ONSi (M$^+$) 335.2644, found 335.2656.

(8S,20R,22ξ)-Des-A,B-8-[(triethylsilyl)oxy]-22-cyano-25-[(triethylsilyl)oxy]-cholestane (23)

n-Butyllithium (1.6 M in hexane, 2.7 mL, 0.28 g, 4.32 mmol) was added to a solution of diisopropylamine (0.6 mL, 0.43 g, 4.25 mmol) in THF (4 mL) at 0° C. The resulting mixture was stirred at 0° C. for 30 min, then it was cooled to −78° C. and a solution of cyanide 22 (0.57 g, 1.70 mmol) in THF (5 mL) was added. The mixture was stirred at −78° C. for 30 min and a solution of bromide 11 (0.96 g, 3.42 mmol) was added. The reaction mixture was stirred at −78° C. for 1 h and then at 0° C. for 1 h. It was quenched with a saturated aqueous NH$_4$Cl solution and extracted with ethyl acetate. Combined organic phases were washed with brine and dried (Na$_2$SO$_4$) and concentrated. The residue was purified by column chromatography on silica gel (1.5%, 3% and 10% ethyl acetate/hexane) to give a mixture of cyanides 23 (0.85 g, 93% yield).

Major isomer: $^1$H NMR (400 MHz, CDCl$_3$) δ 4.03 (1H, s), 2.56 (1H, m), 1.22 (3H, s), 1.21 (3H, s), 1.04 (3H, d, J=6.6 Hz), 0.944 (18H, t, J=7.8 Hz), 0.923 (3H, s), 0.57 (6H, q, J=7.8 Hz), 0.55 (6H, q, J=7.8 Hz); Minor isomer (visible signals): $^1$H NMR (400 MHz, CDCl$_3$) δ 1.08 (3H, d, J=6.8 Hz); MS (EI) m/z 492 (36), 478 (6), 390 (11), 374 (96), 351 (53), 322 (11), 271 (18), 225 (13), 201 (23), 185 (25), 173

(75), 131 (51), 103 (100); MS (ESI) m/z 558 (30, [M+Na]⁺), 1093 (20, [2M+Na]⁺); exact mass calculated for $C_{31}H_{61}NO_2Si_2Na$ [M+Na]⁻ 558.4139, found 558.4141.

(8S,20R,22ξ)-Des-A,B-8-[(triethylsilyl)oxy]-22-formyl-25-[(triethylsilyl)oxy]-cholestane (24)

Diisobutylaluminum hydride (1.5 M in toluene, 1.4 mL, 0.3 g, 2.1 mmol) was added to a solution of cyanides 23 (0.81 g, 1.51 mmol) in dichloromethane (10 mL) at −10° C. The reaction mixture was stirred at −10° C. for 1 hour, then it was quenched with a saturated aqueous sodium potassium tartrate solution (5 mL). The water phase was extracted with dichloromethane. Combined organic layers were washed with brine and dried ($Na_2SO_4$) and concentrated. The residue was purified by column chromatography on silica gel (3% ethyl acetate/hexane) to give a mixture of aldehydes 24 (0.64 g, 79% yield).

Major isomer: ¹H NMR (400 MHz, $CDCl_3$) δ 9.72 (1H, d, J=3.2 Hz), 4.03 (1H, br s), 1.20 (6H, s), 1.02 (3H, d, J=7.0 Hz), 0.944 (9H, t, J=7.8 Hz), 0.939 (9H, t, J=7.8 Hz), 0.920 (3H, s), 0.563 (6H, q, J=7.8 Hz), 0.554 (6H, q, J=7.8 Hz); Minor isomer (visible signals): ¹H NMR (400 MHz, $CDCl_3$) δ 9.63 (1H, s); MS (EI) m/z 453 (1), 377 (5), 353 (8), 321 (18), 295 (8), 257 (20), 201 (53), 173 (88), 163 (43), 135 (26), 115 (59), 103 (100); MS (ESI) m/z 561 (80, [M+Na]⁻), 1099 (40, [2M+Na]⁺); exact mass calculated for $C_{31}H_{62}O_3Si_2Na$ [M+Na]⁺ 561.4135 found 561.4139.

(8S,20R,22ξ)-Des-A,B-8-[(triethylsilyl)oxy]-22-(hydroxymethyl)-25-[(triethylsilyl)oxy]-cholestane (25)

Sodium borohydride (0.44 g, 11.63 mmol) was added to a solution of aldehydes 24 (0.64 g, 1.19 mmol) in methanol (10 mL) at 0° C. The reaction mixture was warmed to room temperature and stirred for 2 h, then it was quenched with water and extracted with ethyl acetate. Combined organic layers were washed with brine and dried ($Na_2SO_4$) and concentrated. The residue was purified by column chromatography on silica gel (3%, 10% ethyl acetate/hexane) to give a mixture of alcohols 25 (0.46 g, 71% yield) as a colorless oil.

Major isomer: ¹H NMR (500 MHz, $CDCl_3$) δ 4.03 (1H, br s), 3.71 (1H, dd, J=10.7, 4.2 Hz), 3.39 (1H, dd, J=10.7, 8.0 Hz), 1.205 (6H, s), 0.946 (18H, t, J=7.9 Hz), 0.909 (3H, s), 0.798 (3H, d, J=7.1 Hz), 0.568 (6H, q, J=7.9 Hz), 0.551 (6H, q, J=7.9 Hz); Minor isomer (visible signals): ¹H NMR (500 MHz, $CDCl_3$) δ 3.61 (1H, dd, J=10.8, 4.8 Hz), 3.46 (1H, dd, J=10.8, 9.2 Hz), 0.784 (1H, d, J=7.3 Hz); MS (EI) m/z 453 (1), 425 (2), 391 (40), 340 (5), 311 (57), 297 (27), 259 (35), 225 (37), 207 (24), 191 (40), 173 (72), 163 (46), 135 (100); MS (ESI) m/z 563 (100, [M+Na]⁺), 1103 (50, [2M+Na]⁺); exact mass calculated for $C_{31}H_{64}O_3Si_2Na$ [M+Na]⁺ 563.4292 found 563.4298.

(8S,20R,22ξ)-Des-A,B-8-[(triethylsilyl)oxy]-22-methyl-25-[(triethylsilyl)oxy]-cholestane (27)

A solution of tosyl chloride (0.66 g, 3.46 mmol) in pyridine (2 mL) was added to a mixture of alcohols 25 (0.46 g, 0.85 mmol) in dry pyridine (4 mL) at −20° C. The reaction mixture was stirred at −20° C. for 1 hour and at +4° C. for 18 h. Then it was pulled into a saturated aqueous $CuSO_4$ solution and extracted with dichloromethane. Combined organic phases were dried ($Na_2SO_4$) and concentrated. The residue was purified by column chromatography on silica gel (3% ethyl acetate/hexane) to give a mixture of tosylates 26 (0.54 g, 92% yield). $LiAlH_4$ (0.4 g, 10.53 mmol) was added to a solution of tosylates 26 (0.53 g, 0.76 mmol) in dry diethyl ether (10 mL) at 0° C. The reaction mixture was stirred at +4° C. for 20 h. The excess of $LiAlH_4$ was decomposed with water. The reaction mixture was diluted with diethyl ether and then it was filtered through Celite. The filtrate was extracted with ethyl acetate, dried ($Na_2SO_4$) and concentrated. The residue was purified by column chromatography on silica gel (3% ethyl acetate/hexane) to give a mixture of products 27 (0.32 g, 80% yield).

Major isomer: ¹H NMR (400 MHz, $CDCl_3$) δ 4.03 (1H, br s), 1.94 (1H, m), 1.182 (6H, s), 0.952 (18H, t, J=7.9 Hz), 0.917 (3H, s), 0.733 (3H, d, J=6.6 Hz), 0.690 (3H, d, J=6.7 Hz), 0.565 (6H, q, J=7.9 Hz), 0.556 (6H, q, J=7.9 Hz); Minor isomer (visible signals): ¹H NMR (400 MHz, $CDCl_3$) δ 0.902 (3H, s), 0.843 (3H, d, J=6.8 Hz), 0.764 (3H, d, J=6.5 Hz); MS (EI) m/z 496 (62), 481 (6), 391 (11), 363 (60), 259 (28), 246 (42), 225 (25), 173 (90), 135 (66), 103 (100); MS (ESI) m/z 547 (5, [M+Na]⁻); exact mass calculated for $C_{33}H_{64}O_2Si_2Na$ [M+Na]⁺ 547.4343 found 547.4355.

(8S,20R,22S)-Des-A,B-22-methyl-cholestan-8,25-diol (28) and (8S,20R,22R)-Des-A,B-22-methyl-cholestan-8,25-diol (29)

Tetrabutylammonium fluoride (1.0 M in THF, 3.4 mL, 3.4 mmol) was added to a solution of compounds 27 (0.31 g, 0.59 mmol) in THF (3 mL) at 0° C. The reaction mixture was stirred at +4° C. for 20 h, then it was diluted with water and extracted with ethyl acetate. Combined organic extracts were dried ($Na_2SO_4$) and concentrated. The residue was purified by column chromatography on silica gel (10%, 50% ethyl acetate/hexane) to give a mixture of diols 28 and 29 (0.17 g, 99% yield) in 2:1 ratio, respectively (based on ¹H NMR). Isomers were separated by crystallization from ethyl acetate and absolute configuration was established by X-ray analysis. Pure crystals (96 mg) of the isomer 28 were obtained after first crystallization and the 22S absolute configuration of the diol 28 was established. Pure crystals (44.6 mg) of the other isomer 29 were obtained from the filtrate after first crystallization and the 22R absolute configuration of the diol 29 was established. A second batch of pure crystals (16 mg) of the diol 28 was obtained from the filtrate after second crystallization.

28: $[\alpha]_D$ +15.4° (c 1.0, $CHCl_3$); m.p. 147-148° C. (EtOAc); ¹H NMR (500 MHz, $CDCl_3$) δ 4.07 (1H, s), 1.98 (1H, dm, J=12.8 Hz), 1.209 (6H, s), 0.934 (3H, s), 0.750 (3H, d, J=6.7 Hz), 0.711 (3H, d, J=6.8 Hz); ¹³C NMR (100 MHz, $CDCl_3$) δ 71.13 (0), 69.42 (1), 54.26 (1), 52.63 (1), 42.18 (2), 41.78 (0), 40.50 (2), 38.14 (1), 34.84 (1), 33.59 (2), 30.26 (2), 29.28 (3), 29.19 (3), 26.72 (2), 22.42 (2), 17.45 (2), 13.47 (3), 13.08 (3), 12.19 (3); MS (EI) m/z no M⁺, 277 (45), 259 (36), 244 (23), 216 (16), 189 (19), 178 (35), 162 (72), 151 (33), 134 (100), 135 (33), 111 (72); MS (ESI) m/z 319 (60, [M+Na]⁺), 615 (100, [2M+Na]⁺), 911 (15, [3M+Na]⁺); exact mass calculated for $C_{19}H_{36}O_2Na$ (M+Na⁺) 319.2613, found 319.2621.

29: $[\alpha]_D$ +34.0° (c 1.0, $CHCl_3$); m.p. 108-110° C. (EtOAc); ¹H NMR (500 MHz, $CDCl_3$) δ 4.06 (1H, s), 1.97 (1H, dm, J=12.9 Hz), 1.209 (3H, s), 1.199 (3H, s), 0.922 (3H, s), 0.866 (3H, d, J=6.8 Hz), 0.779 (3H, d, J=6.6 Hz); ¹³C NMR (125 MHz, $CDCl_3$) δ 71.17 (0), 69.39 (1), 54.25 (1), 52.57 (1), 42.78 (2), 41.78 (0), 40.89 (1), 40.46 (2), 35.03 (1), 33.60 (2), 29.55 (3), 29.00 (3), 26.82 (2), 23.70 (2), 22.45 (2), 18.89 (3), 17.45 (2), 13.45 (3), 12.87 (3); MS (EI) m/z no M⁺, 278 (53), 260 (22), 245 (17), 217 (7), 191 (12), 179 (13), 163 (52), 151 (31), 135 (48), 111 (100); MS (ESI) m/z 319 (45, [M+Na]⁺), 615 (55, [2M+Na]$^+$), 911 (10, [3M+Na]$^+$); exact mass calculated for C$_{19}$H$_{36}$O$_2$Na (MNa$^+$) 319.2613, found 319.2619.

(20R,22S)-Des-A,B-22-methyl-25-[(triethylsilyl)oxy]-cholestan-8-one (30A)

Pyridinium dichromate (0.18 g, 0.48 mmol) and pyridinium p-toluenesulfonate (24 mg, 95 μmol) were added in one portion to a solution of diol 28 (24.9 mg, 84 μmol) in dry dichloromethane (5 mL). The reaction mixture was stirred at room temperature for 1 hour 15 min, then it was quenched with water and extracted with dichloromethane. Combined organic layers were dried (Na$_2$SO$_4$) and concentrated. The residue was applied to a Waters silica Sep-Pak cartridge (2 g). Elution with dichloromethane gave the ketone (23.6 mg). Triethylsilyl trifluoromethanesulfonate (25 μL, 29.2 mg, 0.11 mmol) was added drop wise to a solution of the ketone (23.6 mg) and 2,6-lutidine (30 μL, 27.6 mg, 0.26 mmol) in dry dichloromethane (2 mL) at −40° C. The reaction mixture was stirred at −40° C. for 15 min, then it was diluted with dichloromethane and washed with water. The organic layer was dried (Na$_2$SO$_4$) and concentrated. The residue was applied to a Waters silica Sep-Pak cartridge (10 g). Elution with ethyl acetate/hexane (2:98, then 5:95) gave the protected ketone 30.4 (18.2 mg, 53% yield in 2 steps).

[α]$_D$ −7.8° (c 1.0, CHCl$_3$); $^1$H NMR (400 MHz, CDCl$_3$) δ 2.46 (1H, dd, J=11.4, 7.5 Hz), 1.176 (6H, s), 0.935 (9H, t, J=7.9 Hz), 0.797 (3H, d, J=6.6 Hz), 0.719 (3H, d, J=6.7 Hz), 0.643 (3H, s), 0.553 (6H, q, J=7.9 Hz); $^{13}$C NMR (100 MHz, CDCl$_3$) δ 212.20 (0), 73.38 (0), 62.01 (1), 54.47 (1), 49.90 (0), 43.25 (2), 40.98 (2), 39.09 (2), 38.43 (1), 35.00 (1), 30.19 (2), 29.86 (3), 29.82 (3), 27.17 (2), 24.09 (2), 18.96 (2), 13.14 (3), 12.44 (3), 12.37 (3), 7.10 (3), 6.77 (2); MS (EI) m/z no M$^+$, 393 (13), 379 (38), 350 (35), 259 (43), 203 (17), 173 (100), 163 (64), 135 (84), 103 (99); MS (ESI) m/z 431 (2, [M+Na]$^+$), 839 (20, [2M+Na]$^+$), 1248 (60, [3M+H+Na]$^+$); exact mass calculated for C$_{25}$H$_{48}$O$_2$SiNa (MNa$^+$) 431.3321, found 431.3318.

(20R,22R)-Des-A,B-22-methyl-25-[(triethylsilyl)oxy]-cholestan-8-one (30B)

Molecular sieves 4 Å (60 mg) were added to a solution of 4-methylmorpholine oxide (33 mg, 0.282 mmol) in dichloromethane (0.25 mL). The mixture was stirred at room temperature for 15 min and tetrapropylammonium perruthenate (2 mg, 5.7 μmol) was added, followed by a solution of diol 29 (16 mg, 54 μmol) in dichloromethane (300+250 μL). The resulting suspension was stirred at room temperature for 1 h. The reaction mixture was filtered through a Waters silica Sep-Pak cartridge (2 g) that was further washed with ethyl acetate. After removal of the solvent, the ketone (14.4 mg, 89% yield) was obtained as a colorless oil.

Triethylsilyl trifluoromethanesulfonate (20 μL, 23 mg, 88 μmol) was added dropwise to a solution of the ketone (14.4 mg, 49 μmol) and 2,6-lutidine (20 μL, 18 mg, 0.17 mmol) in dichloromethane (2 mL) at −40° C. The reaction mixture was stirred at −40° C. for 15 min, then it was diluted with dichloromethane and washed with water. The organic layer was dried (Na$_2$SO$_4$) and concentrated. The residue was applied to a Waters silica Sep-Pak cartridge (5 g). Elution with ethyl acetate/hexane (1:99, then 2:98) gave the protected ketone 30B (19 mg, 95% yield),

[α]$_D$ +3.4 (c 1.0, CHCl$_3$); NMR (400 MHz, CDCl$_3$) δ 2.45 (1H, dd, J=11.4, 7.6 Hz), 1.207 (3H, s), 1.183 (3H, s), 0.955 (9H, t, J=7.9 Hz), 0.865 (3H, d, J=6.8 Hz), 0.835 (3H, d, J=6.8 Hz), 0.636 (3H, s), 0.569 (6H, q, J=7.9 Hz); $^{13}$C NMR (100 MHz, CDCl$_3$) δ 212.19 (0), 73.49 (0), 62.01 (1), 54.55 (1), 49.87 (0), 43.90 (2), 41.28 (1), 40.99 (2), 39.12 (2), 35.31 (1), 30.42 (3), 29.46 (3), 27.28 (2), 24.10 (2), 23.61 (2), 18.96 (3 and 2), 13.06 (3), 12.37 (3), 7.14 (3), 6.83 (2); MS (EI) m/z no M$^+$, 393 (12), 379 (68), 350 (30), 259 (14), 203 (8), 173 (100), 163 (36), 135 (45), 103 (73); exact mass calculated for C$_{23}$H$_{43}$O$_2$Si [M-Et]$^-$ 379.3032, found 379.3032.

(20R,22S)-2-Methylene-19-nor-22-methyl-1α,25-dihydroxyvitamin D$_3$ (IIC)

Phenyllithium (1.8 M in di-n-butyl ether, 50 μL, 7.56 mg, 90 μmol) was added to a stirred solution of the phosphine oxide 20 (51 mg, 88 μmol) in anhydrous THF (500 μL) at −30° C. After 30 min the mixture was cooled to −78° C. and a precooled solution of the ketone 30A (17.9 mg, 44 μmol) in anhydrous THF (300+200 μL) was added. The reaction mixture was stirred under argon at −78° C. for 4 hours and then at +4° C. for 19 h. Ethyl acetate was added and the organic phase was washed with brine, dried (Na$_2$SO$_4$) and concentrated. The residue was applied to a Waters silica Sep-Pak cartridge (5 g). The cartridge was washed with hexane and ethyl acetate/hexane (1:99) to give the protected vitamin 31A (30.66 mg, 90% yield).

UV (in hexane) λ$_{max}$ 262.5, 253.0, 245.0 nm; $^1$H NMR (500 MHz, CDCl$_3$) δ 6.22 (1H, d, J=11.1 Hz, 6-H), 5.84 (1H, d, J=11.1 Hz, 7-H), 4.97 (1H, s, =CH$_2$), 4.92 (1H, s, =CH$_2$), 4.43 (2H, m, 1β-H and 3α-H), 2.83 (1H, dm, J=12.3 Hz), 2.53 (1H, dd, J=13.3, 5.9 Hz, 10α-H), 2.47 (1H, dd, J=13.0, 4.5 Hz, 4α-H), 2.33 (1H, dd, J=13.3, 2.7 Hz, 10β-H), 2.18 (1H, dd, J=13.0, 8.4 Hz, 4β-H), 1.188 (6H, s, 26-H$_3$, 27-H$_3$), 0.949 (9H, t, J=7.9 Hz), 0.900 (9H, s, t-BuSi), 0.875 (3H, d, J=7.6 Hz, 21-H$_3$), 0.868 (9H, s, t-BuSi), 0.722 (3H, d, J=6.7 Hz), 0.567 (6H, q, J=7.9 Hz), 0.559 (3H, s, 18-H$_3$), 0.083 (3H, s, SiMe), 0.069 (3H, s, SiMe), 0.052 (3H, s, SiMe), 0.029 (3H, s, SiMe); $^{13}$C NMR (100 MHz, CDCl$_3$) δ 152.98 (0, C-2), 141.33 (0, C-8), 132.69 (0, C-5), 122.43 (1, C-6), 116.05 (1, C-7), 106.24 (2, =CH$_2$), 73.52 (0, C-25), 72.55 and 71.60 (each 1, C-1, C-3); 56.32 (1), 54.23 (1), 47.61 (2), 45.65 (0, C-13), 43.35 (2), 40.74 (2), 39.07 (1), 38.53 (2), 35.01 (1), 30.37 (2), 29.90 and 29.80 (each 3, C-26, C-27), 28.80 (2), 27.33 (2), 25.84 (3), 25.77 (3), 23.49 (2), 22.13 (2), 18.26 (0), 18.16 (0), 13.19 and 12.53 and 11.96 (each 3, C-21, C-28, C-18), 7.13 (3), 6.81 (2), −4.87 (3), −5.10 (3); MS (ESI) m/z 795 (100, [M+Na$^-$]); exact mass (ESI) calculated for C$_{46}$H$_{88}$O$_3$Si$_3$Na [M+Na]$^+$ 795.5939 found 795.5910.

The protected vitamin 31A (30.66 mg, 39.7 μmol) was dissolved in THF (4 mL) and acetonitrile (3 mL). A solution of aqueous 48% HF in acetonitrile (1:9 ratio, 4 mL) was added at 0° C. and the resulting mixture was stirred at room temperature for 3.5 h. Saturated aqueous NaHCO$_3$ solution was added and the reaction mixture was extracted with dichloromethane. The combined organic phases were dried (Na$_2$SO$_4$) and concentrated under reduced pressure. The residue was diluted with 2 mL of hexane/ethyl acetate (7:3) and applied to a Waters silica Sep-Pak cartridge (5 g). An elution with hexane/ethyl acetate (7:3, then 1:1) gave the crude product IIC. The vitamin IIC was further purified by straight phase HPLC [9.4×250 mm Zorbax Silica column, 4 mL/min, hexane/2-propanol (85:15) solvent system, R$_t$=8.5 min.] and reverse phase HPLC [9.4×250 mm Zorbax RX-C18 column, 3 mL/min, methanol/water (85:15) solvent system, R$_t$=15.2 min.] to give the pure compound IIC (13.52 mg, 79% yield).

UV (in EtOH) λ$_{max}$ 261.5, 252.0, 244.5 nm; $^1$H NMR (500 MHz, CDCl$_3$) δ 6.35 (1H, d, J=11.3 Hz, 6-H), 5.88 (1H, d, J=11.3 Hz, 7-H), 5.10 (1H, s, =CH$_2$), 5.08 (1H, s, =CH$_2$), 4.46 (2H, m, 1β-H and 3α-H), 2.85 (1H, dd, J=13.1, 4.5 Hz, 10β-H), 2.82 (1H, dm, J=15.9 Hz, 9β-H), 2.57 (1H, dd, J=13.4, 3.6 Hz, 4α-H), 2.33 (1H, dd, J=13.4, 6.1 Hz, 4β-H), 2.28 (1H, dd, J=13.1, 8.4 Hz, 10α-H), 2.00 (2H, m), 1.210 (6H, s, 26-$H_3$, 27-$H_3$), 0.78 (3H, d, J=5.8 Hz, 21-$H_3$), 0.73 (3H, d, J=6.8 Hz, 28-$H_3$), 0.554 (3H, s, 18-$H_3$); $^{13}C$ NMR (125 MHz, $CDCl_3$) δ 151.97 (0, C-2), 143.43 (0, C-8), 130.41 (0, C-5), 124.23 (1, C-6), 115.27 (1, C-7), 107.70 (2, =$CH_2$), 71.15 (0, C-25), 71.81 and 70.63 (each 1, C-1, C-3); 56.34 (1), 54.19 (1), 45.75 (0, C-13), 45.75 (2), 42.17 (2), 40.58 (2), 39.04 (1), 38.16 (2), 35.01 (1), 30.28 (2), 29.26 (3), 29.20 (3), 28.99 (2), 27.25 (2), 23.52 (2), 22.17 (2), 13.07 and 12.49 and 12.02 (each 3, C-21, C-28, C-18); MS (EI) m/z 430 (62, $M^+$), 412 (26, $M^+$-$H_2O$), 394 (13, $M^+$-$2H_2O$), 379 (24, $M^+$-$CH_3$-$2H_2O$), 351 (20), 315 (27), 293 (34), 259 (43), 173 (94), 149 (72), 135 (100); MS (ESI) m/z 453 (95, $[M+Na]^+$), 883 (50, $[2M+Na]^+$), 1314 (10, $[3M+H+Na]^+$); exact mass calculated for $C_{28}H_{46}O_3Na$ $[M+Na]^+$ 453.3345 found 453.3358.

(20R,22R)-2-Methylene-19-nor-22-methyl-1α,25-dihydroxyvitamin $D_3$ (IID)

Phenyllithium (1.8 M in di-n-butyl ether, 60 μL, 9.08 mg, 108 μmol) was added to a stirred solution of the phosphine oxide 20 (54 mg, 93 μmol) in anhydrous THF (500 μL) at −30° C. After 30 min the mixture was cooled to −78° C. and a precooled solution of the ketone 30B (19 mg, 47 μmol) in anhydrous THF (300+200 μL) was added. The reaction mixture was stirred under argon at −78° C. for 4 hours and then at +4° C. for 19 h. Ethyl acetate was added and the organic phase was washed with brine, dried ($Na_2SO_4$) and concentrated. The residue was applied to a Waters silica Sep-Pak cartridge (5 g). The cartridge was washed with hexane and ethyl acetate/hexane (1:99) to give the protected vitamin 31B (32.64 mg, 91% yield).

UV (in hexane) $λ_{max}$ 262.5, 253.0, 245.0 nm; $^1H$ NMR (500 MHz, $CDCl_3$) δ 6.22 (1H, d, J=11.2 Hz, 6-H), 5.84 (1H, d, J=11.2 Hz, 7-H), 4.97 (1H, s, =$CH_2$), 4.92 (1H, s, =$CH_2$), 4.43 (2H, m, 1β-H and 3α-H), 2.82 (1H, dm, J=12.4 Hz), 2.53 (1H, dd, J=13.3, 5.9 Hz, 10α-H), 2.47 (1H, dd, J=12.8, 4.5 Hz, 4α-H), 2.32 (1H, dd, J=13.3, 2.9 Hz, 10β-H), 2.18 (1H, dd, J=12.8, 8.4 Hz, 4β-H), 1.204 and 1.182 (each 3H, each s, 26-$H_3$, 27-$H_3$), 0.955 (9H, t, J=7.9 Hz), 0.898 (9H, s, t-BuSi), 0.863 (9H, s, t-BuSi), 0.858 (3H, d, J=5.4 Hz, 21-$H_3$), 0.808 (3H, d, J=6.8 Hz), 0.569 (6H, q, J=7.9 Hz), 0.542 (3H, s, 18-$H_3$), 0.081 (3H, s, SiMe), 0.065 (3H, s, SiMe), 0.050 (3H, s, SiMe), 0.024 (3H, s, SiMe); $^{13}C$ NMR (125 MHz, $CDCl_3$) δ 152.99 (0, C-2), 141.36 (0, C-8), 132.71 (0, C-5), 122.43 (1, C-6), 116.05 (1, C-7), 106.25 (2, =$CH_2$), 73.58 (0, C-25), 72.56 and 71.60 (each 1, C-1, C-3), 56.31 (1), 54.28 (1), 47.62 (2), 45.62 (0, C-13), 44.01 (2), 41.94 (1), 40.73 (2), 38.53 (2), 35.41 (1), 30.40 and 29.50 (each 3, C-26, C-27), 28.81 (2), 27.46 (2), 25.84 (3), 25.78 (3), 23.70 (2), 23.49 (2), 22.13 (2), 19.01 (3), 18.26 (0), 18.16 (0), 13.11 (3), 11.97 (3), 7.16 (3), 6.86 (2), −4.86 (3), −4.91 (3), −5.11 (3); MS (ESI) m/z 795 (50, $[M+Na^+]$); exact mass (ESI) calculated for $C_{46}H_{88}O_3Si_3Na$ $[M+Na]^+$ 795.5939, found 795.5916.

The protected vitamin 31B (32.64 mg, 42 μmol) was dissolved in THF (4 mL) and acetonitrile (3 mL). A solution of aqueous 48% HF in acetonitrile (1:9 ratio, 4 mL) was added at 0° C. and the resulting mixture was stirred at room temperature for 2 h. Saturated aqueous $NaHCO_3$ solution was added and the reaction mixture was extracted with dichloromethane. The combined organic phases were dried ($Na_2SO_4$) and concentrated under reduced pressure. The residue was diluted with 2 mL of hexane/ethyl acetate (7:3) and applied to a Waters silica Sep-Pak cartridge (5 g). An elution with hexane/ethyl acetate (7:3, then 1:1) gave the crude product IID. The vitamin IID was further purified by straight phase HPLC [9.4×250 mm Zorbax Silica column, 5 mL/min, hexane/2-propanol (85:15) solvent system, $R_t$=6.5 min.] and reverse phase HPLC [9.4×250 mm Zorbax RX-C18 column, 3 mL/min, methanol/water (85:15) solvent system, $R_t$=13.2 min.] to give the pure compound IID (15.28 mg, 78% yield). Pure crystals of the analog IID were obtained after crystallization from hexane/2-propanol and they were characterized by an X-ray analysis.

m.p. 159° C. (hexane/2-propanol); UV (in EtOH) $λ_{max}$ 261.5, 252.5, 244.5 nm; $^1H$ NMR (500 MHz, $CDCl_3$) δ 6.35 (1H, d, J=11.3 Hz, 6-H), 5.89 (1H, d, J=11.3 Hz, 7-H), 5.11 (1H, s, =$CH_2$), 5.08 (1H, s, =$CH_2$), 4.46 (2H, m, 1β-H and 3α-H), 2.85 (1H, dd, J=13.2, 4.5 Hz, 10β-H), 2.83 (1H, dm, J=13.6 Hz, 9β-H), 2.57 (1H, dd, J=13.4, 3.8 Hz, 4α-H), 2.33 (1H, dd, J=13.4, 6.1 Hz, 4β-H), 2.29 (1H, dd, J=13.2, 8.4 Hz, 10α-H), 1.227 and 1.219 (each 3H, each s, 26-$H_3$, 27-$H_3$), 0.882 (3H, d, J=6.8 Hz, 21-$H_3$), 0.818 (3H, d, J=6.8 Hz, 28-$H_3$), 0.549 (3H, s, 18-$H_3$); $^{13}C$ NMR (125 MHz, $CDCl_3$) δ 151.97 (0, C-2), 143.39 (0, C-8), 130.44 (0, C-5), 124.19 (1, C-6), 115.25 (1, C-7), 107.69 (2, =$CH_2$), 71.23 (0, C-25), 71.78 and 70.59 (each 1, C-1, C-3), 56.25 (1), 54.15 (1), 45.74 (2), 45.74 (0), 42.76 (2), 41.79 (1), 40.50 (2), 38.12 (2), 35.15 (1), 29.53 (3), 29.01 (3), 29.01 (2), 27.35 (2), 23.66 (2), 23.52 (2), 22.19 (2), 18.93 (3), 13.13 (3), 12.02 (3); MS (EI) m/z 430 (100, $M^+$), 412 (24, $M^-$-$H_2O$), 394 (10, $M^+$-$2H_2O$), 379 (10, $M^+$-$CH_3$-$2H_2O$), 343 (9), 315 (41), 297 (26), 262 (53), 183 (21), 161 (30), 135 (50); exact mass (ESI) calculated for $C_{28}H_{46}O_3$ $[M+Na]^+$ 453.3345 found 453.3344.

X-Ray Analysis of (8S,20R,22S)-Des-A,B-22-methyl-cholestan-8,25-diol (28)

A colorless prism-shaped crystal of compound 28 having dimensions 0.11×0.18×0.45 mm was selected for structural analysis. Intensity data were collected using a Broker AXS Platinum 135 CCD detector controlled with the PROTEUM software suite (Bruker AXS Inc., Madison, Wis.). The x-ray source was CuK radiation (1.54178 Å) from a Rigako RU200 x-ray generator equipped with Montel optics, operated at 50 kV and 90 mA. The x-ray data were processed with SAINT version 7.06A (Bruker AXS Inc.) and internally scaled with SADABS version 2005/1 (Bruker AXS Inc.). The sample was mounted on a glass fiber using vacuum grease and cooled to 100 K. The intensity data were measured as a series of phi and omega oscillation frames each of 1° for 5 sec/frame. The detector was operated in 512×512 mode and was positioned 4.5 cm from the sample. Cell parameters were determined from a non-linear least squares fit of 3987 peaks in the range of 4.0°<theta<55°. The data were merged to form a set of 2821 independent data with R(int)=0.042.

The monoclinic space group C2 was determined by systematic absences and statistical tests and verified by subsequent refinement. The structure was solved by direct methods and refined by full-matrix least-squares methods on $F^2$, (a) G. M. Sheldrick (1994), SHELXTL Version 5 Reference Manual, Bruker AXS Inc.; (b) *International Tables for Crystallography, Vol. C*, Kluwer: Boston (1995). Hydrogen atom positions were determined from difference peaks and ultimately refined by a riding model with idealized geometry. Non-hydrogen atoms were refined with anisotropic displacement parameters. A total of 190 parameters were refined against 1 restraint and 2821 data to give wR2=0.1078 and S=1.134 for weights of w=1/[$s^2(F^2)$+$(0.0533P)^2$], where P=[$F_o^2$+$2F_c^2$]/3. The final R(F) was 0.0401 for the 2821 observed data. The largest shift/s.u. was 0.001 in the final refinement cycle and the final difference map had maxima and minima of 0.410 and −0.347 c/Å$^3$, respectively. The absolute structure was determined by refinement of the Flack parameter, H. D. Flack, *Acta Cryst. A*, vol. 39, 876-881 (1983). Table 1 shows the crystal data and structure refinement for compound 28. Tables 2-7 show calculated coordinates, parameters, bond lengths and angles for the crystal structure of compound 28.

TABLE 1

Crystal data and structure refinement for compound 28.

| | |
|---|---|
| Empirical formula | C19H36O2 |
| Formula weight | 296.48 |
| Temperature | 100(1) K |
| Wavelength | 1.54178 Å |
| Crystal system, space group | Monoclinic, C2 |
| Unit cell dimensions | a = 26.391(5) Å  α = 90° |
| | b = 6.0830(12) Å  β = 118.38(3)° |
| | c = 12.688(3) Å  γ = 90° |
| Volume | 1792.1(6) Å$^3$ |
| Z | 4 |
| Calculated density | 1.099 Mg/m$^3$ |
| Absorption coefficient | 0.522 mm$^{-1}$ |
| F(000) | 664 |
| Crystal size | 0.11 × 0.18 × 0.45 mm |
| Theta range for data collection | 3.81 to 64.54° |
| Limiting indices | −30 <= h <= 26, −6 <= k <= 6, 0 <= l <= 14 |
| Reflections collected/unique | 4452/2821 [R(int) = 0.0420] |
| Data/restraints/parameters | 2821/1/190 |
| Goodness-of-fit on F$^2$ | 1.134 |
| Final R indices [I > 2σ(I)] | R1 = 0.0399, wR2 = 0.1075 |
| R indices (all data) | R1 = 0.0401, wR2 = 0.1078 |
| Absolute structure parameter | 0.1(3) |
| Largest diff. peak and hole | 0.410 and −0.347 e/Å$^3$ |

TABLE 2

Atomic coordinates (×10$^4$) and equivalent isotropic displacement parameters (Å$^2$ × 10$^3$) for compound 28. U(eq) is defined as one third of the trace of the orthogonalized U$_{ij}$ tensor.

| | x | y | z | U(eq) |
|---|---|---|---|---|
| O(8) | 584(1) | −102(2) | 9286(1) | 19(1) |
| O(25) | 594(1) | −820(3) | 1455(1) | 19(1) |
| C(20) | 1536(1) | −144(3) | 6131(2) | 17(1) |
| C(13) | 1366(1) | 221(3) | 8042(2) | 14(1) |
| C(11) | 1901(1) | −325(4) | 10306(2) | 19(1) |
| C(14) | 1018(1) | 2008(3) | 8290(2) | 15(1) |
| C(8) | 947(1) | 1735(3) | 9405(2) | 16(1) |
| C(9) | 1547(1) | 1473(4) | 10489(2) | 17(1) |
| C(21) | 2136(1) | −1171(4) | 6844(2) | 21(1) |
| C(22) | 1484(1) | 1202(4) | 5042(2) | 20(1) |
| C(16) | 739(1) | 2158(4) | 6189(2) | 20(1) |
| C(24) | 988(1) | −1925(4) | 3526(2) | 19(1) |
| C(17) | 1362(1) | 1259(3) | 6915(2) | 15(1) |
| C(23) | 1471(1) | −215(4) | 4031(2) | 21(1) |
| C(25) | 824(1) | −2683(4) | 2253(2) | 18(1) |
| C(18) | 1065(1) | −2035(4) | 7726(2) | 19(1) |
| C(28) | 1952(1) | 2940(4) | 5409(2) | 23(1) |
| C(15) | 493(1) | 2396(4) | 7073(2) | 20(1) |
| C(26) | 1342(1) | −3479(4) | 2133(2) | 24(1) |
| C(12) | 1956(1) | 35(4) | 9165(2) | 17(1) |
| C(27) | 372(1) | −4480(4) | 1853(2) | 25(1) |

TABLE 3

Bond lengths [Å] for compound 28.

| | | | |
|---|---|---|---|
| O(8)—C(8) | 1.433(2) | O(25)—C(25) | 1.446(2) |
| C(20)—C(21) | 1.534(3) | C(20)—C(17) | 1.536(3) |
| C(20)—C(22) | 1.555(3) | C(13)—C(18) | 1.540(3) |
| C(13)—C(14) | 1.549(3) | C(13)—C(12) | 1.536(2) |
| C(13)—C(17) | 1.559(3) | C(11)—C(9) | 1.527(3) |
| C(11)—C(12) | 1.539(2) | C(14)—C(8) | 1.521(2) |
| C(14)—C(15) | 1.526(3) | C(8)—C(9) | 1.534(3) |
| C(22)—C(28) | 1.523(3) | C(22)—C(23) | 1.533(3) |
| C(16)—C(15) | 1.548(3) | C(16)—C(17) | 1.554(3) |
| C(24)—C(25) | 1.532(3) | C(24)—C(23) | 1.530(3) |
| C(25)—C(27) | 1.516(3) | C(25)—C(26) | 1.524(3) |

TABLE 4

Bond angles [°] for compound 28.

| | |
|---|---|
| C(21)—C(20)—C(17) | 112.66(15) |
| C(21)—C(20)—C(22) | 111.66(16) |
| C(17)—C(20)—C(22) | 110.83(17) |
| C(18)—C(13)—C(14) | 113.36(15) |
| C(18)—C(13)—C(12) | 110.28(16) |
| C(14)—C(13)—C(12) | 107.53(15) |
| C(18)—C(13)—C(17) | 110.16(15) |
| C(14)—C(13)—C(17) | 99.01(15) |
| C(12)—C(13)—C(17) | 116.14(15) |
| C(9)—C(11)—C(12) | 112.30(17) |
| C(8)—C(14)—C(15) | 120.27(15) |
| C(8)—C(14)—C(13) | 117.32(16) |
| C(15)—C(14)—C(13) | 104.12(15) |
| O(8)—C(8)—C(14) | 111.00(15) |
| O(8)—C(8)—C(9) | 111.54(16) |
| C(14)—C(8)—C(9) | 108.35(15) |
| C(11)—C(9)—C(8) | 112.57(16) |
| C(28)—C(22)—C(23) | 109.68(17) |
| C(28)—C(22)—C(20) | 112.22(16) |
| C(23)—C(22)—C(20) | 113.94(18) |
| C(15)—C(16)—C(17) | 107.12(15) |
| C(25)—C(24)—C(23) | 114.06(16) |
| C(20)—C(17)—C(16) | 111.63(15) |
| C(20)—C(17)—C(13) | 119.70(16) |
| C(16)—C(17)—C(13) | 103.25(15) |
| C(22)—C(23)—C(24) | 114.43(16) |
| O(25)—C(25)—C(27) | 109.20(15) |
| O(25)—C(25)—C(26) | 106.13(16) |
| C(27)—C(25)—C(26) | 109.73(18) |
| O(25)—C(25)—C(24) | 108.44(17) |
| C(27)—C(25)—C(24) | 110.67(16) |
| C(26)—C(25)—C(24) | 112.51(16) |
| C(14)—C(15)—C(16) | 103.09(15) |
| C(11)—C(12)—C(13) | 112.03(15) |

TABLE 5

Anisotropic displacement parameters (Å$^2$ × 10$^3$) for compound 28.

| | U$_{11}$ | U$_{22}$ | U$_{33}$ | U$_{23}$ | U$_{13}$ | U$_{12}$ |
|---|---|---|---|---|---|---|
| O(8) | 18(1) | 24(1) | 18(1) | −1(1) | 10(1) | −5(1) |
| O(25) | 20(1) | 25(1) | 14(1) | 4(1) | 8(1) | 3(1) |
| C(20) | 16(1) | 17(1) | 17(1) | −2(1) | 8(1) | −4(1) |
| C(3) | 15(1) | 12(1) | 15(1) | 0(1) | 7(1) | −1(1) |
| C(11) | 17(1) | 23(1) | 14(1) | 1(1) | 5(1) | 2(1) |
| C(14) | 16(1) | 12(1) | 17(1) | 0(1) | 8(1) | 0(1) |
| C(8) | 17(1) | 14(1) | 18(1) | −2(1) | 9(1) | −1(1) |
| C(9) | 20(1) | 18(1) | 14(1) | −1(1) | 9(1) | −3(1) |
| C(21) | 22(1) | 23(1) | 21(1) | 0(1) | 12(1) | 3(1) |
| C(22) | 21(1) | 23(1) | 17(1) | 0(1) | 8(1) | −2(1) |
| C(16) | 18(1) | 24(1) | 17(1) | 4(1) | 8(1) | 3(1) |
| C(24) | 21(1) | 19(1) | 17(1) | 2(1) | 10(1) | 1(1) |
| C(17) | 15(1) | 13(1) | 16(1) | −1(1) | 6(1) | −2(1) |
| C(23) | 19(1) | 26(1) | 17(1) | 0(1) | 8(1) | 2(1) |
| C(25) | 18(1) | 21(1) | 14(1) | 2(1) | 7(1) | 1(1) |
| C(18) | 26(1) | 13(1) | 20(1) | −3(1) | 12(1) | −4(1) |
| C(28) | 28(1) | 23(1) | 19(1) | 1(1) | 11(1) | −6(1) |
| C(15) | 16(1) | 23(1) | 20(1) | 4(1) | 8(1) | 5(1) |

TABLE 5-continued

Anisotropic displacement parameters (Å² × 10³) for compound 28.

| | $U_{11}$ | $U_{22}$ | $U_{33}$ | $U_{23}$ | $U_{13}$ | $U_{12}$ |
|---|---|---|---|---|---|---|
| C(26) | 23(1) | 27(1) | 22(1) | 4(1) | 12(1) | 5(1) |
| C(12) | 16(1) | 17(1) | 17(1) | 0(1) | 8(1) | 2(1) |
| C(27) | 27(1) | 26(1) | 22(1) | −4(1) | 12(1) | −6(1) |

The anisotropic displacement factor exponent takes the form: $-2\pi^2[h^2a^{*2}U_{11} + \ldots + 2hka^*b^*U_{12}]$

TABLE 6

Hydrogen coordinates (×10⁴) and isotropic displacement parameters (Å² × 10³) for compound 28.

| | x | y | z | U(eq) |
|---|---|---|---|---|
| H(8A) | 587 | −324 | 9926 | 29 |
| H(25A) | 643 | −1001 | 870 | 29 |
| H(20A) | 1259 | −1357 | 5811 | 20 |
| H(11A) | 1721 | −1739 | 10257 | 23 |
| H(11B) | 2283 | −359 | 10994 | 23 |
| H(14A) | 1249 | 3347 | 8440 | 18 |
| H(8B) | 769 | 3069 | 9513 | 20 |
| H(9A) | 1752 | 2858 | 10638 | 21 |
| H(9B) | 1505 | 1125 | 11190 | 21 |
| H(21A) | 2152 | −1990 | 7507 | 32 |
| H(21B) | 2421 | −28 | 7139 | 32 |
| H(21C) | 2209 | −2136 | 6334 | 32 |
| H(22A) | 1115 | 1985 | 4708 | 24 |
| H(16A) | 742 | 3572 | 5839 | 24 |
| H(16B) | 505 | 1149 | 5549 | 24 |
| H(24A) | 1107 | −3196 | 4051 | 23 |
| H(24B) | 650 | −1309 | 3530 | 23 |
| H(17A) | 1621 | 2530 | 7189 | 18 |
| H(23A) | 1838 | −968 | 4328 | 25 |
| H(23B) | 1431 | 744 | 3384 | 25 |
| H(18A) | 1067 | −2655 | 8424 | 29 |
| H(18B) | 1265 | −2998 | 7450 | 29 |
| H(18C) | 674 | −1858 | 7106 | 29 |
| H(28A) | 1905 | 3728 | 4712 | 35 |
| H(28B) | 2323 | 2243 | 5783 | 35 |
| H(28C) | 1925 | 3947 | 5962 | 35 |
| H(15A) | 334 | 3852 | 7027 | 24 |
| H(15B) | 196 | 1308 | 6913 | 24 |
| H(26A) | 1218 | −3926 | 1321 | 35 |
| H(26B) | 1516 | −4704 | 2660 | 35 |
| H(26C) | 1617 | −2309 | 2342 | 35 |
| H(12A) | 2168 | −1182 | 9066 | 20 |
| H(12B) | 2174 | 1369 | 9251 | 20 |
| H(27A) | 274 | −4932 | 1054 | 37 |
| H(27B) | 34 | −3932 | 1867 | 37 |
| H(27C) | 522 | −5713 | 2386 | 37 |

TABLE 7

Torsion angles [°] for compound 28.

| | |
|---|---|
| C(18)—C(13)—C(14)—C(8) | 67.4(2) |
| C(12)—C(13)—C(14)—C(8) | −54.7(2) |
| C(17)—C(13)—C(14)—C(8) | −175.91(15) |
| C(18)—C(13)—C(14)—C(15) | −68.20(19) |
| C(12)—C(13)—C(14)—C(15) | 169.64(16) |
| C(17)—C(13)—C(14)—C(15) | 48.45(17) |
| C(15)—C(14)—C(8)—O(8) | 59.6(2) |
| C(13)—C(14)—C(8)—O(8) | −68.6(2) |
| C(15)—C(14)—C(8)—C(9) | −177.56(18) |
| C(13)—C(14)—C(8)—C(9) | 54.2(2) |
| C(12)—C(11)—C(9)—C(8) | 55.3(2) |
| O(8)—C(8)—C(9)—C(11) | 70.4(2) |
| C(14)—C(8)—C(9)—C(11) | −52.1(2) |
| C(21)—C(20)—C(22)—C(28) | −54.6(2) |
| C(17)—C(20)—C(22)—C(28) | 71.9(2) |
| C(21)—C(20)—C(22)—C(23) | 70.8(2) |
| C(17)—C(20)—C(22)—C(23) | −162.74(16) |
| C(21)—C(20)—C(17)—C(16) | −176.42(18) |
| C(22)—C(20)—C(17)—C(16) | 57.7(2) |
| C(21)—C(20)—C(17)—C(13) | −55.8(2) |
| C(22)—C(20)—C(17)—C(13) | 178.32(15) |
| C(15)—C(16)—C(17)—C(20) | 150.05(16) |
| C(15)—C(16)—C(17)—C(13) | 20.2(2) |
| C(18)—C(13)—C(17)—C(20) | −46.7(2) |
| C(14)—C(13)—C(17)—C(20) | −165.79(15) |
| C(12)—C(13)—C(17)—C(20) | 79.5(2) |
| C(18)—C(13)—C(17)—C(16) | 78.05(19) |
| C(14)—C(13)—C(17)—C(16) | −41.02(18) |
| C(12)—C(13)—C(17)—C(16) | −155.70(17) |
| C(28)—C(22)—C(23)—C(24) | −176.00(18) |
| C(20)—C(22)—C(23)—C(24) | 57.3(2) |
| C(25)—C(24)—C(23)—C(22) | 157.17(18) |
| C(23)—C(24)—C(25)—O(25) | −64.0(2) |
| C(23)—C(24)—C(25)—C(27) | 176.22(18) |
| C(23)—C(24)—C(25)—C(26) | 53.1(3) |
| C(8)—C(14)—C(15)—C(16) | −170.25(18) |
| C(13)—C(14)—C(15)—C(16) | −36.2(2) |
| C(17)—C(16)—C(15)—C(14) | 9.5(2) |
| C(9)—C(11)—C(12)—C(13) | −56.0(2) |
| C(18)—C(13)—C(12)—C(11) | −71.3(2) |
| C(14)—C(13)—C(12)—C(11) | 52.8(2) |
| C(17)—C(13)—C(12)—C(11) | 162.55(18) |

X-Ray Analysis of (8S,20R,22R)-Des-A,B-22-methyl-cholestan-8,25-diol (29)

A colorless prism-shaped crystal of dimensions 0.15×0.19×0.55 mm was selected for structural analysis. Intensity data were collected using a Bruker AXS Platinum 135 CCD detector controlled with the PROTEUM software suite (Bruker AXS Inc., Madison, Wis.). The x-ray source was CuK radiation (1.54178 Å) from a Rigaku RU200 x-ray generator equipped with Montel optics, operated at 50 kV and 90 mA. The x-ray data were processed with SAINT version 7.06 A (Bruker AXS Inc.) and internally scaled with SADABS version 2005/1 (Bruker AXS Inc.). The sample was mounted on a glass fiber using vacuum grease and cooled to 100 K. The intensity data were measured as a series of phi and omega oscillation frames each of 1° for 5-10 sec/frame. The detector was operated in 512×512 mode and was positioned 4.5 cm from the sample. Cell parameters were determined from a non-linear least squares fit of 4485 peaks in the range of 4.0<theta<55°. The data were merged to form a set of 5680 independent data with R(int)=0.047.

The monoclinic space group P2(1) was determined by systematic absences and statistical tests and verified by subsequent refinement. The structure was solved by direct methods and refined by full-matrix least-squares methods on $F^2$, (a) G. M. Sheldrick (1994), SHELXTL Version 5 Reference Manual, Bruker AXS Inc.; (b) *International Tables for Crystallography, Vol C*, Kluwer: Boston (1995). Two molecules of compound 12 were present in the asymmetric unit. Hydrogen atom positions were determined from difference peaks and ultimately refined by a riding model with idealized geometry. Non-hydrogen atoms were refined with anisotropic displacement parameters. A total of 379 parameters were refined against 1 restraint and 5680 data to give wR2=0.1103 and S=1.030 for weights of $w=1/[s^2(F^2)+(0.0643P)^2]$, where $P=[F_o^2+2F_c^2]/3$. The final R(F) was 0.0478 for the 5680 observed data. The largest shift/s.u. was 0.001 in the final refinement cycle and the final difference map had maxima and minima of 0.250 and −0.330 e/Å³, respectively. The absolute structure was determined by refinement of the Flack parameter, H. D. Flack, *Acta Cryst. A*, vol. 39, 876-881 (1983). Table 8 shows the crystal data and structure refinement for compound 29. Tables 9-14 show calculated coordinates, parameters, bond lengths and angles for the crystal structure of compound 29.

TABLE 8

Crystal data and structure refinement for compound 29.

| | |
|---|---|
| Empirical formula | C19H36O2 |
| Formula weight | 296.48 |
| Temperature | 100(1) K |
| Wavelength | 1.54178 Å |
| Crystal system, space group | Monoclinic, P2(1) |
| Unit cell dimensions | a = 11.394(2) Å   α = 90° |
| | b = 16.535(3) Å   β = 119.26(3)° |
| | c = 11.450(2) Å   γ = 90° |
| Volume | 1881.9(7) Å$^3$ |
| Z | 4 |
| Calculated density | 1.046 Mg/m$^3$ |
| Absorption coefficient | 0.497 mm$^{-1}$ |
| F(000) | 664 |
| Crystal size | 0.15 × 0.19 × 0.55 mm |
| Theta range for data collection | 4.43 to 64.72° |
| Limiting indices | −13 <= h <= 11, −19 <= k <= 16, 0 <= l <= 13 |
| Reflections collected/unique | 8253/5680 [R(int) = 0.0470] |
| Data/restraints/parameters | 5680/1/379 |
| Goodness-of-fit on F$^2$ | 1.030 |
| Final R indices [I > 2σ(I)] | R1 = 0.0421, wR2 = 0.1062 |
| R indices (all data) | R1 = 0.0478, wR2 = 0.1103 |
| Absolute structure parameter | −0.2(2) |
| Largest diff. peak and hole | 0.250 and −0.330 e/Å$^3$ |

TABLE 9

Atomic coordinates (×10$^4$) and equivalent isotropic displacement parameters (A$^2$ × 10$^3$) for compound 29. U(eq) is defined as one third of the trace of the orthogonalized U$_{ij}$ tensor.

| | x | y | z | U(eq) |
|---|---|---|---|---|
| O(8A) | 7009(1) | 1054(1) | 343(1) | 22(1) |
| O(25A) | 12097(2) | 4501(1) | 9078(2) | 29(1) |
| C(23A) | 10679(2) | 3214(2) | 7126(2) | 22(1) |
| C(17A) | 9015(2) | 2275(2) | 4307(2) | 19(1) |
| C(16A) | 9538(2) | 1393(2) | 4652(2) | 22(1) |
| C(15A) | 9271(2) | 983(2) | 3327(2) | 22(1) |
| C(24A) | 11896(2) | 3094(1) | 8510(2) | 23(1) |
| C(13A) | 8009(2) | 2235(1) | 2769(2) | 17(1) |
| C(14A) | 8839(2) | 1686(1) | 2347(2) | 19(1) |
| C(25A) | 12854(2) | 3814(2) | 9041(2) | 23(1) |
| C(20A) | 8505(2) | 2600(2) | 5234(2) | 25(1) |
| C(8A) | 8224(2) | 1527(2) | 858(2) | 21(1) |
| C(18A) | 6679(2) | 1851(2) | 2518(2) | 21(1) |
| C(27A) | 13970(2) | 3638(2) | 10462(2) | 29(1) |
| C(22A) | 9602(2) | 2555(2) | 6736(2) | 22(1) |
| C(11A) | 7075(2) | 2885(2) | 475(2) | 24(1) |
| C(9A) | 7911(2) | 2324(2) | 110(2) | 24(1) |
| C(12A) | 7733(2) | 3031(1) | 1989(2) | 21(1) |
| C(26A) | 13435(3) | 4031(2) | 8141(2) | 34(1) |
| C(21A) | 7921(3) | 3453(2) | 4862(2) | 35(1) |
| C(28A) | 8960(3) | 2575(2) | 7639(2) | 36(1) |
| O(8B) | 6008(2) | 844(1) | −2333(2) | 29(1) |
| O(25B) | −1758(2) | −138(1) | −11229(2) | 31(1) |
| C(20B) | 3276(2) | 896(1) | −7960(2) | 20(1) |
| C(23B) | 1088(2) | 258(1) | −9811(2) | 23(1) |
| C(8B) | 4624(2) | 615(2) | −2947(2) | 24(1) |
| C(25B) | −951(2) | −457(1) | −11765(2) | 21(1) |
| C(15B) | 4781(2) | −316(2) | −4716(2) | 22(1) |
| C(13B) | 3930(2) | 1048(1) | −5393(2) | 18(1) |
| C(16B) | 4136(2) | −269(2) | −6261(2) | 23(1) |
| C(18B) | 5282(2) | 1414(2) | −5116(2) | 22(1) |
| C(17B) | 3314(2) | 531(1) | −6707(2) | 19(1) |
| C(21B) | 2592(2) | 1722(2) | −8340(2) | 27(1) |
| C(24B) | 494(2) | −514(2) | −10619(2) | 24(1) |
| C(14B) | 4088(2) | 366(1) | −4397(2) | 20(1) |
| C(12B) | 3031(2) | 1699(2) | −5298(2) | 24(1) |
| C(26B) | −1474(2) | −1295(2) | −12333(3) | 32(1) |
| C(22B) | 2623(2) | 297(1) | −9166(2) | 21(1) |

TABLE 9-continued

Atomic coordinates (×10$^4$) and equivalent isotropic displacement parameters (A$^2$ × 10$^3$) for compound 29. U(eq) is defined as one third of the trace of the orthogonalized U$_{ij}$ tensor.

| | x | y | z | U(eq) |
|---|---|---|---|---|
| C(11B) | 3587(2) | 1997(2) | −3844(2) | 29(1) |
| C(28B) | 3045(2) | 500(2) | −10211(2) | 30(1) |
| C(9B) | 3782(2) | 1313(2) | −2879(2) | 29(1) |
| C(27B) | −1056(2) | 106(2) | −12854(2) | 30(1) |

TABLE 10

Bond lengths [Å] for compound 12.

| | | | |
|---|---|---|---|
| O(8A)—C(8A) | 1.442(3) | O(25A)—C(25A) | 1.440(3) |
| C(23A)—C(24A) | 1.524(3) | C(23A)—C(22A) | 1.536(3) |
| C(17A)—C(20A) | 1.536(3) | C(17A)—C(16A) | 1.553(3) |
| C(17A)—C(13A) | 1.564(3) | C(16A)—C(15A) | 1.549(3) |
| C(15A)—C(14A) | 1.521(3) | C(24A)—C(25A) | 1.526(3) |
| C(13A)—C(18A) | 1.534(3) | C(13A)—C(12A) | 1.535(3) |
| C(13A)—C(14A) | 1.549(3) | C(14A)—C(8A) | 1.516(3) |
| C(25A)—C(26A) | 1.515(3) | C(25A)—C(27A) | 1.525(3) |
| C(20A)—C(21A) | 1.527(4) | C(20A)—C(22A) | 1.557(3) |
| C(8A)—C(9A) | 1.515(3) | C(22A)—C(28A) | 1.531(3) |
| C(11A)—C(9A) | 1.526(3) | C(11A)—C(12A) | 1.535(3) |
| O(8B)—C(8B) | 1.428(3) | O(25B)—C(25B) | 1.432(3) |
| C(20B)—C(21B) | 1.526(3) | C(20B)—C(17B) | 1.537(3) |
| C(20B)—C(22B) | 1.561(3) | C(23B)—C(24B) | 1.528(3) |
| C(23B)—C(22B) | 1.531(3) | C(8B)—C(14B) | 1.519(3) |
| C(8B)—C(9B) | 1.528(4) | C(25B)—C(27B) | 1.513(3) |
| C(25B)—C(26B) | 1.523(4) | C(25B)—C(24B) | 1.526(3) |
| C(15B)—C(14B) | 1.520(3) | C(15B)—C(16B) | 1.550(3) |
| C(13B)—C(12B) | 1.525(3) | C(13B)—C(18B) | 1.537(3) |
| C(13B)—C(14B) | 1.550(3) | C(13B)—C(17B) | 1.567(3) |
| C(16B)—C(17B) | 1.556(3) | C(12B)—C(11B) | 1.545(3) |
| C(22B)—C(28B) | 1.529(3) | C(11B)—C(9B) | 1.520(4) |

TABLE 11

Bond angles [°] for compound 29.

| | |
|---|---|
| C(24A)—C(23A)—C(22A) | 113.68(19) |
| C(20A)—C(17A)—C(16A) | 112.36(18) |
| C(20A)—C(17A)—C(13A) | 118.44(17) |
| C(16A)—C(17A)—C(13A) | 103.00(17) |
| C(15A)—C(16A)—C(17A) | 107.12(17) |
| C(14A)—C(15A)—C(16A) | 103.10(19) |
| C(23A)—C(24A)—C(25A) | 115.03(19) |
| C(18A)—C(13A)—C(12A) | 110.07(17) |
| C(18A)—C(13A)—C(14A) | 113.38(18) |
| C(12A)—C(13A)—C(14A) | 107.63(16) |
| C(18A)—C(13A)—C(17A) | 110.06(17) |
| C(12A)—C(13A)—C(17A) | 116.57(19) |
| C(14A)—C(13A)—C(17A) | 98.79(16) |
| C(8A)—C(14A)—C(15A) | 120.18(19) |
| C(8A)—C(14A)—C(13A) | 115.82(17) |
| C(15A)—C(14A)—C(13A) | 104.12(16) |
| O(25A)—C(25A)—C(26A) | 107.5(2) |
| O(25A)—C(25A)—C(27A) | 108.53(18) |
| C(26A)—C(25A)—C(27A) | 110.92(19) |
| O(25A)—C(25A)—C(24A) | 107.75(18) |
| C(26A)—C(25A)—C(24A) | 112.30(19) |
| C(27A)—C(25A)—C(24A) | 109.7(2) |
| C(21A)—C(20A)—C(17A) | 113.0(2) |
| C(21A)—C(20A)—C(22A) | 110.95(19) |
| C(17A)—C(20A)—C(22A) | 112.09(17) |
| O(8A)—C(8A)—C(14A) | 112.21(16) |
| O(8A)—C(8A)—C(9A) | 109.01(17) |
| C(14A)—C(8A)—C(9A) | 109.69(19) |
| C(28A)—C(22A)—C(23A) | 111.49(17) |
| C(28A)—C(22A)—C(20A) | 110.75(18) |
| C(23A)—C(22A)—C(20A) | 112.53(19) |
| C(9A)—C(11A)—C(12A) | 112.28(18) |
| C(8A)—C(9A)—C(11A) | 112.32(18) |

TABLE 11-continued

Bond angles [°] for compound 29.

| | | |
|---|---|---|
| C(13A)—C(12A)—C(11A) | | 111.75(18) |
| C(21B)—C(20B)—C(17B) | | 113.30(18) |
| C(21B)—C(20B)—C(22B) | | 111.07(17) |
| C(17B)—C(20B)—C(22B) | | 111.08(18) |
| C(24B)—C(23B)—C(22B) | | 112.97(18) |
| O(8B)—C(8B)—C(14B) | | 111.57(17) |
| O(8B)—C(8B)—C(9B) | | 110.1(2) |
| C(14B)—C(8B)—C(9B) | | 109.48(18) |
| O(25B)—C(25B)—C(27B) | | 108.53(19) |
| O(25B)—C(25B)—C(26B) | | 108.61(18) |
| C(27B)—C(25B)—C(26B) | | 110.5(2) |
| O(25B)—C(25B)—C(24B) | | 107.65(18) |
| C(27B)—C(25B)—C(24B) | | 111.33(19) |
| C(26B)—C(25B)—C(24B) | | 110.08(19) |
| C(14B)—C(15B)—C(16B) | | 102.99(17) |
| C(12B)—C(13B)—C(18B) | | 110.33(19) |
| C(12B)—C(13B)—C(14B) | | 107.54(17) |
| C(18B)—C(13B)—C(14B) | | 113.00(17) |
| C(12B)—C(13B)—C(17B) | | 116.87(17) |
| C(18B)—C(13B)—C(17B) | | 110.25(17) |
| C(14B)—C(13B)—C(17B) | | 98.39(18) |
| C(15B)—C(16B)—C(17B) | | 106.92(18) |
| C(20B)—C(17B)—C(16B) | | 112.29(18) |
| C(20B)—C(17B)—C(13B) | | 118.48(19) |
| C(16B)—C(17B)—C(13B) | | 103.50(16) |
| C(23B)—C(24B)—C(25B) | | 116.19(19) |
| C(8B)—C(14B)—C(15B) | | 118.99(18) |
| C(8B)—C(14B)—C(13B) | | 116.6(2) |
| C(15B)—C(14B)—C(13B) | | 104.49(17) |
| C(13B)—C(12B)—C(11B) | | 111.47(18) |
| C(28B)—C(22B)—C(23B) | | 110.72(18) |
| C(28B)—C(22B)—C(20B) | | 110.89(19) |
| C(23B)—C(22B)—C(20B) | | 113.04(18) |
| C(9B)—C(11B)—C(12B) | | 112.6(2) |
| C(11B)—C(9B)—C(8B) | | 113.39(19) |

TABLE 12

Anisotropic displacement parameters ($Å^2 \times 10^3$) for compound 29.

| | $U_{11}$ | $U_{22}$ | $U_{33}$ | $U_{23}$ | $U_{13}$ | $U_{12}$ |
|---|---|---|---|---|---|---|
| O(8A) | 25(1) | 17(1) | 23(1) | −3(1) | 11(1) | −2(1) |
| O(25A) | 32(1) | 16(1) | 29(1) | −6(1) | 8(1) | 1(1) |
| C(23A) | 24(1) | 21(1) | 19(1) | −1(1) | 9(1) | −2(1) |
| C(17A) | 17(1) | 23(1) | 16(1) | −1(1) | 8(1) | −2(1) |
| C(16A) | 23(1) | 23(1) | 17(1) | 2(1) | 7(1) | 1(1) |
| C(15A) | 23(1) | 20(1) | 18(1) | −2(1) | 6(1) | 0(1) |
| C(24A) | 27(1) | 19(1) | 19(1) | 0(1) | 9(1) | 2(1) |
| C(13A) | 17(1) | 19(1) | 15(1) | −2(1) | 8(1) | −1(1) |
| C(14A) | 18(1) | 18(1) | 19(1) | −1(1) | 9(1) | 0(1) |
| C(25A) | 26(1) | 20(1) | 21(1) | −5(1) | 9(1) | 1(1) |
| C(20A) | 19(1) | 34(2) | 21(1) | −7(1) | 9(1) | −2(1) |
| C(8A) | 18(1) | 25(1) | 19(1) | −4(1) | 10(1) | −1(1) |
| C(18A) | 20(1) | 25(1) | 18(1) | −3(1) | 10(1) | −3(1) |
| C(27A) | 25(1) | 31(2) | 25(1) | −7(1) | 7(1) | −1(1) |
| C(22A) | 24(1) | 26(1) | 17(1) | −6(1) | 10(1) | −4(1) |
| C(11A) | 27(1) | 21(1) | 21(1) | 4(1) | 10(1) | −1(1) |
| C(9A) | 27(1) | 29(1) | 18(1) | 1(1) | 13(1) | −5(1) |
| C(12A) | 21(1) | 18(1) | 23(1) | 0(1) | 11(1) | −1(1) |
| C(26A) | 32(1) | 41(2) | 30(1) | −10(1) | 16(1) | −13(1) |
| C(21A) | 31(1) | 45(2) | 21(1) | −9(1) | 7(1) | 13(1) |
| C(28A) | 34(1) | 53(2) | 25(1) | −9(1) | 17(1) | −10(1) |
| O(8B) | 19(1) | 42(2) | 18(1) | 3(1) | 4(1) | 3(1) |
| O(25B) | 31(1) | 30(1) | 40(1) | −4(1) | 24(1) | −1(1) |
| C(20B) | 22(1) | 19(1) | 17(1) | 1(1) | 7(1) | −3(1) |
| C(23B) | 24(1) | 22(1) | 18(1) | −2(1) | 7(1) | 3(1) |
| C(8B) | 21(1) | 34(2) | 17(1) | 5(1) | 8(1) | 2(1) |
| C(25B) | 21(1) | 22(1) | 21(1) | −2(1) | 10(1) | 1(1) |
| C(15B) | 21(1) | 19(1) | 20(1) | 2(1) | 6(1) | 0(1) |
| C(13B) | 18(1) | 17(1) | 17(1) | −1(1) | 7(1) | −1(1) |
| C(16B) | 27(1) | 21(1) | 20(1) | −1(1) | 10(1) | 0(1) |
| C(18B) | 22(1) | 24(1) | 19(1) | −3(1) | 8(1) | −6(1) |
| C(17B) | 18(1) | 20(1) | 17(1) | 0(1) | 7(1) | −2(1) |
| C(21B) | 40(1) | 20(1) | 17(1) | 2(1) | 10(1) | 1(1) |

TABLE 12-continued

Anisotropic displacement parameters ($Å^2 \times 10^3$) for compound 29.

| | $U_{11}$ | $U_{22}$ | $U_{33}$ | $U_{23}$ | $U_{13}$ | $U_{12}$ |
|---|---|---|---|---|---|---|
| C(24B) | 24(1) | 21(1) | 24(1) | −1(1) | 10(1) | 3(1) |
| C(14B) | 16(1) | 21(1) | 19(1) | 4(1) | 6(1) | 1(1) |
| C(12B) | 24(1) | 24(1) | 20(1) | 1(1) | 8(1) | 3(1) |
| C(26B) | 25(1) | 25(2) | 38(1) | −8(1) | 10(1) | −1(1) |
| C(22B) | 24(1) | 19(1) | 16(1) | 0(1) | 8(1) | 3(1) |
| C(11B) | 32(1) | 31(2) | 24(1) | −4(1) | 13(1) | 7(1) |
| C(28B) | 36(1) | 34(2) | 21(1) | −2(1) | 14(1) | −1(1) |
| C(9B) | 25(1) | 43(2) | 20(1) | −1(1) | 11(1) | 3(1) |
| C(27B) | 26(1) | 35(2) | 23(1) | 3(1) | 8(1) | −6(1) |

The anisotropic displacement factor exponent takes the form: $-2\pi^2[h^2 a^{*2} U_{11} + \ldots + 2hka^* b^* U_{12}]$

TABLE 13

Hydrogen coordinates ($\times 10^4$) and isotropic displacement parameters ($Å^2 \times 10^3$) for compound 29.

| | x | y | z | U (eq) |
|---|---|---|---|---|
| H(8AA) | 7202 | 573 | 485 | 33 |
| H(25A) | 12570 | 4907 | 9278 | 44 |
| H(23A) | 10981 | 3224 | 6468 | 26 |
| H(23B) | 10277 | 3735 | 7101 | 26 |
| H(17A) | 9774 | 2615 | 4434 | 23 |
| H(16A) | 10493 | 1389 | 5291 | 27 |
| H(16B) | 9068 | 1106 | 5040 | 27 |
| H(15A) | 10079 | 728 | 3421 | 27 |
| H(15B) | 8564 | 581 | 3044 | 27 |
| H(24A) | 12395 | 2627 | 8480 | 27 |
| H(24B) | 11578 | 2975 | 9137 | 27 |
| H(14A) | 9666 | 1989 | 2591 | 22 |
| H(20A) | 7769 | 2245 | 5123 | 30 |
| H(8AB) | 8879 | 1232 | 700 | 25 |
| H(18A) | 6068 | 1828 | 1572 | 31 |
| H(18B) | 6292 | 2171 | 2942 | 31 |
| H(18C) | 6846 | 1314 | 2881 | 31 |
| H(27A) | 14571 | 4092 | 10792 | 44 |
| H(27B) | 14458 | 3166 | 10459 | 44 |
| H(27C) | 13582 | 3547 | 11030 | 44 |
| H(22A) | 10054 | 2032 | 6876 | 27 |
| H(11A) | 6191 | 2649 | 160 | 28 |
| H(11B) | 6959 | 3399 | 23 | 28 |
| H(9AA) | 7423 | 2218 | −845 | 29 |
| H(9AB) | 8747 | 2591 | 314 | 29 |
| H(12A) | 8574 | 3319 | 2288 | 25 |
| H(12B) | 7146 | 3367 | 2175 | 25 |
| H(26A) | 12716 | 4138 | 7253 | 51 |
| H(26B) | 13968 | 3589 | 8116 | 51 |
| H(26C) | 13989 | 4504 | 8484 | 51 |
| H(21A) | 7245 | 3465 | 3935 | 52 |
| H(21B) | 8625 | 3827 | 5013 | 52 |
| H(21C) | 7526 | 3601 | 5404 | 52 |
| H(28A) | 9651 | 2547 | 8559 | 55 |
| H(28B) | 8363 | 2123 | 7434 | 55 |
| H(28C) | 8463 | 3069 | 7490 | 55 |
| H(8BA) | 6481 | 439 | −2080 | 43 |
| H(25B) | −1614 | −395 | −10559 | 46 |
| H(20B) | 4211 | 976 | −7751 | 24 |
| H(23C) | 839 | 293 | −9115 | 28 |
| H(23D) | 702 | 722 | −10396 | 28 |
| H(8BB) | 4541 | 153 | −2455 | 29 |
| H(15C) | 4604 | −835 | −4437 | 26 |
| H(15D) | 5745 | −230 | −4285 | 26 |
| H(16C) | 3550 | −730 | −6675 | 28 |
| H(16D) | 4828 | −269 | −6522 | 28 |
| H(18D) | 5651 | 1727 | −4307 | 33 |
| H(18E) | 5144 | 1757 | −5850 | 33 |
| H(18F) | 5895 | 988 | −5019 | 33 |
| H(17B) | 2386 | 401 | −6940 | 23 |
| H(21D) | 3014 | 2080 | −7585 | 41 |
| H(21E) | 1657 | 1664 | −8602 | 41 |
| H(21F) | 2675 | 1942 | −9072 | 41 |
| H(24C) | 533 | −934 | −10010 | 29 |
| H(24D) | 1062 | −684 | −10987 | 29 |

TABLE 13-continued

Hydrogen coordinates (×10⁴) and isotropic displacement parameters ($\text{Å}^2 \times 10^3$) for compound 29.

|  | x | y | z | U (eq) |
|---|---|---|---|---|
| H(14B) | 3172 | 171 | −4696 | 23 |
| H(12C) | 2134 | 1482 | −5624 | 29 |
| H(12D) | 2968 | 2152 | −5864 | 29 |
| H(26D) | −2384 | −1253 | −13048 | 48 |
| H(26E) | −1445 | −1636 | −11640 | 48 |
| H(26F) | −922 | −1524 | −12667 | 48 |
| H(22B) | 2970 | −244 | −8819 | 25 |
| H(11C) | 4442 | 2265 | −3555 | 35 |
| H(11D) | 2969 | 2390 | −3817 | 35 |
| H(28D) | 2629 | 126 | −10944 | 45 |
| H(28E) | 4005 | 460 | −9811 | 45 |
| H(28F) | 2766 | 1040 | −10533 | 45 |
| H(9BA) | 2907 | 1107 | −3075 | 35 |
| H(9BB) | 4216 | 1525 | −1974 | 35 |
| H(27D) | −1973 | 129 | −13560 | 45 |
| H(27E) | −497 | −92 | −13204 | 45 |
| H(27F) | −763 | 637 | −12489 | 45 |

TABLE 14

Torsion angles [°] for compound 29.

| | |
|---|---|
| C(20A)—C(17A)—C(16A)—C(15A) | 149.10(17) |
| C(13A)—C(17A)—C(16A)—C(15A) | 20.5(2) |
| C(17A)—C(16A)—C(15A)—C(14A) | 9.4(2) |
| C(22A)—C(23A)—C(24A)—C(25A) | −168.75(19) |
| C(20A)—C(17A)—C(13A)—C(18A) | −47.1(3) |
| C(16A)—C(17A)—C(13A)—C(18A) | 77.5(2) |
| C(20A)—C(17A)—C(13A)—C(12A) | 79.1(3) |
| C(16A)—C(17A)—C(13A)—C(12A) | −156.23(17) |
| C(20A)—C(17A)—C(13A)—C(14A) | −166.1(2) |
| C(16A)—C(17A)—C(13A)—C(14A) | −41.40(19) |
| C(16A)—C(15A)—C(14A)—C(8A) | −168.25(18) |
| C(16A)—C(15A)—C(14A)—C(13A) | −36.5(2) |
| C(18A)—C(13A)—C(14A)—C(8A) | 66.7(2) |
| C(12A)—C(13A)—C(14A)—C(8A) | −55.3(2) |
| C(17A)—C(13A)—C(14A)—C(8A) | −176.87(19) |
| C(18A)—C(13A)—C(14A)—C(15A) | −67.5(2) |
| C(12A)—C(13A)—C(14A)—C(15A) | 170.49(17) |
| C(17A)—C(13A)—C(14A)—C(15A) | 48.9(2) |
| C(23A)—C(24A)—C(25A)—O(25A) | 58.3(2) |
| C(23A)—C(24A)—C(25A)—C(26A) | −59.9(3) |
| C(23A)—C(24A)—C(25A)—C(27A) | 176.25(19) |
| C(16A)—C(17A)—C(20A)—C(21A) | −177.05(18) |
| C(13A)—C(17A)—C(20A)—C(21A) | −57.1(3) |
| C(16A)—C(17A)—C(20A)—C(22A) | 56.7(2) |
| C(13A)—C(17A)—C(20A)—C(22A) | 176.68(19) |
| C(15A)—C(14A)—C(8A)—O(8A) | 59.8(3) |
| C(13A)—C(14A)—C(8A)—O(8A) | −66.7(2) |
| C(15A)—C(14A)—C(8A)—C(9A) | −178.85(18) |
| C(13A)—C(14A)—C(8A)—C(9A) | 54.6(2) |
| C(24A)—C(23A)—C(22A)—C(28A) | 65.4(3) |
| C(24A)—C(23A)—C(22A)—C(20A) | −169.45(18) |
| C(21A)—C(20A)—C(22A)—C(28A) | 73.7(3) |
| C(17A)—C(20A)—C(22A)—C(28A) | −159.0(2) |
| C(21A)—C(20A)—C(22A)—C(23A) | −51.8(3) |
| C(17A)—C(20A)—C(22A)—C(23A) | 75.5(3) |
| O(8A)—C(8A)—C(9A)—C(11A) | 71.0(2) |
| C(14A)—C(8A)—C(9A)—C(11A) | −52.2(2) |
| C(12A)—C(11A)—C(9A)—C(8A) | 54.6(2) |
| C(18A)—C(13A)—C(12A)—C(11A) | −70.1(2) |
| C(14A)—C(13A)—C(12A)—C(11A) | 53.9(2) |
| C(17A)—C(13A)—C(12A)—C(11A) | 163.67(17) |
| C(9A)—C(11A)—C(12A)—C(13A) | −56.1(2) |
| C(14B)—C(15B)—C(16B)—C(17B) | 10.3(2) |
| C(21B)—C(20B)—C(17B)—C(16B) | −174.45(18) |
| C(22B)—C(20B)—C(17B)—C(16B) | 59.7(2) |
| C(21B)—C(20B)—C(17B)—C(13B) | −53.8(2) |
| C(22B)—C(20B)—C(17B)—C(13B) | −179.67(17) |
| C(15B)—C(16B)—C(17B)—C(20B) | 148.55(18) |
| C(15B)—C(16B)—C(17B)—C(13B) | 19.6(2) |
| C(12B)—C(13B)—C(17B)—C(20B) | 79.7(2) |
| C(18B)—C(13B)—C(17B)—C(20B) | −47.3(3) |
| C(14B)—C(13B)—C(17B)—C(20B) | −165.72(18) |
| C(12B)—C(13B)—C(17B)—C(16B) | −155.29(19) |
| C(18B)—C(13B)—C(17B)—C(16B) | 77.7(2) |
| C(14B)—C(13B)—C(17B)—C(16B) | −40.70(18) |
| C(22B)—C(23B)—C(24B)—C(25B) | −153.23(19) |
| O(25B)—C(25B)—C(24B)—C(23B) | −53.0(3) |
| C(27B)—C(25B)—C(24B)—C(23B) | 65.8(3) |
| C(26B)—C(25B)—C(24B)—C(23B) | −171.2(2) |
| O(8B)—C(8B)—C(14B)—C(15B) | 57.2(3) |
| C(9B)—C(8B)—C(14B)—C(15B) | 179.4(2) |
| O(8B)—C(8B)—C(14B)—C(13B) | −69.4(2) |
| C(9B)—C(8B)—C(14B)—C(13B) | 52.7(2) |
| C(16B)—C(15B)—C(14B)—C(8B) | −169.37(19) |
| C(16B)—C(15B)—C(14B)—C(13B) | −37.2(2) |
| C(12B)—C(13B)—C(14B)—C(8B) | −55.9(2) |
| C(18B)—C(13B)—C(14B)—C(8B) | 66.1(2) |
| C(17B)—C(13B)—C(14B)—C(8B) | −177.65(17) |
| C(12B)—C(13B)—C(14B)—C(15B) | 170.54(16) |
| C(18B)—C(13B)—C(14B)—C(15B) | −67.5(2) |
| C(17B)—C(13B)—C(14B)—C(15B) | 48.82(18) |
| C(18B)—C(13B)—C(12B)—C(11B) | −68.8(2) |
| C(14B)—C(13B)—C(12B)—C(11B) | 54.9(2) |
| C(17B)—C(13B)—C(12B)—C(11B) | 164.25(19) |
| C(24B)—C(23B)—C(22B)—C(28B) | 75.7(3) |
| C(24B)—C(23B)—C(22B)—C(20B) | −159.22(19) |
| C(21B)—C(20B)—C(22B)—C(28B) | 74.3(2) |
| C(17B)—C(20B)—C(22B)—C(28B) | −158.59(18) |
| C(21B)—C(20B)—C(22B)—C(23B) | −50.7(2) |
| C(17B)—C(20B)—C(22B)—C(23B) | 76.4(2) |
| C(13B)—C(12B)—C(11B)—C(9B) | −56.2(3) |
| C(12B)—C(11B)—C(9B)—C(8B) | 52.8(3) |
| O(8B)—C(8B)—C(9B)—C(11B) | 73.6(2) |
| C(14B)—C(8B)—C(9B)—C(11B) | −49.4(3) |

Example 2

Biological Activity

Vitamin D Receptor Binding
Test Material
Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $\text{TEDK}_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; *J. Exp. Med.* 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24OHase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive intraperitoneal doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Figure 2:
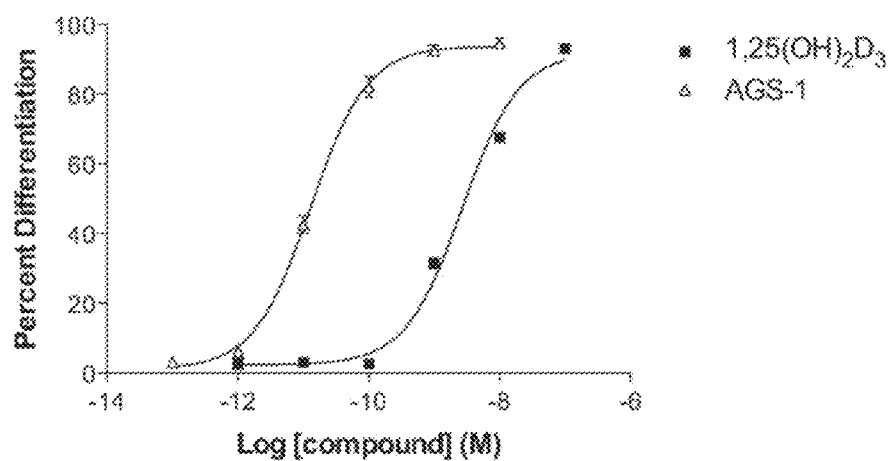
Figure 3:
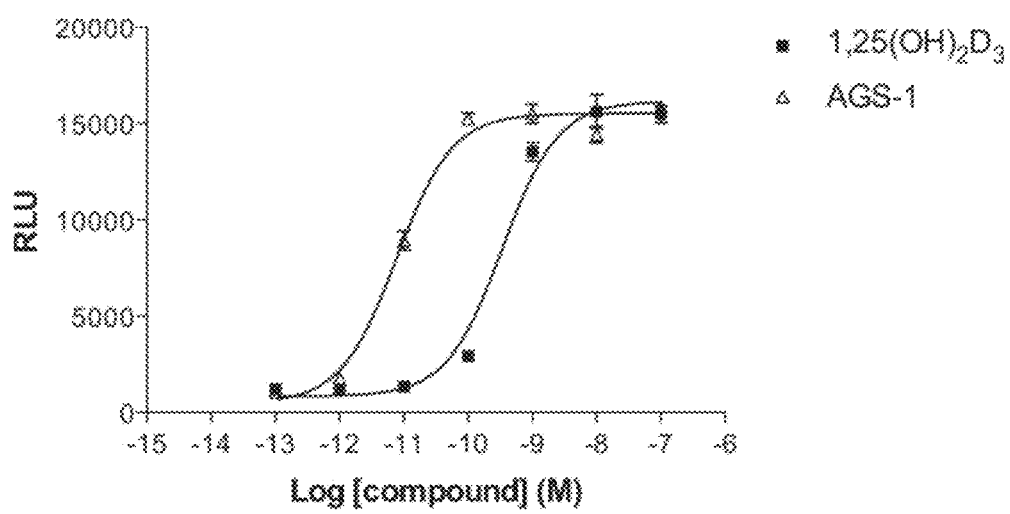

Biological Activity Results (20S,22R)-2-Methylene-19-nor-22-methyl-1α,25-dihydroxyvitamin $D_3$ (AGS-1) is approximately equally effective as 1,25-$(OH)_2D_3$ in binding to the recombinant vitamin D receptor as shown in FIG. 1. However, it is substantially more potent (~300 times) than 1,25-$(OH)_2D_3$ in causing the differentiation of HL-60 cells in culture (FIG. 2). Likewise, it is nearly 40 times more active than 1,25-$(OH)_2D_3$ in increasing transcription of the 24-hydroxylase gene (FIG. 3). In vivo testing demonstrated that this compound is more potent than 1,25-$(OH)_2D_3$ in promoting both bone calcium mobilization (FIGS. 4A and 4B) and intestinal calcium transport (FIG. 4C). Because AGS-1 is dramatically more potent than the native hormone in causing cellular differentiation and has a unique ability to stimulate bone calcium mobilization to a greater level than the native hormone, it may serve as a useful therapy for various bone diseases.

Figure 6:
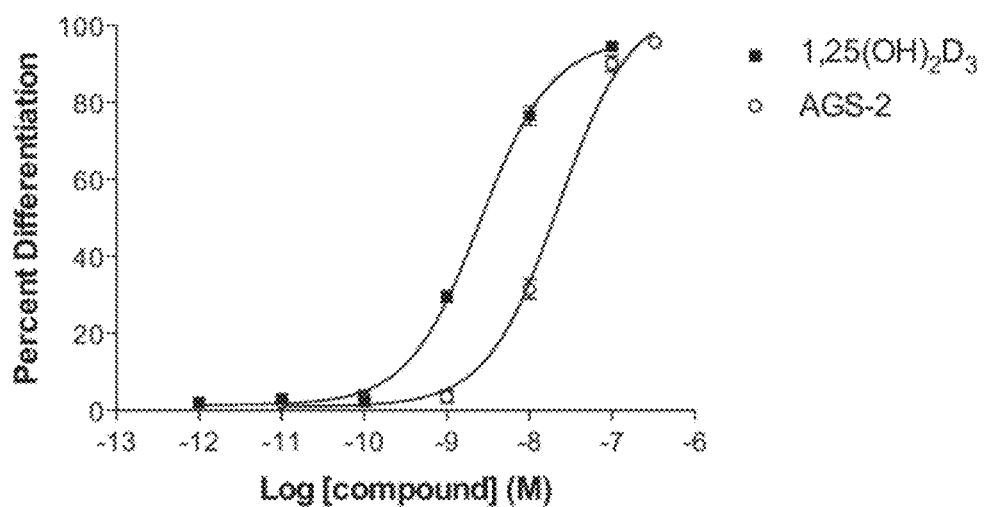
Figure 7:
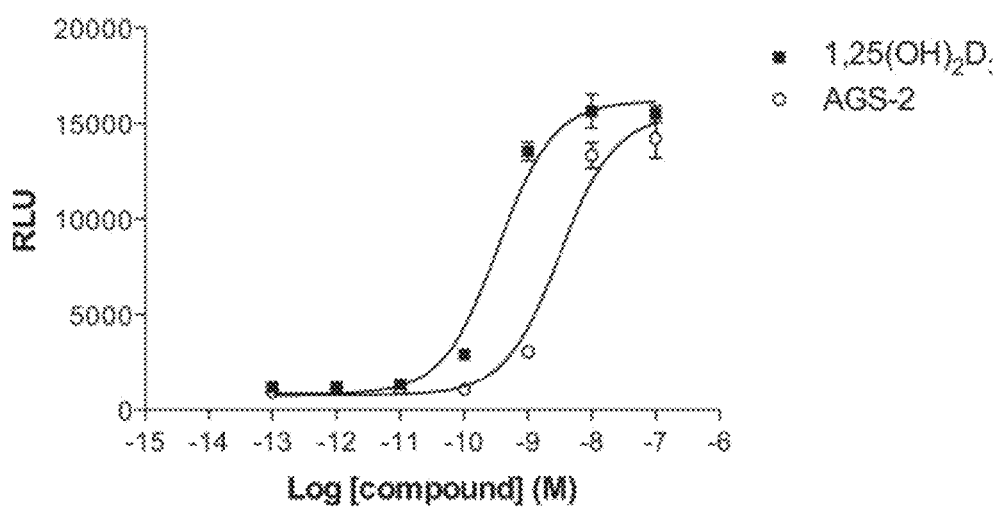
Figure 8A:
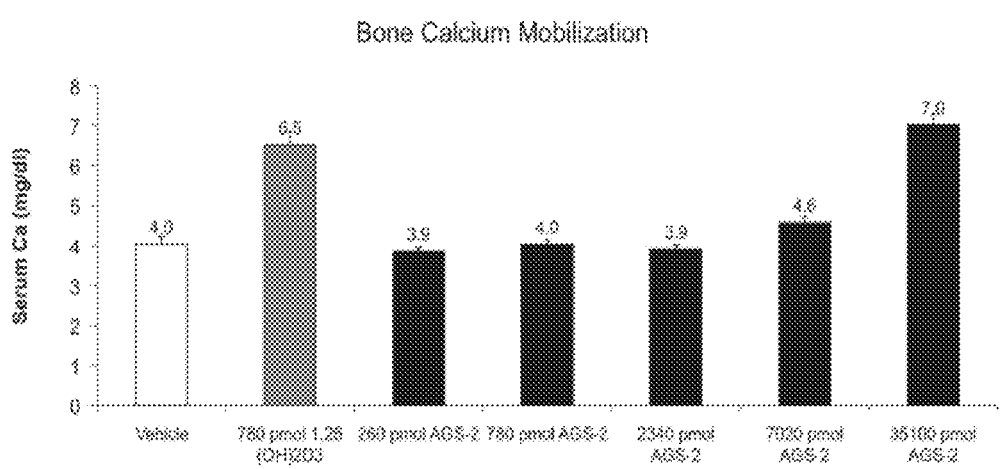
FIG. 8A is a bar graph comparing the bone calcium mobilization activity of AGS-2 with that of 1,25(OH)$_2$D$_3$ in rat. AGS-2 is approximately 50 times less potent than the native hormone in releasing bone calcium stores.
Figure 8B:
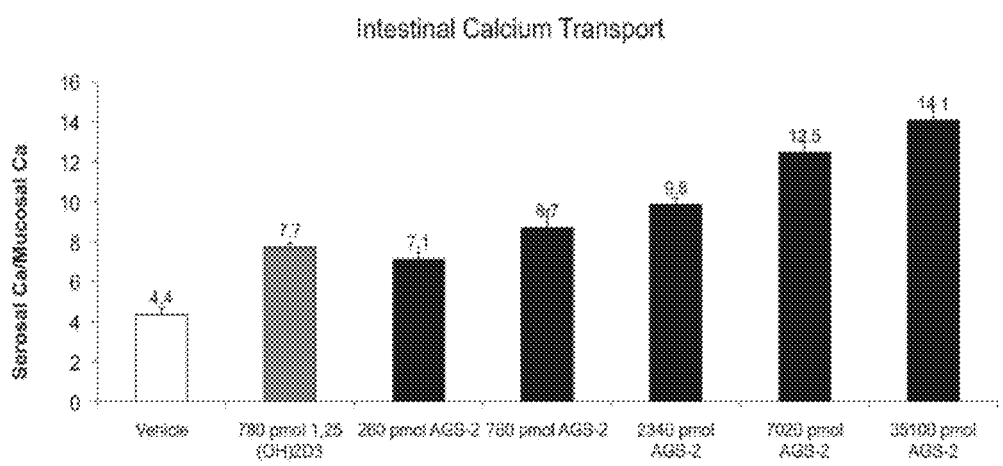
FIG. 8B is a bar graph comparing the intestinal calcium transport activity of AGS-1 with that of 1,25(OH)$_2$D$_3$. The calcemic activity of AGS-2 in the intestine is similar or greater than the native hormone.

On the other hand, (20S,22S)-2-methylene-19-nor-22-methyl-1α,25-dihydroxyvitamin $D_3$ (AGS-2) showed lower affinity relative to 1,25-$(OH)_2D_3$ in binding to the recombinant vitamin D receptor as shown in FIG. 5. Nonetheless, it possesses significant cell differentiation and transcription activity. It is only about 10 times less active than 1,25-$(OH)_2D_3$ in causing the differentiation of HL-60 cells in culture (FIG. 6). Likewise, it is about 10 times less active than 1,25-$(OH)_2D_3$ in increasing transcription of the 24-hydroxylase gene (FIG. 7). In vivo testing demonstrated that AGS-2 has a much reduced ability to mobilize calcium from bone compared to 1,25-$(OH)_2D_3$ (FIG. 8A). However, its intestinal calcium transport activity is similar or greater than 1,25-$(OH)_2D_3$ (FIG. 8B). The intestinal specific nature of AGS-2 coupled with its cellular differentiation activity make it a candidate for therapy in intestinal based diseases, such as Crohn's disease or celiac disease. Further, these compounds should find utility in the treatment of secondary hyperparathyroidism of patients suffering from chronic kidney failure because it is undesirable to elevate serum calcium above normal in these patients for fear of calcification of heart, aorta and other vital organs while suppressing parathyroid gland proliferation and transcription of the preproparathyroid gene. Likewise, these compounds should also be useful in the treatment of malignancy such as breast, colorectal and prostate cancers, or in the treatment of autoimmune diseases such as multiple sclerosis, lupus, rheumatoid arthritis, type 1 diabetes, and inflammatory bowel disease. They should also be useful in preventing transplant rejection.

Figure 9:
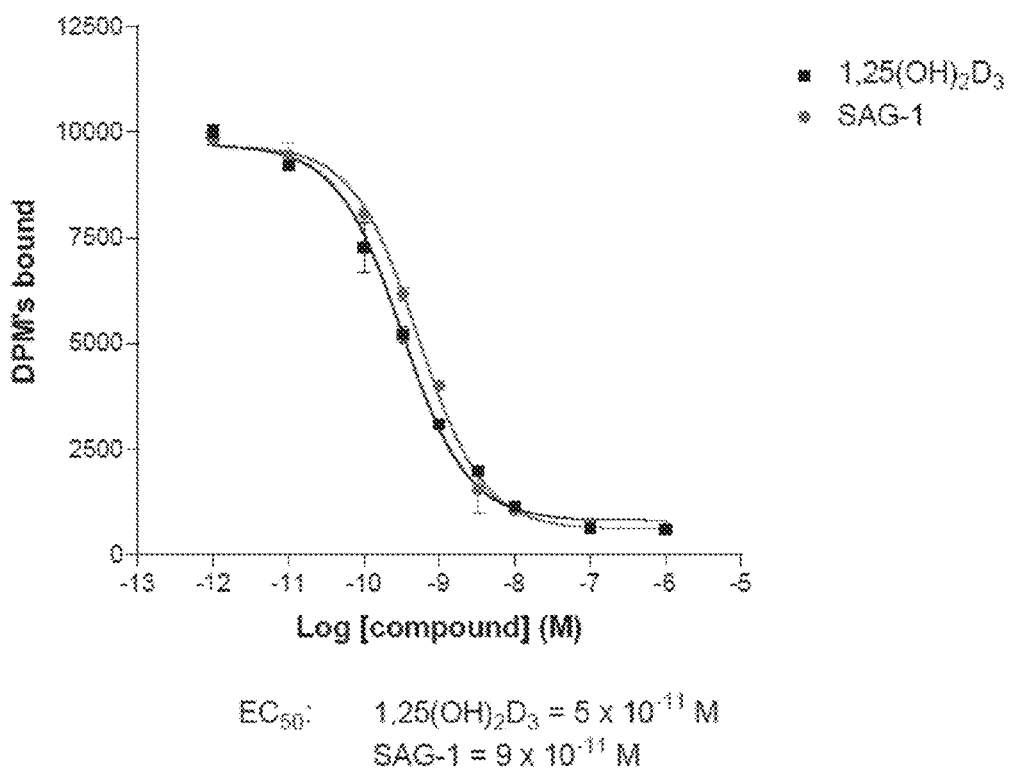
Figure 10:
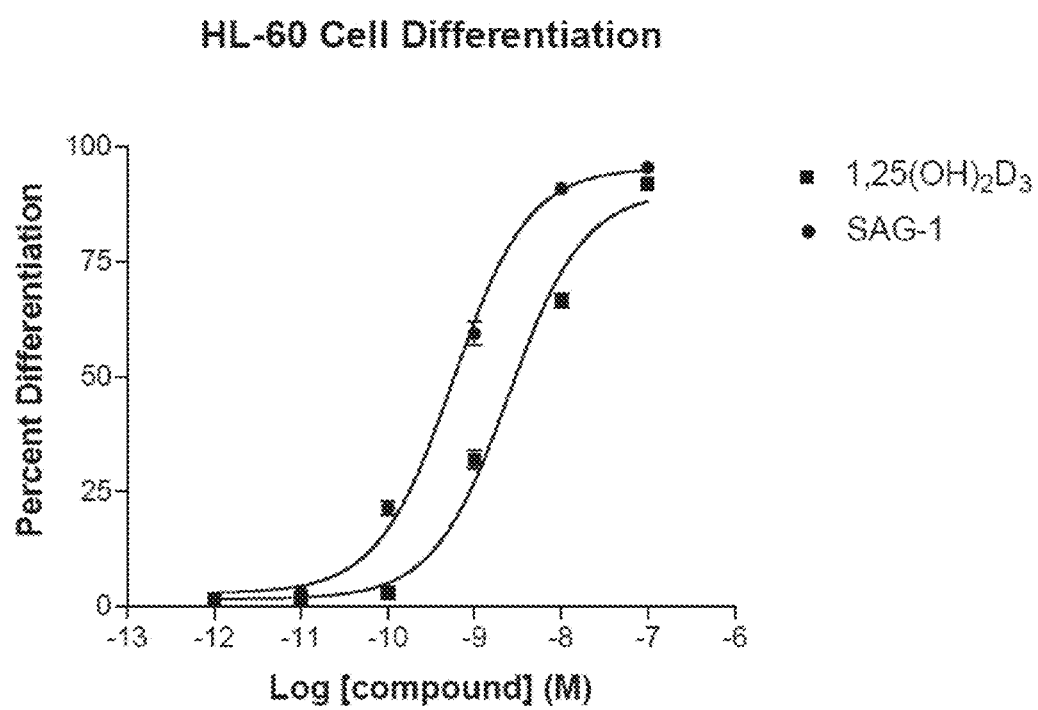
Figure 11:
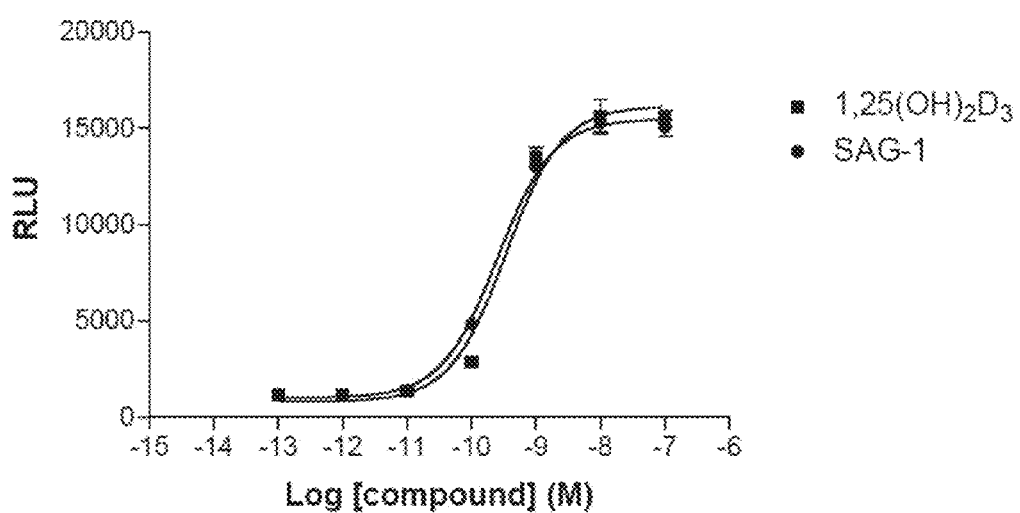
Figure 12C:
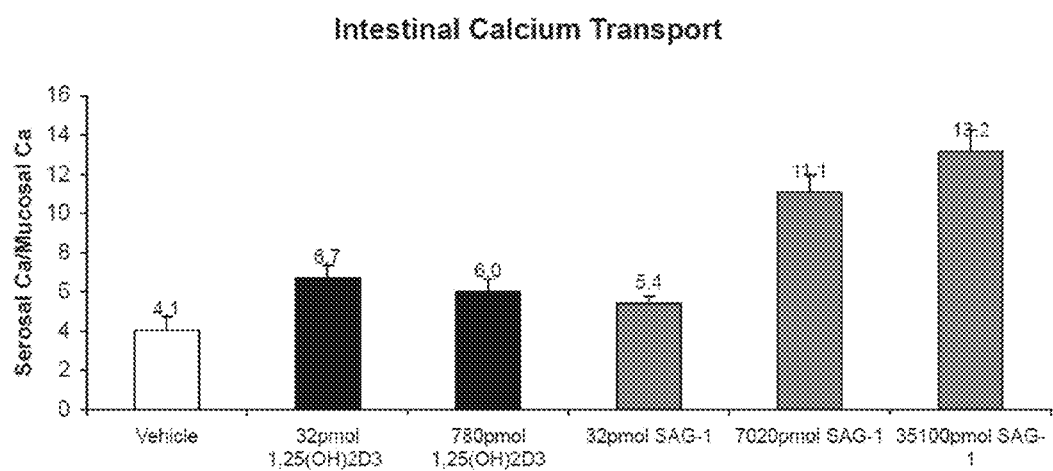
FIG. 12C and FIG. 12D are bar graphs comparing the intestinal calcium transport activity of SAG-1 with that of 1,25(OH)$_2$D$_3$. SAG-1 exhibits similar potency to the native hormone in transporting calcium across the intestinal epithelium.
Figure 12D:
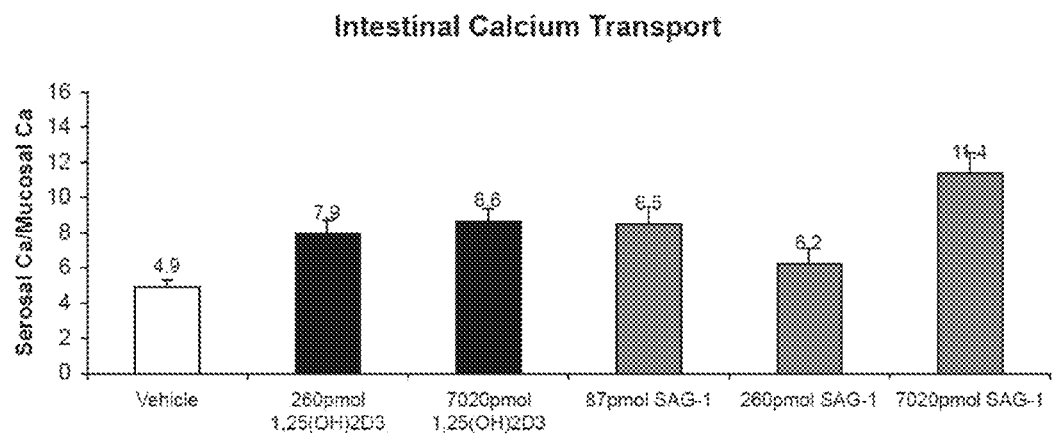

(20R,22S)-2-Methylene-19-nor-22-methyl-1α,25-dihydroxyvitamin $D_3$ (SAG-1) is similar or slightly less effective than 1,25-$(OH)_2D_3$ in binding to the recombinant vitamin D receptor as shown in FIG. 9. However, it is more potent (≥3 times) than 1,25-$(OH)_2D_3$ in causing the differentiation of HL-60 cells in culture (FIG. 10). It is similar to 1,25-$(OH)_2D_3$ in increasing transcription of the 24-hydroxylase gene (FIG. 11), suggesting that there may be some cell-specific differences with SAG-1. In vivo testing demonstrated that this compound is less potent than 1,25-$(OH)_2D_3$ in promoting bone calcium mobilization (FIGS. 12A and 12B) and is of similar potency to 1,25-$(OH)_2D_3$ in intestinal calcium transport (FIGS. 12C and 12D). Thus, SAG-1 has a biological activity profile indicating that it possesses cell specific activity and in vivo shows that it would likely have a larger therapeutic index compared to the native hormone. SAG-1 is likely to be a desirable analog for the potential treatment or prevention of a number of diseases, such as secondary hyperparathyroidism in patients with compromised kidney function, skin diseases such as psoriasis and acne, various types of cancer, bone disorders and possibly some autoimmune diseases.

Figure 13:
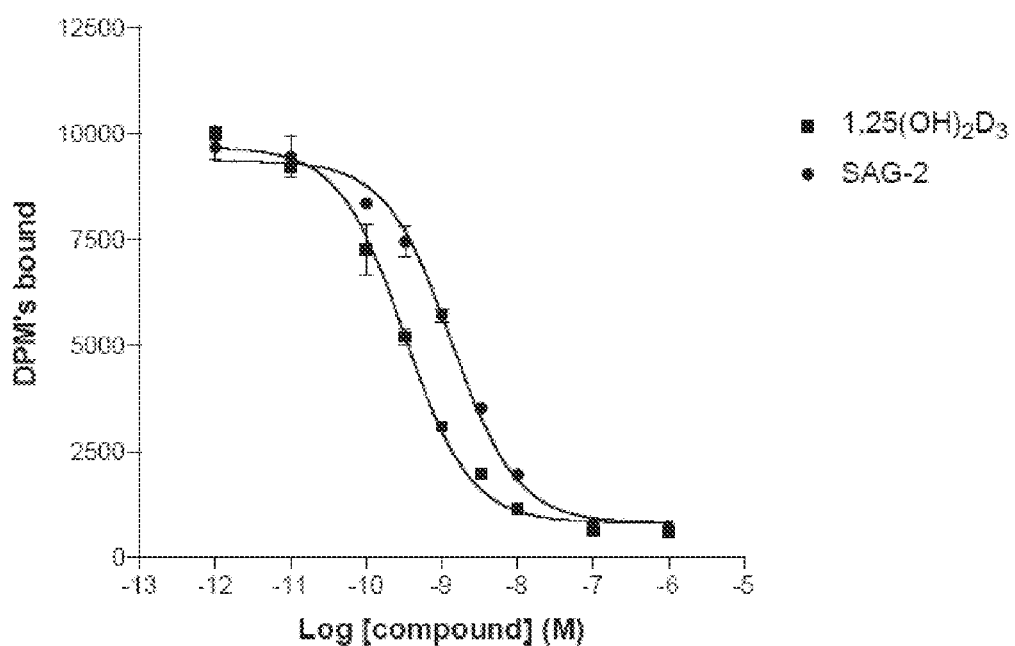
Figure 14:
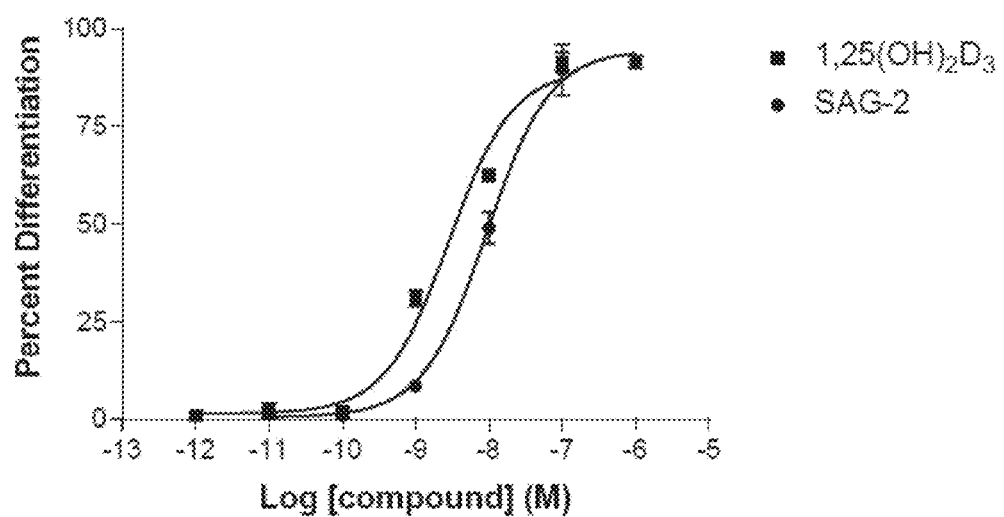
Figure 16C:
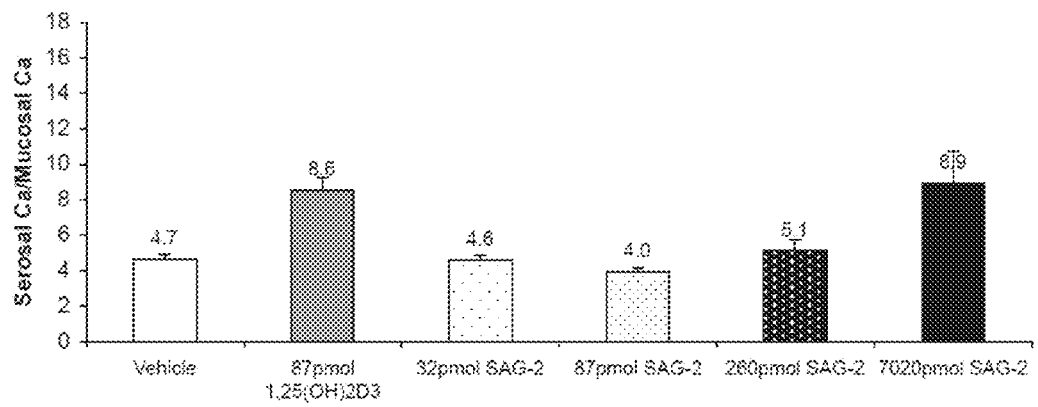
FIG. 16C and FIG. 16D are bar graphs comparing the intestinal calcium transport activity of SAG-2 with that of 1,25(OH)$_2$D$_3$. SAG-2 exhibits less potency compared to the native hormone in transporting calcium across the intestinal epithelium.
Figure 16D:
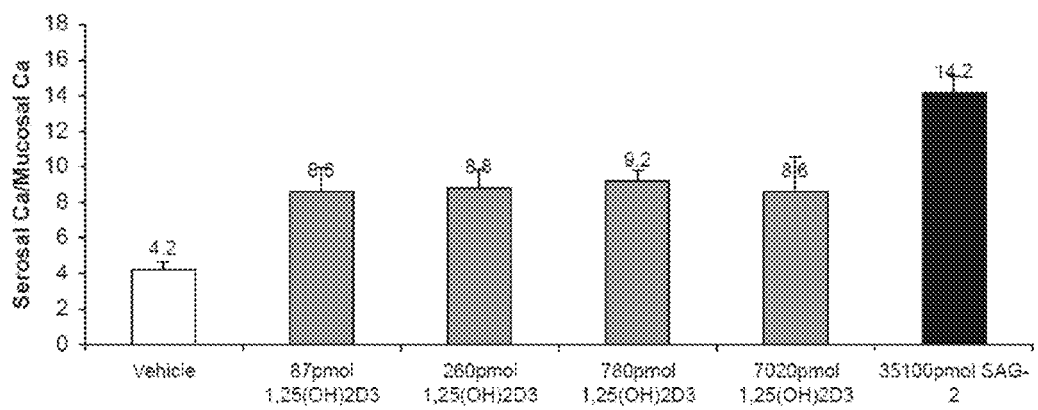
Figure 17A:
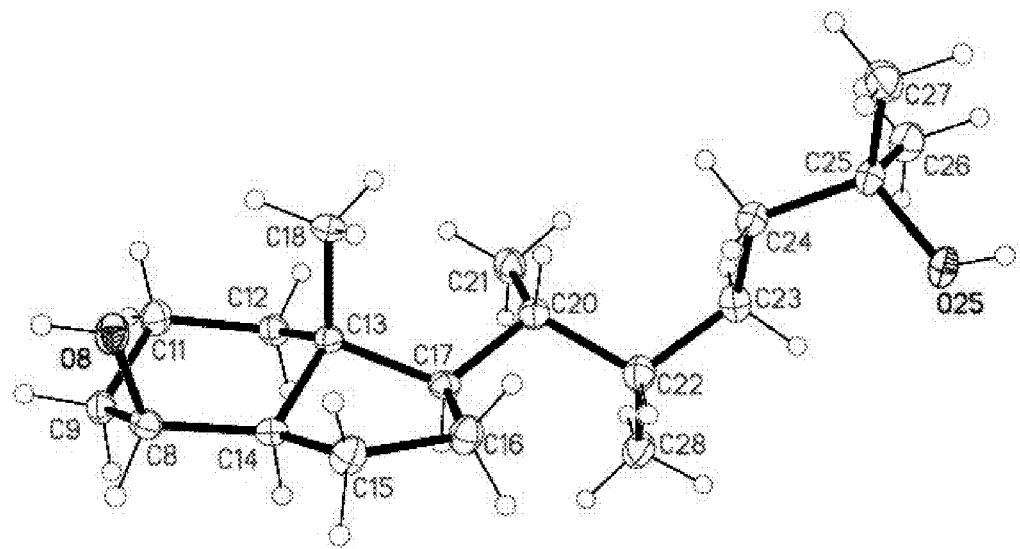
FIG. 17A and FIG. 17B are ORTEP drawings of compounds 28 and 29, respectively, based on single crystal X-ray diffraction analysis.
Figure 17B:
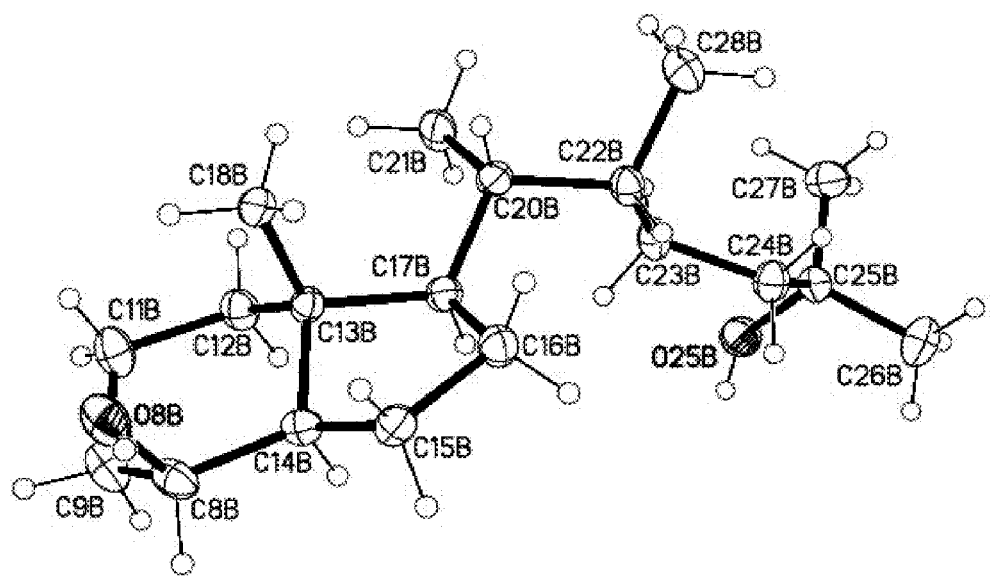

(20R,22R)-2-Methylene-19-nor-22-methyl-1α,25-dihydroxyvitamin $D_3$ (SAG-2) is less effective than 1,25-$(OH)_2D_3$ in binding to the recombinant vitamin D receptor as shown in FIG. 13. It is also less potent (~3 times) than 1,25-$(OH)_2D_3$ in causing the differentiation of HL-60 cells in culture (FIG. 14). It is approximately 20 times less potent than 1,25-$(OH)_2D_3$ in causing transcription of the 24-hydroxylase gene (FIG. 15). In vivo testing demonstrated, that this compound is markedly lower than 1,25-$(OH)_2D_3$ both with respect to promoting bone calcium mobilization (FIGS. 16A and 16B) and in intestinal calcium transport (FIGS. 16C and 16D). Thus, SAG-2 has a biological activity profile indicating that it might possess overall reduced potency, but a larger therapeutic index compared to the native hormone. SAG-2 is likely to be a desirable analog for the potential treatment or prevention of a number of diseases, such as secondary hyperparathyroidism in patients with compromised kidney function, skin diseases such as psoriasis and acne, various types of cancer, bone disorders and possibly some autoimmune diseases.

Comparative Example: Table 1 shows biological data for the compounds from the present disclosure (AGS-1, AGS-2, SAG-1, and SAG-2) in comparison to 2-methylene-19-nor-1α,25-dihydroxyvitamin $D_3$ and its 20R isomer. The former compounds differ from the latter in that they have a methyl group attached to the position 21 carbon. The present AGS and SAG compounds display surprising and unexpected bioactivity in comparison to the 2MD compounds. The 2MD compounds show extremely potent net bone calcium mobilization activity (ranging from 4.5 mg/dL in the 20R isomer to 9.3 mg/dL in the 20S isomer). In stark contrast, AGS-2, SAG-1, and SAG-2 all show no net calcemic activity on bone. While AGS-1 does show activity with regard to net bone calcium mobilization, this compound also shows significant activity on net intestinal calcium transport, (serosal to mucosal ratio of 4.3) unlike the 2MD compounds, which demonstrate intestinal calcemic activity lower than that of vehicle (serosal to mucosal ratios of −0.6 for the 20R isomer and −0.9 for the 20S isomer). Likewise, AGS-2 displays significant net intestinal calcium transport, in contrast to the 2MD compounds. Thus, AGS-2 displays a calcemic activity profile opposite to that of the 2MD compounds. AGS-1 is further differentiated from the 2MD compounds in the HL-60 assay results. In particular, while the 2MD compounds are approximately 1 to 27 times more active than the native hormone in HL-60 differentiation, AGS-1 is ~300 times more active than the native hormone. Thus, AGS-1 is at least 10 time more active than the 20S isomer of 2MD (i.e., 300/27≈11) and more than 300 times more active than the 20R isomer of 2MD (i.e., 300/0.95≈320).

The compounds of the present technology are also useful in preventing or treating obesity, inhibiting adipocyte differentiations, inhibiting SCD-1 gene transcription, and/or reducing body fat in animal subjects. Therefore, in some embodiments, a method of preventing or treating obesity, inhibiting adipocyte differentiations, inhibiting SCD-1 gene transcription, and or reducing body fat in animal subject includes administering to the animal subject, an effective amount of the compound or a pharmaceutical composition that includes the compound. Administration of the compound or the pharmaceutical composition to the subject inhibits adipocyte differentiation, inhibits gene transcription, and/or reduces body fat in the animal subject.

TABLE 1

| Working Example[1] | Where | Side chain | Competitive VDR Binding[2] | HL-60 Differentiation[3] (Relative Activity[4]) | 24OHase Transcription[3] (Relative Activity[4]) | Net Bone $Ca^{2+}$ Mobilization[5] | Net Intestinal $Ca^{2+}$ Transport[6] |
|---|---|---|---|---|---|---|---|
| AGS-1 | Present | | 0.07 | 0.01 (300) | 0.008 (38) | 5.3 | 9.9 |
| AGS-2 | Present | | 8 | 20 (0.15) | 3 (0.1) | 0 | 4.3 |
| SAG-1 | Present | | 0.09 | 0.6 (3.3) | 0.3 (10) | 0.3[7] | 1.3[7] |
| SAG-2 | Present | | 0.2 | 9 (0.3) | 6 (0.05) | −0.1[7] | 0.4[7] |

TABLE 1-continued

| Working Example[1] | Where | Side chain | Competitive VDR Binding[2] | HL-60 Differentiation[3] (Relative Activity[4]) | 24OHase Transcription[3] (Relative Activity[4]) | Net Bone $Ca^{2+}$ Mobilization[5] | Net Intestinal $Ca^{2+}$ Transport[6] |
|---|---|---|---|---|---|---|---|
| 2MD[8] (20R) | U.S. Pat. No. 5,843,928 | 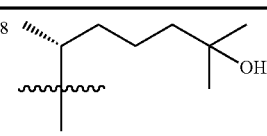 | 0.12 | 4.2 (0.95) | — | 4.5[7] | −0.6[7] |
| 2MD[8] (20S) | U.S. Pat. No. 5,843,928 | 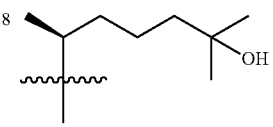 | 0.10 | 0.15 (27) | — | 9.3[7] | −0.9[7] |

[1]All compounds are 2-methylene 19-nor compounds.
[2]$K_i$, nM.
[3]$EC_{50}$, nM.
[4]Activity relative to the native hormone, 1.25(OH)$_2$D$_3$, as measured in the same assay. Relative activity = (value observed for native hormone)/(value observed for working example). Ratios greater than one indicate the working example is more active than the native hormone.
[5]In mg/dL at 780 pM dosage, except where indicated.
[6]Serosal $Ca^{2+}$ to mucosal $Ca^{2+}$ ratio, S/M, at 780 pM dosage, except where indicated.
[7]At 260 pM dosage.
[8]Data from U.S. Pat. No. 5,843,928 and *J. Med. Chem.* 1998, 41, 4662.

It is understood that the present technology is not limited to the embodiments set forth herein for illustration, but embraces all such forms thereof as come within the scope of the following claims.

What is claimed is:

1. A compound according to formula I

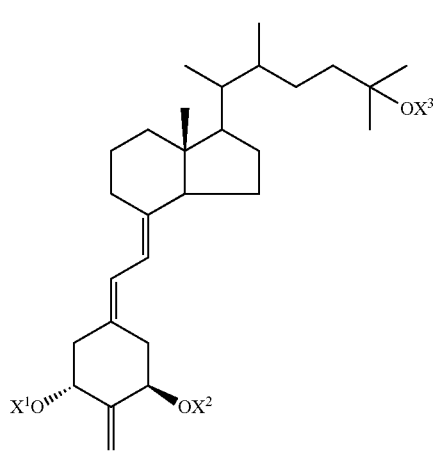

wherein $X^1$, $X^2$, and $X^3$ are independently selected from H and hydroxy protecting groups.

2. The compound of claim 1, wherein $X^1$, $X^2$, and $X^3$ are hydroxy protecting groups.

3. The compound of claim 2, wherein $X^1$ and $X^2$ are both t-butyldimethylsilyl groups and $X^3$ is a triethylsilyl group.

4. A compound according to formula II

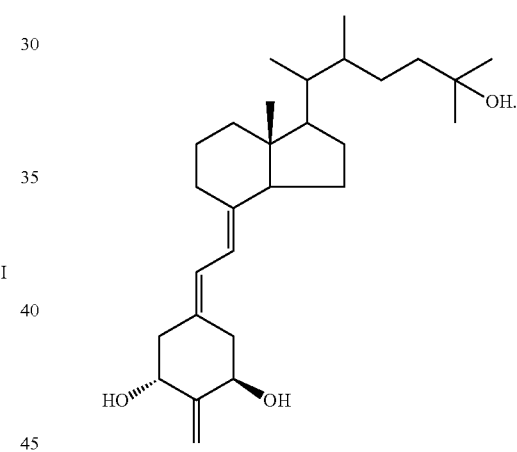

5. The compound of claim 4, according to formula IIA

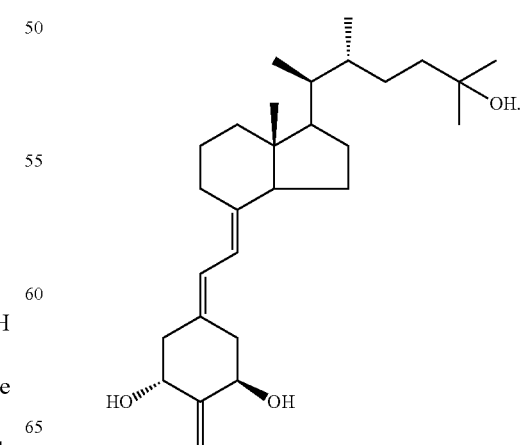

6. The compound of claim 4, according to formula IIB
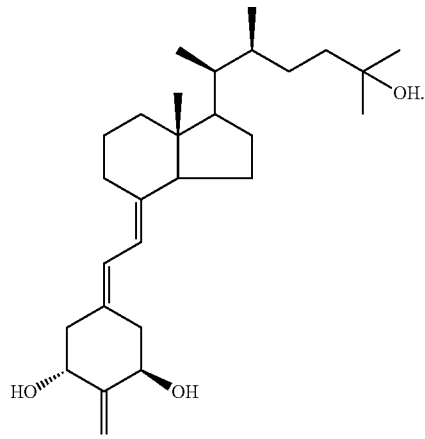
IIB
7. The compound of claim 4, according to formula IIC
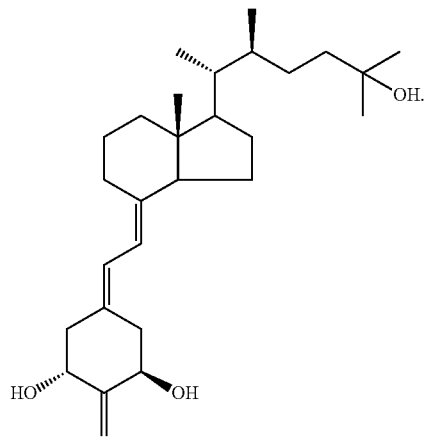
IIC
8. The compound of claim 4, according to formula IID
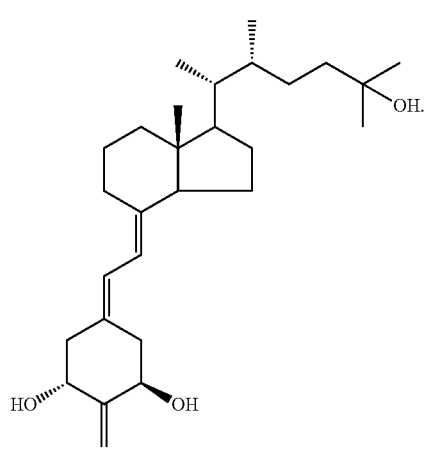
IID
9. The compound of claim 4, according to formula IIE, IIF, IIG, or IIH
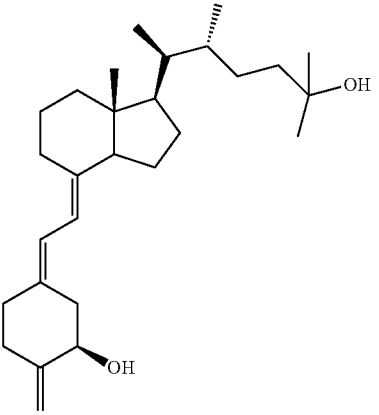
IIE
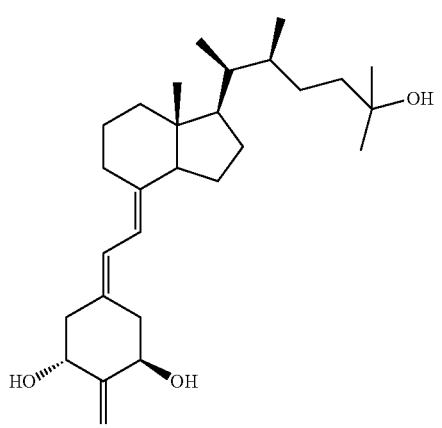
IIF
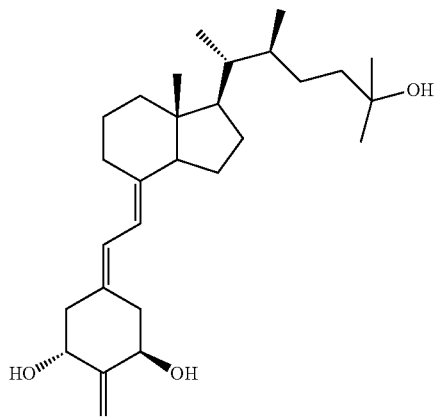
IIG

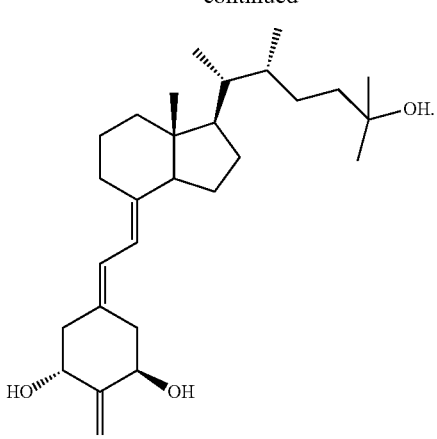

10. The compound of claim 4, according to formula IIG or IIH

IIG

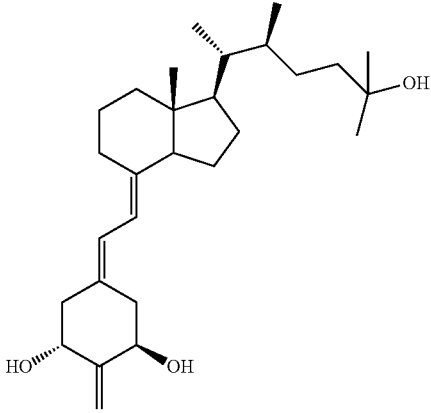

IIH

11. A pharmaceutical composition, comprising an effective amount of the compound of claim 4 and a pharmaceutically acceptable carrier.

12. A method of treating a subject suffering from a biological condition, comprising administering an effective amount of the compound of claim 4 to the subject, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis.

13. The method of claim 12, wherein the biological condition is psoriasis.

14. The method of claim 12, wherein the biological condition is selected from leukemia, colon cancer, breast cancer, or prostate cancer.

15. The method of claim 12, wherein the biological condition is selected from multiple sclerosis, lupus, diabetes mellitus, host versus graft reaction, or rejection of organ transplants.

16. The method of claim 12, wherein the biological condition is selected from rheumatoid arthritis, asthma, or inflammatory bowel diseases selected from celiac disease, ulcerative colitis and Crohn's disease.

17. The method of claim 12, wherein the biological condition is selected from wrinkles, lack of adequate skin firmness, lack of adequate dermal hydration, or insufficient sebum secretion.

18. The method of claim 12, wherein the compound is administered in a dosage of from 0.01 μg per day to 1 mg per day.

19. A compound according to Formula IIIC or IIID, wherein $X^3$ is H:

IIIC

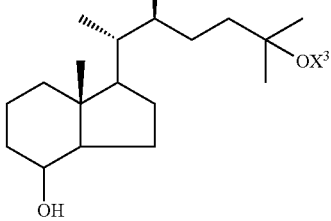

IIID

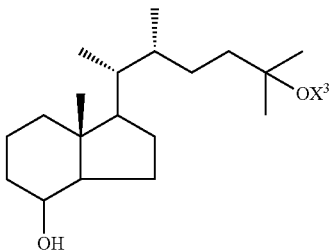

where
Formula IIIC is (20R,22S)-Des-A,B-22-methyl-cholestan-8,25-diol; and
Formula IIID is (20R,22R)-Des-A,B-22-methyl-cholestan-8,25-diol.

20. The compound of claim 19, wherein the compound is in crystalline form.

21. The crystalline compound of claim 20 wherein the compound is of Formula IIIC and has a molecular packing arrangement defined by monoclinic space group C2 and unit cell dimensions a=26.4 Å, α=90°, b=6.08 Å, β=118°, c=12.7 Å, γ=90°.

22. The crystalline compound of claim 20 wherein the compound is of Formula IIID and has a molecular packing arrangement defined by monoclinic space group P2 and unit cell dimensions a=11.4 Å, α=90°, b=16.5 Å, β=119°, c=11.5 Å, γ=90°.

* * * * *